United States Patent
Feder et al.

(10) Patent No.: US 7,624,030 B2
(45) Date of Patent: Nov. 24, 2009

(54) COMPUTER-IMPLEMENTED MEDICAL ANALYTICS METHOD AND SYSTEM EMPLOYING A MODIFIED MINI-MAX PROCEDURE

(76) Inventors: Carlos Feder, 433 Tennessee La., Palo Alto, CA (US) 94306; Tomas Feder, 433 Tennessee La., Palo Alto, CA (US) 94306

( * ) Notice: Subject to any disclaimer, the term of this patent is extended or adjusted under 35 U.S.C. 154(b) by 0 days.

(21) Appl. No.: 12/454,479

(22) Filed: May 18, 2009

(65) Prior Publication Data

US 2009/0259494 A1 Oct. 15, 2009

Related U.S. Application Data

(63) Continuation-in-part of application No. 11/133,726, filed on May 20, 2005, now abandoned.

(51) Int. Cl.
*A61B 5/00* (2006.01)
(52) U.S. Cl. .................................... 705/3; 705/2; 705/4
(58) Field of Classification Search ........................ None
See application file for complete search history.

(56) References Cited

U.S. PATENT DOCUMENTS

| | | | |
|---|---|---|---|
| 4,839,822 | A | 6/1989 | Dormond et al. |
| 5,331,550 | A | 7/1994 | Stafford et al. |
| 5,715,374 | A | 2/1998 | Heckerman et al. |
| 5,922,079 | A | 7/1999 | Booth et al. |
| 6,149,585 | A | 11/2000 | Gray |
| 6,206,829 | B1 * | 3/2001 | Iliff ............................ 600/300 |
| 6,266,645 | B1 * | 7/2001 | Simpson ........................ 705/3 |

(Continued)

OTHER PUBLICATIONS

Spegel, Murray, "Theory and Probability of Statistics" McGraw-Hill Inc. 1991.*

(Continued)

*Primary Examiner*—C. Luke Gilligan
*Assistant Examiner*—Neal R Sereboff
(74) *Attorney, Agent, or Firm*—Marek Alboszta

(57) ABSTRACT

A method and system for medical analytics implemented on a computer and designed to aid a medical professional in diagnosing one or more diseases afflicting a patient. In contrast to prior art, the present method is based on using clinical data (m) that excludes subjective qualities of and also excludes prevalence of the one or more diseases (i). The method uses a knowledge base that contains disease (i) models exhibiting clinical data (m). Clinical data present (j) in the patient are input into the computer. Then, clinical data present (j) are matched with clinical data (m) in the knowledge base to enable the computer to compose a differential diagnosis list of ruled in diagnoses (k), where k=1 . . . n, for each of the disease (i) models that exhibits at least one clinical datum (m) that matches at least one clinical datum present (j) in the patient. In a key step, the computer computes a probability P(k) for each of the ruled in diagnoses (k) with the aid of a mini-max procedure that overcomes prior art limitations of the Bayes formulation and permits the analytics method to consider concurrent and competing diagnoses (k). Furthermore, the method composes pairs of clinical data present (j) and absent (r) in the patient to aid the medical professional in evaluating diagnoses and determining the most cost-effective clinical data to collect for conducting an effective and rapid diagnostic quest.

20 Claims, 28 Drawing Sheets

U.S. PATENT DOCUMENTS

| | | | |
|---|---|---|---|
| 6,687,685 | B1 | 2/2004 | Sadeghi et al. |
| 6,754,655 | B1 | 6/2004 | Segal |
| 6,764,447 | B2 | 7/2004 | Iliff |
| 6,767,325 | B2 | 7/2004 | Iliff |
| 6,817,980 | B2 | 11/2004 | Iliff |
| 7,124,031 | B1 * | 10/2006 | Hoffman et al. ............... 702/19 |
| 7,392,199 | B2 * | 6/2008 | Karlov et al. ................... 705/2 |
| 2002/0087499 | A1 * | 7/2002 | Stockfisch ................... 706/59 |
| 2003/0105716 | A1 | 6/2003 | Sutton et al. |
| 2004/0078222 | A1 | 4/2004 | Khan et al. |
| 2004/0083452 | A1 | 4/2004 | Minor et al. |
| 2005/0065813 | A1 | 3/2005 | Mishelevich et al. |

OTHER PUBLICATIONS http://www.poems.msu.edu/EBM/Diagnosis/Predictive Values.htm.

Strecker, W., Epidemiology and Clinical Manifestation of HIV Infection in Northern Zaire, Dec. 22, 1993, Kluwer Academy, Pub: European Journal of Epidemiology, 10, 95-98.

Presser, Gero, Dynamic Decision Making Based on Partial Probability, 2001, Springer-Verlag Berlin Heidelberg, p. 930.

Huang et al., "Biased Minimax Probability Machine for Medical Diagnosis", Chinese University of Hong Kong, Nov. 2003.

Michigan State University, "An Introduction to Information Mastery", as found on www.poems.msu.edu/infomastery/1/22/2009.

Schaum's Outline of Theory and Problems of Statistics, 1991 McGraw-Hill Inc.

Iliad 4.5 Diagnostic and Reference Tool for Physicians and Medical Professionals. User Guide 1998.

Shwe M et el. Probabilistic diagnosis using a reformulation of the Internist 1/QMR knowledge bate I. Methods of Information in medicine, 30(4):241-255, 1991, SMI-90/0296.

Middleton B et al. Probabilistic diagnosis using a reformulation of the Internist 1/QMR knowledge base II. Section on medical informatics, technical report. SMI-90-0329, 1990.

Miiler RA, Pople HE and Myers JD. Internist I an experimental computer based diagnostic consultant for general internal medi. The new England Journal of Medicine, 1982:468-476.

Ludwig DW. Infernet—A computer based system for modeling medical kn. Proceedings of the fifth-annual sympsium on computer applications in medical care. 243-249, Nov. 1981.

Szolovits P and Pauker SG, Categorical and probabilistic reasoning in medical diagnosis. Artificial intelligence. 11:115-144, 1978.

Lusted LB. Twenty years of medical decision making studies. CH1480-3/79/0000-0004$00.75. 1979-IEEE.

Blois MS; Tuttle MS, and Sherertz DD. Reconsider; a program for generating differential diagnoses, IEEE: 263-268, 1981.

Pople HE, Myers JD, and Miller RA, Dialog: a model. Forth International joint conference on artificial Intelligence, Tolisi, Gerogia URRS, Sep. 3-8, 1975, vol. 2.1975:848-855.

Shortlife EH, Computer-based medical consultation: Mycln; American Elsevier publishing company, 1976.

* cited by examiner

| diagnosis (k) = (TB) | PP(k)j = partial P(k) prior to considering (r) | partial P(k)j,r (r) = (absent cavity) S(k)r=0.60 | partial P(k)j,r (r) = (absent fever) S(k)r=0.70 | minimum value in each row |
|---|---|---|---|---|
| (j) = (cough) | 0.276 | 0.151 | 0.113 | 0.113 |
| (j) = (hemoptysis) | 0.222 | 0.116 | 0.093 | 0.093 |
| (j) = (dyspnea) | 0.148 | 0.077 | 0.060 | 0.060 |
| (j) = (expectoration) | 0.417 | 0.248 | 0.180 | 0.180 |
| (j) = (MTb) | 1.000 | 1.000 | 1.000 | 1.000 |
| maximum value in each column | 1.000 | 1.000 | 1.000 | TP(TB)=1.000 |

MTb = Mycobacterium tuberculosis

32

38(EB)

| diagnosis (k) = (EB) | PP(k)j = partial P(k) prior to considering (r) | partial P(k)j,r (r) = (absent cavity) S(k)r=0.00 | partial P(k)j,r (r) = (absent fever) S(k)r=0.30 | minimum value in each row |
|---|---|---|---|---|
| (j) = (cough) | 0.172 | 0.236 | 0.165 | 0.165 |
| (j) = (hemoptysis) | 0.333 | 0.435 | 0.325 | 0.325 |
| (j) = (dyspnea) | 0.370 | 0.478 | 0.350 | 0.350 |
| (j) = (expectoration) | 0.010 | 0.016 | 0.010 | 0.010 |
| (j) = (MTb) | 0.000 | 0.000 | 0.000 | 0.000 |
| maximum value in each column | 0.370 | 0.478 | 0.350 | TP(EB)=0.350 |

MTb = Mycobacterium tuberculosis

| diagnosis (k) = (BR) | PP(k)j = partial P(k) prior to considering (r) | partial P(k)j,r (r) = (absent cavity) S(k)r=0.10 | partial P(k)j,r (r) = (absent fever) S(k)r=0.00 | minimum value in each row |
|---|---|---|---|---|
| (j) = (cough) | 0.310 | 0.382 | 0.425 | 0.310 |
| (j) = (hemoptysis) | 0.167 | 0.196 | 0.233 | 0.167 |
| (j) = (dyspnea) | 0.037 | 0.043 | 0.050 | 0.037 |
| (j) = (expectoration) | 0.469 | 0.628 | 0.675 | 0.469 |
| (j) = (MTb) | 0.000 | 0.000 | 0.000 | 0.000 |
| maximum value in each column | 0.469 | 0.628 | 0.675 | TP(BR)=0.469 |

MTb = Mycobacterium tuberculosis

| diagnosis (k) = (LC) | PP(k)j = partial P(k) prior to considering (r) | partial P(k)j,r (r) = (absent cavity) S(k)r=0.30 | partial P(k)j,r (r) = (absent fever) S(k)r=0.10 | minimum value in each row |
|---|---|---|---|---|
| (j) = (cough) | 0.241 | 0.231 | 0.297 | 0.231 |
| (j) = (hemoptysis) | 0.278 | 0.254 | 0.349 | 0.254 |
| (j) = (dyspnea) | 0.444 | 0.402 | 0.540 | 0.402 |
| (j) = (expectoration) | 0.104 | 0.109 | 0.135 | 0.104 |
| (j) = (MTb) | 0.000 | 0.000 | 0.000 | 0.000 |
| maximum value in each column | 0.444 | 0.402 | 0.540 | TP(LC)=0.402 |

MTb = Mycobacterium tuberculosis

| diagnosis (k) = (LC) | PP(k)j = partial P(k) prior to considering (r) | partial P(k)j,r (r) = (absent cavity) S(k)r=0.30 | partial P(k)j,r (r) = (absent fever) S(k)r=0.10 | minimum value in each row |
|---|---|---|---|---|
| (j) = (cough) | 0.241 | 0.231 | 0.297 | 0.231 |
| (j) = (hemoptysis) | 0.278 | 0.254 | 0.349 | 0.254 |
| (j) = (dyspnea) | 0.444 | 0.402 | 0.540 | 0.402 |
| (j) = (expectoration) | 0.104 | 0.109 | 0.135 | 0.104 |
| (j) = (MTb) | 0.000 | 0.000 | 0.000 | 0.000 |
| (j) = (mass) | 0.857 | 0.857 | 0.925 | 0.857 |
| maximum value in each column | 0.857 | 0.857 | 0.925 | TP(LC)=0.857 |

38D(k)

MTb = Mycobacterium tuberculosis

| diagnosis (k) = (LC) | PP(k)j = partial P(k) prior to considering (r) | partial P(k)j,r (r) = (absent cavity) S(k)r=0.30 | partial P(k)j,r (r) = (absent fever) S(k)r=0.10 | partial P(k)j,r (r) = (absent mass) S(k)r=0.90 | minimum value in each row |
|---|---|---|---|---|---|
| (j) = (cough) | 0.241 | 0.231 | 0.297 | | |
| (j) = (hemoptysis) | 0.278 | 0.254 | 0.349 | | |
| (j) = (dyspnea) | 0.444 | 0.402 | 0.540 | 0.078 | 0.078 |
| (j) = (expect.) | 0.104 | 0.109 | 0.135 | | |
| (j) = (MTb) | 0.000 | 0.000 | 0.000 | | |
| | | | | | |
| maximum value in each column | 0.444 | 0.402 | 0.540 | | |

MTb = Mycobacterium tuberculosis

Fig. 6C

| diagnosis (k) = (LC) | PP(k)j = partial P(k) prior to considering (r) | partial P(k)j,r (r) = (absent cavity) S(k)r=0.30 | partial P(k)j,r (r) = (absent fever) S(k)r=0.10 | partial P(k)j,r (r) = (absent mass) S(k)r=0.90 | minimum value in each row |
|---|---|---|---|---|---|
| (j) = (cough) | 0.241 | 0.231 | 0.297 | 0.032 | 0.032 |
| (j) = (hemoptysis) | 0.278 | 0.254 | 0.349 | 0.039 | 0.039 |
| (j) = (dyspnea) | 0.444 | 0.402 | 0.540 | 0.078 | 0.078 |
| (j) = (expect.) | 0.104 | 0.109 | 0.135 | 0.012 | 0.012 |
| (j) = (MTb) | 0.000 | 0.000 | 0.000 | 0.000 | 0.000 |
| | | | | | |
| maximum value in each column | 0.444 | 0.402 | 0.540 | 0.078 | TP(LC)=0.078 |

MTb = Mycobacterium tuberculosis

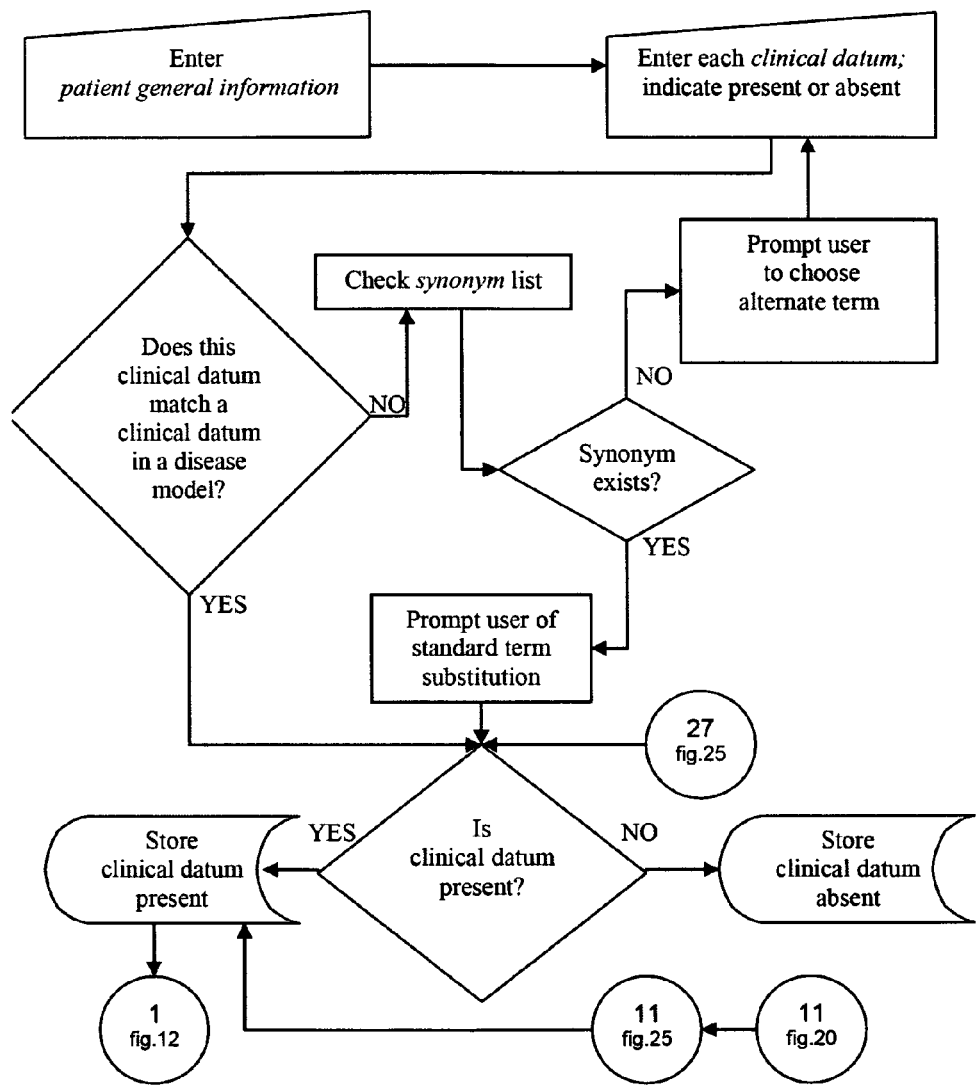
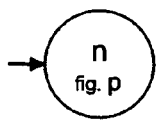 *Outconnector*: n connects to inconnector n located on Fig. p
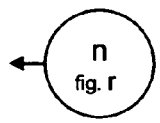 *Inconnector*: n receives connection from outconnector n located on Fig. r
*Fig. 11*

Step 1. Process Clinical Data Present

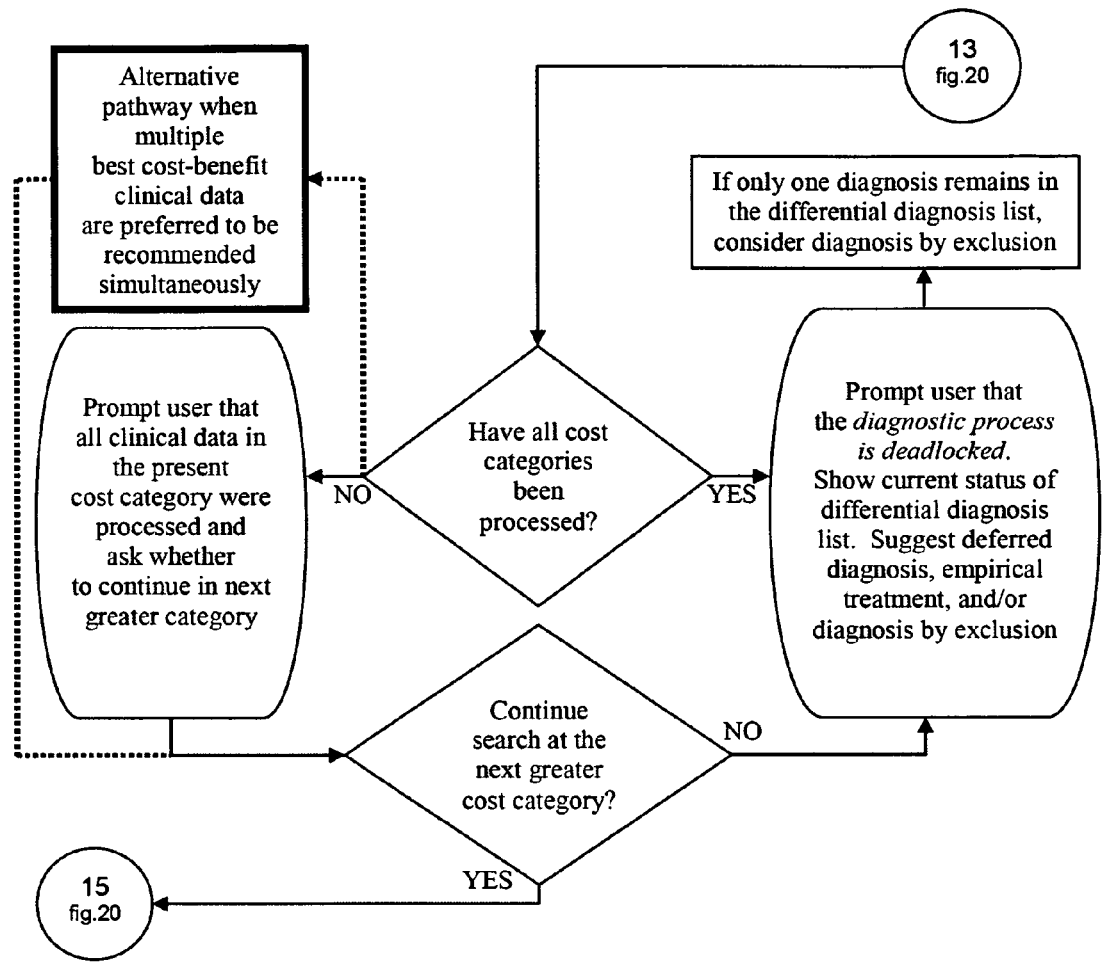
Step 4. Recommend a best cost-benefit clinical datum assuming it absent
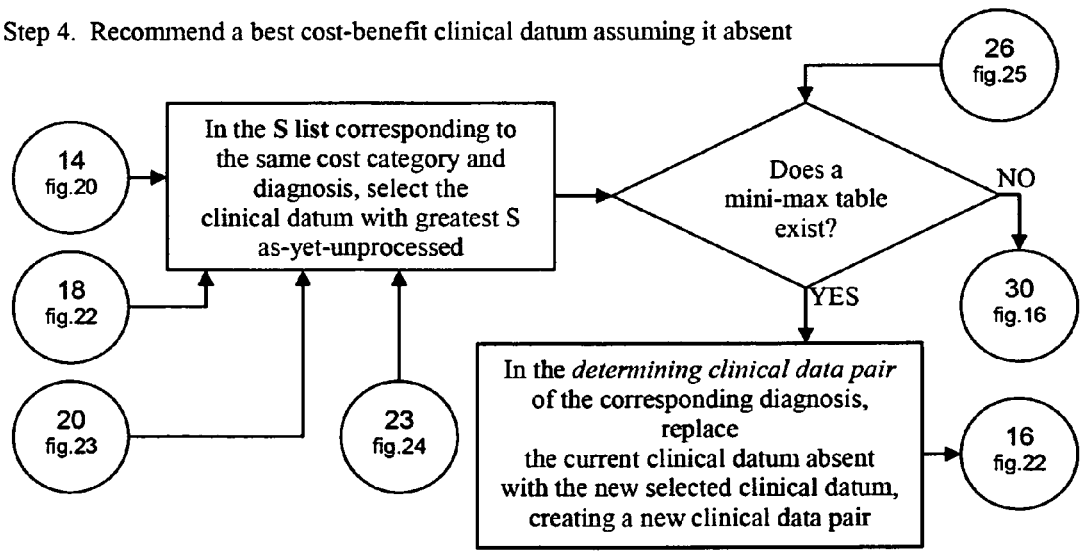
Fig. 21

This check is superfluous if the preferred all-inclusive method to integrate a differential diagnosis list with all the diagnoses in all the clinical datum lists is implemented; in this case the subroutine can directly jump from connector 31 to connector 33 (dashed arrow)

COMPUTER-IMPLEMENTED MEDICAL ANALYTICS METHOD AND SYSTEM EMPLOYING A MODIFIED MINI-MAX PROCEDURE

CROSS REFERENCE TO RELATED APPLICATIONS

The present application is a continuation-in-part (CIP) of application Ser. No. 11/133,726 titled "Computerized Medical Diagnosis: A Fresh Approach to an Old Unsolved Problem" and filed on May 20, 2005 now abandoned.

FIELD OF THE INVENTION

This invention relates generally to a computer-implemented medical analytics method and system that employ a modified mini-max procedure in which subjective criteria affecting clinical data and the prevalence of diseases among potential diagnoses are disregarded.

BACKGROUND ART

The creation of computer programs that emulate the complex task of medical diagnosis is a goal pursued by many researchers, for the past half a century. The success up to the present day is only limited. Although several diagnostic programs exist, of which some are commercially available; namely QMR, ILIAD, DXplain, GIDEON and others, they offer restricted diagnostic information. When a patient's symptoms or clinical data are provided to the computer, these programs typically retrieve a long list of possible diagnoses, instead of pinpointing more specifically one or a few diagnoses. Moreover, they exclude very rare diseases.

Prior art calculation of probability for a given diagnosis, including rare diagnoses of rare diseases, is routinely inaccurate because it usually relies on Bayes formula. Bayes calculation requires that clinical data manifested by a patient be independent, and the diagnoses exhaustive and incompatible. These conditions are frequently not fulfilled by actual clinical cases encountered in medical practice.

As a consequence of Ledley and Lusted's efforts, Bayes formula has become extensively used in medical applications. However, when improperly applied in a diagnostic algorithm, as often is the case, it can cause significant inaccuracies. Bayes formula is valid only when the above-mentioned three conditions are fulfilled. More precisely stated:

(i) The diseases processed by the formula must be exhaustive: all known diseases that manifest the considered clinical datum must be included in its denominator. If this condition is violated, some clinical datum originated by a disease not included in the formula will distort the calculated result. Accordingly, the calculated probability of the diagnosis under consideration will be incorrect and will adversely affect the differential diagnosis.

(ii) Clinical data used for calculation of the conditional probability of a diagnosis must be independent: that is, a specific clinical datum should neither favor nor disfavor any other clinical datum of the same disease. In other words, the probability that one clinical datum is manifested by a specific disease, should not depend on the presence of another clinical datum. This is not true in actual clinical cases, where clinical data result from a chain of reactions that originate in a common cause or lesion and are necessarily related. These clinical data configure syndromes that by definition are associations of related clinical data (e.g., jaundice, increased blood bilirubin, and dark urine.) Bayes formula often is applied erroneously to interrelated clinical data of a specific disease, violating this condition of independence and yielding an inaccurate result. To solve the problems of independence and incompatibility, so-called Bayesian networks have been devised, but their application to diagnostic algorithms is excessively complicated and hard to compute.

(iii) The diseases must be incompatible, which means that clinical data justified by one disease cannot be justified by another disease. When concurrent diseases occur, some clinical data may be caused by more than one of them. Because Bayes formula is only capable to calculate probabilities of competing diagnosis, which are incompatible, it is unsuitable to handle concurrent diseases, afflicting the same patient simultaneously.

In addition to the above limitations, few of the prior art programs, if any, recommend a probabilistically calculated best cost-benefit clinical datum to investigate in the patient at each diagnostic step. Such recommendation, however, could precipitate a more efficient, economic and rapid final diagnosis. In addition, none of the prior art programs recommends on a probabilistically calculated basis, a set of clinical data to be investigated in the patient simultaneously, as required to avoid the need of the physician to contact the patient after each new test result to order the next one. Furthermore, although the cost of investigating a clinical datum is mentioned by some prior art teachings, none offer an effective way to consider the expense beyond dollar cost to include discomfort and risk of the procedure to obtain the datum.

Moreover, prior art programs typically do not diagnose concurrent diseases afflicting a patient. They also do not prepare complex clinical presentations of a specific disease with its diverse complications and associations of clinical entities, interactions between concurrent diseases or drugs that may mask important clinical data of the primary disease, and many other nuances related to clinical practice. A part of this problem is due to the fact that the prior art programs encounter fundamental difficulties in trying to distinguish competing diagnoses from concurrent diagnoses.

The reason for many of the limitations of the prior art diagnostic programs is due to their underlying mathematical approach. Specifically, they are usually based on entangled networks, Bayesian networks or neural networks. Any of these are difficult or even impossible to implement and update in a manner compatible with an efficient, real-time and computer-implemented diagnostic method.

Another complicating aspect of prior art computer-implemented diagnostic approaches has to do with the way in which clinical data are treated. Clinical data, especially subjective symptoms, typically have diverse and non-exclusive qualities. For example, angina pectoris typically is retrosternal, radiating to the neck, jaw, upper extremities; it is oppressive, lasting only a few minutes; it is exertion related and is relieved by nitroglycerine. A number of prior art methods confer values to these qualities, their chronology, and their evolution. This is correct when such qualities are in overwhelming support of a diagnosis. Nevertheless, the algorithmic handling these subjective qualities vastly complicates the diagnostic method, and, under many circumstances, is detrimental rather than beneficial to its overall efficacy.

Still another factor encumbering prior art computer-implemented medical diagnostics is related to the prevalence of diseases. Prevalence statistics are of epidemiological importance. However, it may be harmful to include prevalence values when calculating the probability of a patient having a rare disease. This happens because the small prevalence value for such a rare disease can considerably reduce the probability of the corresponding diagnosis, causing it to be improperly ruled out. If a patient has a disease afflicting only one in a million persons, the probability of that diagnosis would be very small, but for him or her it represents one hundred percent. A perfect program should diagnose every possible disease, including those that are rare. Furthermore, accurate epidemiological information is difficult to obtain because many disease cases remain unreported. Moreover, representing prior probabilities of diseases also introduces considerable mathematical complexity to probabilistic computations and the Bayes formula. In order to manage this complication rare diseases are commonly excluded from the list of candidate diseases for diagnosis. This, once again, has the obvious negative consequence of the system being unable to diagnose patients afflicted with such rare diseases.

Given the numerous limitations of prior art medical diagnostic methods and corresponding computer-based systems, it would be an advance in the art to provide a method and system that embody a more constructive and fruitful approach. Specifically, it is highly desirable to devise a computer-implemented method that can better address the limitations listed above and be a more effective and efficient diagnostic companion for physicians and health care professionals.

OBJECTS AND ADVANTAGES

In view of the above prior art limitations and deeply felt needs in the health care community, it is an object of the invention to provide a computer-implemented method and system for practicing medical analytics. Among the primary goals of the method and system is to simplify the probabilistic determinations and to specifically circumvent the restrictive nature of the Bayes formula, which demands that clinical data manifested by the patient be independent, exhaustive and incompatible. More precisely, it is an object of the present invention to introduce a mini-max procedure for evaluating probabilities of diagnoses in a manner that overcomes the limitations of the Bayes formula and follows more closely the reasoning of a human health care provider such as a physician.

As part of the above primary goal, it is an objective of the invention to make the probabilistic determinations underpinning the mini-max procedure simple to implement and more useful at the same time. This is achieved partly by eliminating subjective qualities of clinical data, as these are hard to quantify and process. Further, disease prevalence is dismissed and all diseases are treated as if they had the same probability of occurrence. Omitting prevalence not only reduces complexity, but also ensures that common as well as rare diseases can be diagnosed by the method.

It is another objective of the invention to devise a system and a corresponding computer-implemented medical analytics method that associates proper risk and interaction identifiers to avoid overlooking important diagnoses or getting distracted by ultimately unimportant diagnoses.

Still another objective of the invention is to provide a method for assessing the full cost of investigating a clinical datum. Based thereon, the medical analytics method should make it possible to recommend a best cost-benefit clinical datum to investigate next in a patient while precluding search for low-priority or irrelevant clinical data. This can be done by simultaneously recommending a number of these best cost-benefit clinical data to investigate next.

Yet another objective of the present invention, is to enable a transparent and rational presentation of concurrent diagnoses, complex clinical data presentations and interactions between concurrent diseases or drugs that may mask important clinical data of the primary disease and more. Specifically, it is envisaged that the medical analytics method of the invention distinguish competing diagnoses from concurrent diagnoses.

In general, the method and system of invention intend to significantly reduce the current numerous diagnostic errors and their consequences. Furthermore, they are aimed at saving specialist consultations, which is important in emergencies and in underdeveloped areas where specialists are not available. While achieving these advantages, the method and system of invention should further facilitate utilization reviews by hospitals, laboratories and other providers.

Another objective of the invention is to enable further progress in the computerization of medical analytics and to provide incentives for much needed universal electronic storage of medical records.

It is important to realize that the above objects and advantages represent merely a subset of the numerous objects and advantages. These and many further objects and advantages of the invention will become apparent upon reading the ensuing description.

SUMMARY OF THE INVENTION

The objects and advantages of the invention are secured by a novel medical analytics method that is implemented on a computer and is designed to diagnose one or more diseases (i) afflicting a patient. The method is based on using clinical data (m) that excludes subjective qualities of clinical data (m) and also excludes prevalence of the one or more diseases (i). The method calls for compiling a knowledge base that contains disease (i) models exhibiting clinical data (m) and for inputting clinical data present (j) in the patient into the computer. In a subsequent step, clinical data present (j) are matched with clinical data (m) in the knowledge base to enable the computer to compose a differential diagnosis list of ruled in diagnoses (k), where k=1 . . . n, for each of the disease (i) models that links to or exhibits at least one clinical datum (m) that matches at least one clinical datum present (j) in the patient. In another step, the computer computes a probability P(k) for each of the ruled in diagnoses (k) with the aid of a mini-max procedure.

The mini-max procedure is itself broken down into several steps. In one step, the computer obtains sensitivities $S(i)_m$ of each of the clinical data (m) for each of the diseases (i) based on models of those diseases (i) built up from historical information. The historical information is captured by a total number of sample cases of a given disease (i) and the number of those disease (i) cases that manifest a particular clinical datum (m). Thus, sensitivities $S(i)_m$ are expressed as follows:

$$S(i)_m = \frac{\text{number of disease}(i) \text{ cases manifesting clinical datum}(m)}{\text{total number of disease}(i) \text{ cases}}.$$

In another step, the computer computes positive predictive values $PP(k)_j$ of each clinical datum present (j) for each ruled in diagnosis (k) as follows:

$$PP(k)_j = \frac{S(k)_j}{S(1)_j + \ldots + S(k)_j + \ldots + S(n)_j}.$$

Here $S(k)_j$ are sensitivities of clinical data present (j) to diagnoses (k), and n is the number of ruled in diagnoses (k). Next, the mini-max procedure calls for assigning as probability P(k) of each corresponding diagnosis (k) the maximum value among the positive predictive values $PP(k)_1$, through $PP(k)_z$:

$$P(k) = \max(PP(k)_1, PP(k)_2, \ldots, PP(k)_z),$$

where z is the number of clinical data present (j). Once the above steps are completed and the mini-max procedure applied, the differential diagnosis list and the probability P(k) for each diagnosis (k) are displayed by the computer on a suitable display. A human user, such as a physician, a clinician or a health care provider can then use the information displayed in this manner for medical analytics and other purposes.

The mini-max procedure extends to additional steps and aspects of medical analytics. Specifically, the method further includes creating clinical data pairs (j, r). This is done by selecting one of the clinical data present (j) and one of the clinical data absent (r) in the patient. Now, the clinical data pair (j, r) combines the one of the clinical data present (j) and the one of the clinical data absent (r). This pair is then used to compute a partial probability $P(k)_{j,r}$ of diagnosis (k) given clinical data pair (j, r). The calculation is performed as follows:

$$\text{partial } P(k)_{j,r} = \frac{PP(k)_j(1-S(k)_r)}{PP(1)_j(1-S(1)_r) + \ldots PP(k)_j(1-S(k)_r) + \ldots PP(n)_j(1-S(n)_r)},$$

where n is the number of ruled in diagnoses (k), as already pointed out above. All possible clinical data pairs must be created with all clinical data present and clinical data absent, with their corresponding partial probability $P(k)_{j,r}$ and for each diagnosis (k).

To make the method easier to implement and oversee by a physician or other human user, it is convenient to present clinical data pairs (j, r) in corresponding clinical data pair tables. In addition to providing an intuitive presentation, these tables illustrate an important normalization aspect of the mini-max procedure. Namely, as additional clinical data pairs (j, r) are created the method of invention ensures that the sum of partial probabilities $P(k)_{j,r}$ for each of the ruled in diagnoses (k) remains one. Thus, for every specific clinical data pair (j, r) we have $P(1)_{j,r} + \ldots P(k)_{j,r} + \ldots P(n)_{j,r} = 1$, or, expressed in standard summation convention:

$$\sum_{k=1}^{n} P(k)_{j,r} = 1.$$

The mini-max procedure portion of the method of invention further calls for creating a mini-max table for each of the diagnoses (k) in the differential diagnosis list. In doing so, a first data column of each mini-max table lists the positive predictive values $PP(k)_j$ of clinical data present (j) in the patient for diagnosis (k) considered in the particular mini-max table. For clarity of presentation to a human user, e.g., the physician, the very first column, which conveniently precedes the first data column of the mini-max table, can list the names of clinical data present (j). A first row of each mini-max table lists the names and sensitivities $S(k)_r$ of the clinical data absent (r) in the patient for diagnosis (k) for which the mini-max table was created.

Mini-max tables are intended to help obtain the total probabilities TP(k) of corresponding diagnoses (k). To achieve this goal, the instructions for creating them further involve: a) transferring each partial probability $P(k)_{j,r}$ into cells of the mini-max table where the $PP(k)_j$ value for each clinical datum present (j) and the sensitivity $S(k)_r$ of each clinical datum absent (r) converge; and b) selecting from among the partial probabilities $P(k)_{j,r}$ in the cells a determining partial probability $DP(k)_{j,r}$ that is at the same time the smallest value in its row and the greatest value in its column. At this point, the determining probability $DP(k)_{j,r}$ is selected as the total probability TP(k) for the diagnosis (k) for which the mini-max table in question was created.

In a practical diagnostic quest, it is necessary to establish some criteria for confirming and ruling out diagnoses (k) on the differential diagnosis list. In accordance with the method of invention, a diagnosis (k) is confirmed as a final diagnosis (k) when its total probability TP(k) is greater than a confirmation threshold value CT. Similarly, a diagnosis (k) is deleted or ruled out when its total probability TP(k) is smaller than a deletion threshold DT. Under normal circumstances, the numerical values of CT and DT are determined empirically. Once all of the diagnoses (k) in the differential diagnosis list have satisfied either the confirmation threshold CT or the deletion threshold DT the method can be stopped.

The method and system of invention build on the mini-max procedure to further improve medical analytics by recommending a best cost-benefit clinical datum (m) to investigate next in the patient. This is done in steps by first selecting in disease (i) models stored in the knowledge base and corresponding to the diagnoses (k) that have been ruled in into the differential diagnosis list, all clinical data not yet investigated (y) in the patient. These data, of course, are taken from among the clinical data (m) that belong to disease (i) models. In the next step a cost C(y) of collecting that clinical datum not yet investigated (y) is computed as follows:

$$C(y) = \max(\text{expense}(y), \text{risk}(y), \text{discomfort}(y)),$$

where cost C(y) is taken to be the maximum value from among the expense, risk and discomfort of obtaining the clinical datum not yet investigated (y) for that patient. Even before collecting this clinical datum not yet investigated (y), the method preferably computes a total probability TP(k) for each of the diagnoses (k) ruled in into the differential diagnosis list under inclusion of each of the clinical data not yet investigated (y) into the mini-max procedure. To accomplish this, the clinical data not yet investigated (y) are considered from two perspectives: they are treated as if found present in the patient in one calculation of TP(k), and they are also treated as if found absent in the patient in another calculation of TP(k).

In accordance with the preferred embodiment of the method, each clinical datum not yet investigated (y) is selected to best balance the cost C(y) of obtaining it against its change to total probability TP(k). In other words, the clinical datum not yet investigated (y) is chosen so as to minimize cost C(y) and maximize the change in magnitude of total probability TP(k) for corresponding diagnosis (k) if actually found present (j) or absent (r). Clearly, this approach can be extended to dealing with a number of clinical data not yet investigated (y) in the patient while balancing cost C(y) against the benefit expressed in terms of maximizing the change of magnitude of the total probabilities TP(k) for corresponding diseases (k). As before, this balance between cost and benefit is ensured by computing a total probability TP(k) for each of the diagnoses (k) ruled in into the differential diagnosis list while first treating the clinical data not yet investigated (y) as if they were present and then as if they were absent.

In addition to the core method built around the mini-max procedure, many additional principles to make recommendations of best cost-benefit clinical data to investigate next, easy to implement, are also included. For example, the method further calls for determining whether the absence of any clinical datum among clinical data (m) will decrease a total probability TP(k) of the corresponding diagnosis (k). The mini-max procedure for that clinical datum (m) is aborted if the absence of such clinical datum (m) does not decrease the total probability TP(k).

The medical analytics method of the invention also addresses cases in which patient is afflicted by two or more concurrent diseases (i). This is accomplished by distinguishing competitive diagnoses (k) from concurrent diagnoses (k) and applying this distinction to diagnoses (k) ruled in into the differential diagnosis list. Further, diagnosing complex clinical presentations is also supported by the creation of complex clinical presentation models that list all potentially related diagnoses (k). If one confirmed diagnosis matches any of the potentially related diagnoses, then all the potentially related diagnoses (k) are transferred to the differential diagnosis list for processing.

Checking for interactions between drugs having the potential of masking any clinical data (m) that belongs to a primary disease (i) is enabled through flagging all disease (i) models in the knowledge base that include at least one clinical datum (m) susceptible to being masked by the drugs. The next step calls for listing for disease (i) models all the drugs and concurrent diagnoses (k) having the potential of masking any of the clinical data (m) belonging to the primary disease (i). The physician can then confirm the presence of any of the drugs in the patient. Once confirmed, the algorithm implementing the medical analytics method of the invention will remove any clinical datum (m) masked by the drugs from consideration if at least one of these drugs was confirmed present.

Checking for interactions between concurrent diseases (k) having the potential of masking any of clinical data (m) belonging to a primary disease (i) is also accomplished with the aid of flagging. Specifically, all disease (i) models in the knowledge base that include at least one clinical datum (m) susceptible to being masked by concurrent diseases (i) are flagged. The algorithm then lists for these disease (i) models all the concurrent diseases (i) that have the potential of masking any of the clinical data (m) belonging to the primary disease (i). Once presence of any of the concurrent diseases (i) is confirmed in the patient, any clinical datum (m) masked is removed from the corresponding disease (i) that contains that clinical datum (m) in its disease (i) model.

Of course, the method and system of invention can be embodied in many different ways. The above summary only touches upon a few salient aspects of the method and system. A detailed description of the preferred embodiments of the invention presented below in reference to the appended drawing figures will elucidate these embodiments and extensions thereof.

BRIEF DESCRIPTION OF THE DRAWING FIGURES

Figure 1:
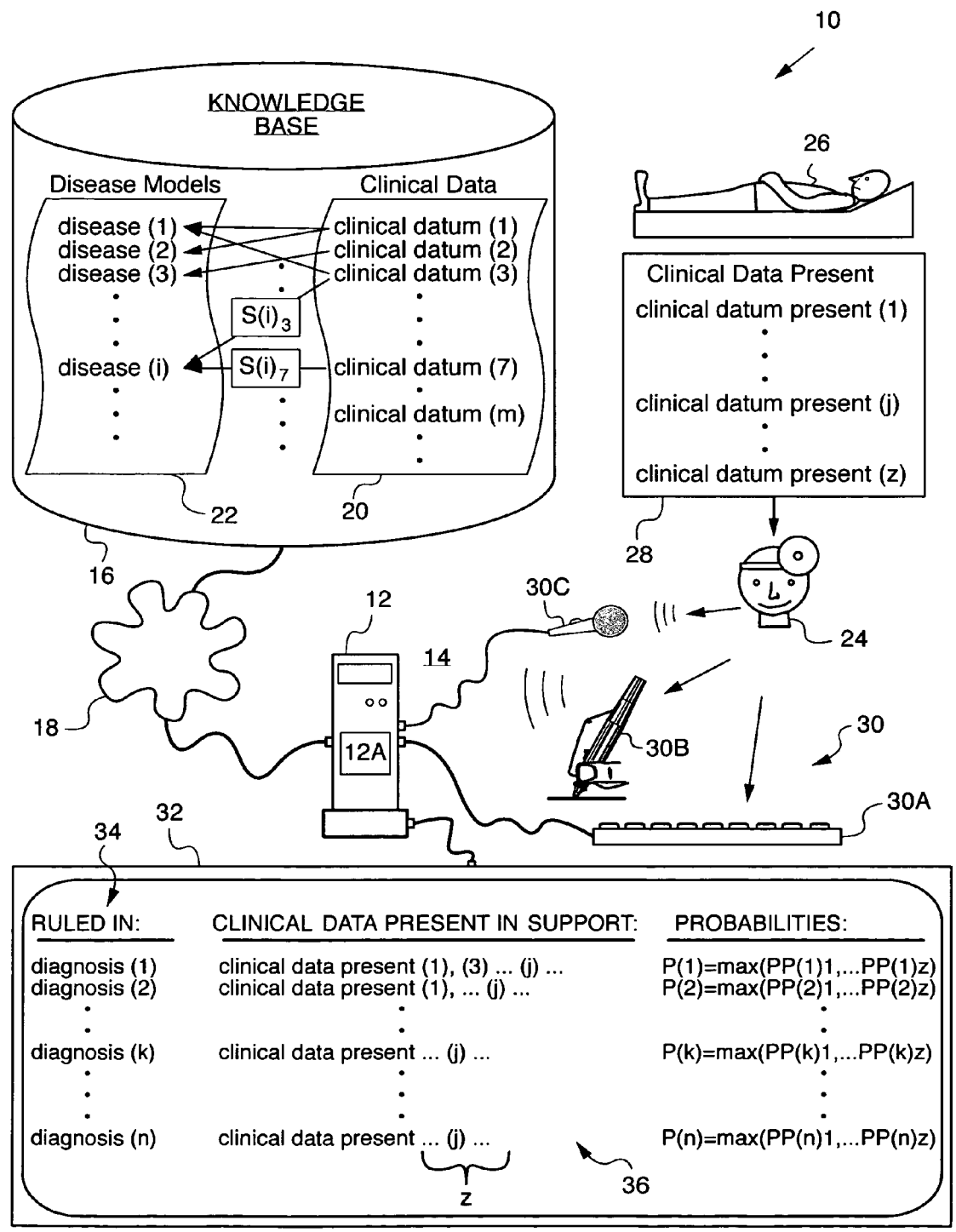
FIG. 1 is a schematic diagram illustrating a system for implementing the medical analytics algorithm according to the method of invention.
Figures 3, 4I:
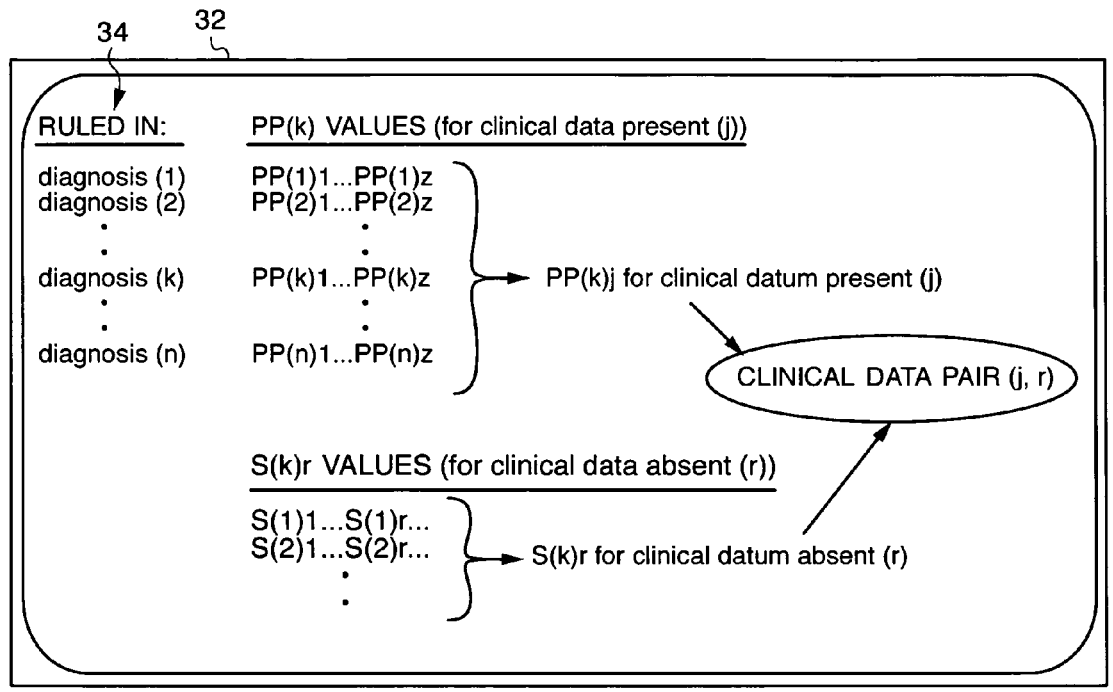
FIG. 3 is a schematic diagram illustrating the creation of a clinical data pair according to the invention.

FIGS. 4I-IV are exemplary mini-max tables for four diagnoses (k) shown on the display of the system of FIG. 1.

Figure 5:
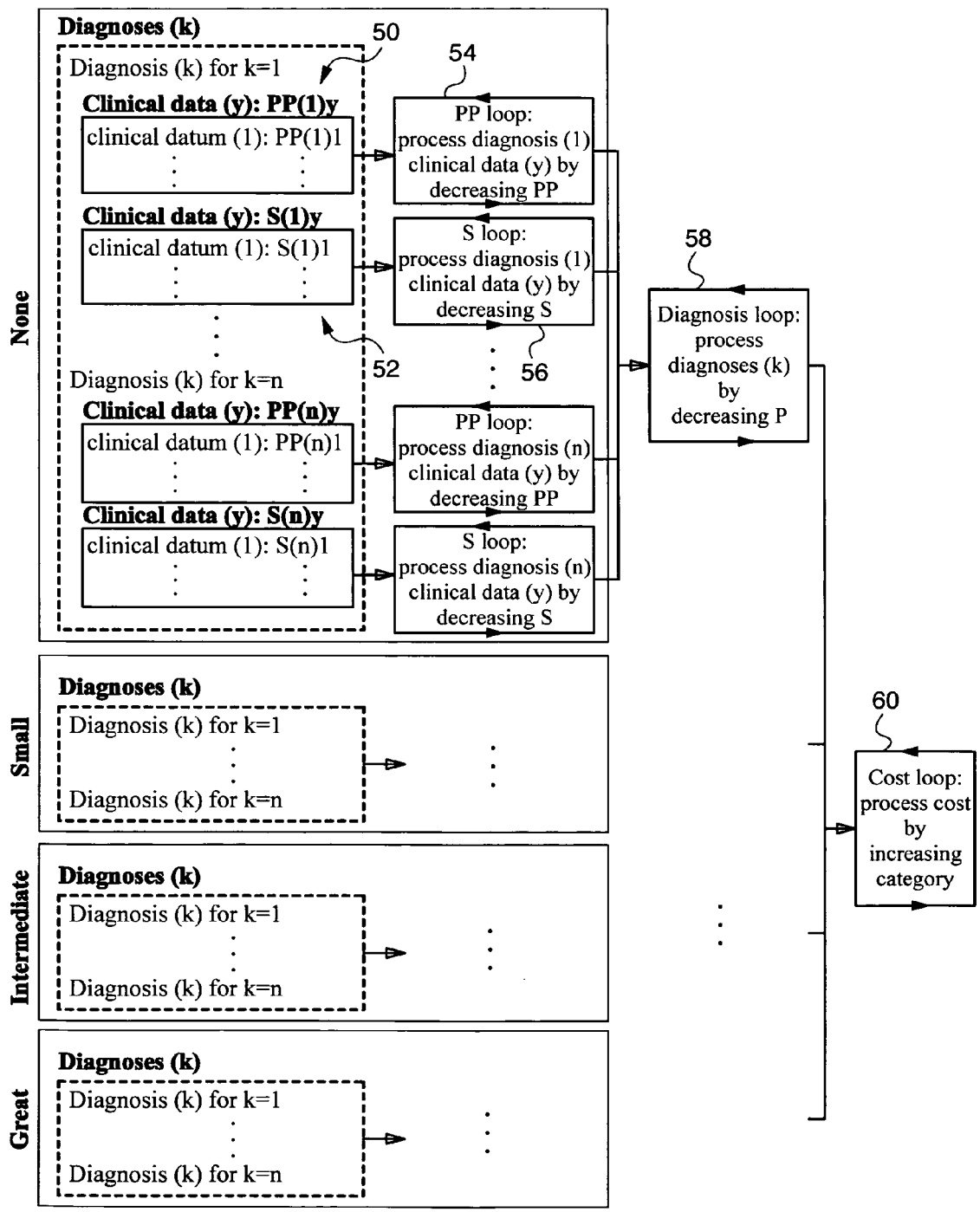

FIG. 5 is a diagram showing an advantageous hierarchical arrangement of data employed in deriving a recommendation of the best-cost benefit clinical datum to investigate next.

FIG. 6A-C are the exemplary mini-max tables updated and expanded during the 3-step method employed in conjunction with recommending the best cost-benefit clinical datum to investigate next.

Figure 7:
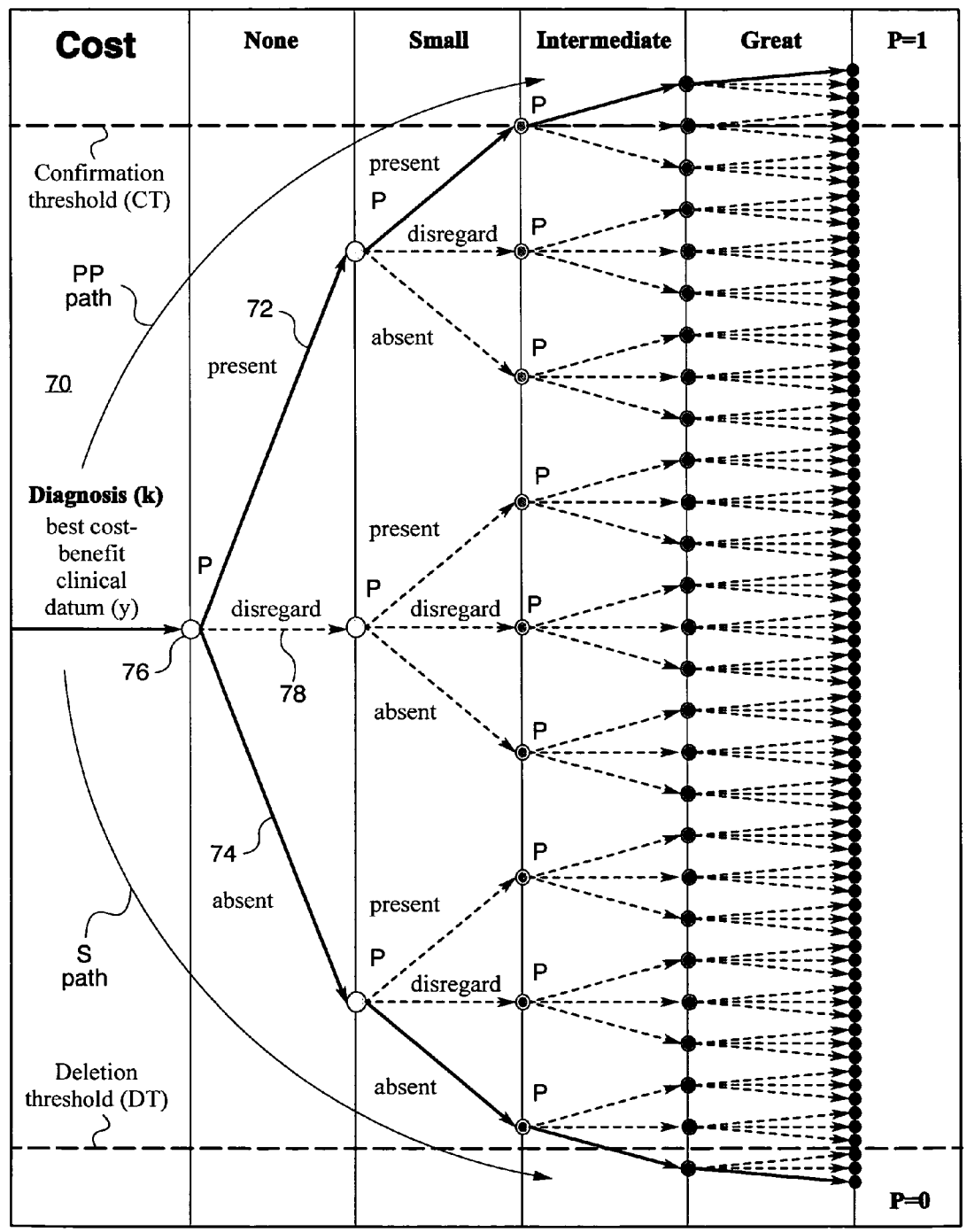

FIG. 7 is a trichotomy tree illustrating the process by which the medical analytics method recommends several best cost-benefit clinical data to investigate simultaneously.

FIGS. 8A-E are Venn diagrams depicting non-overlapping and overlapping relationships between clinical data (m) and corresponding diagnoses (k).

Figure 9:
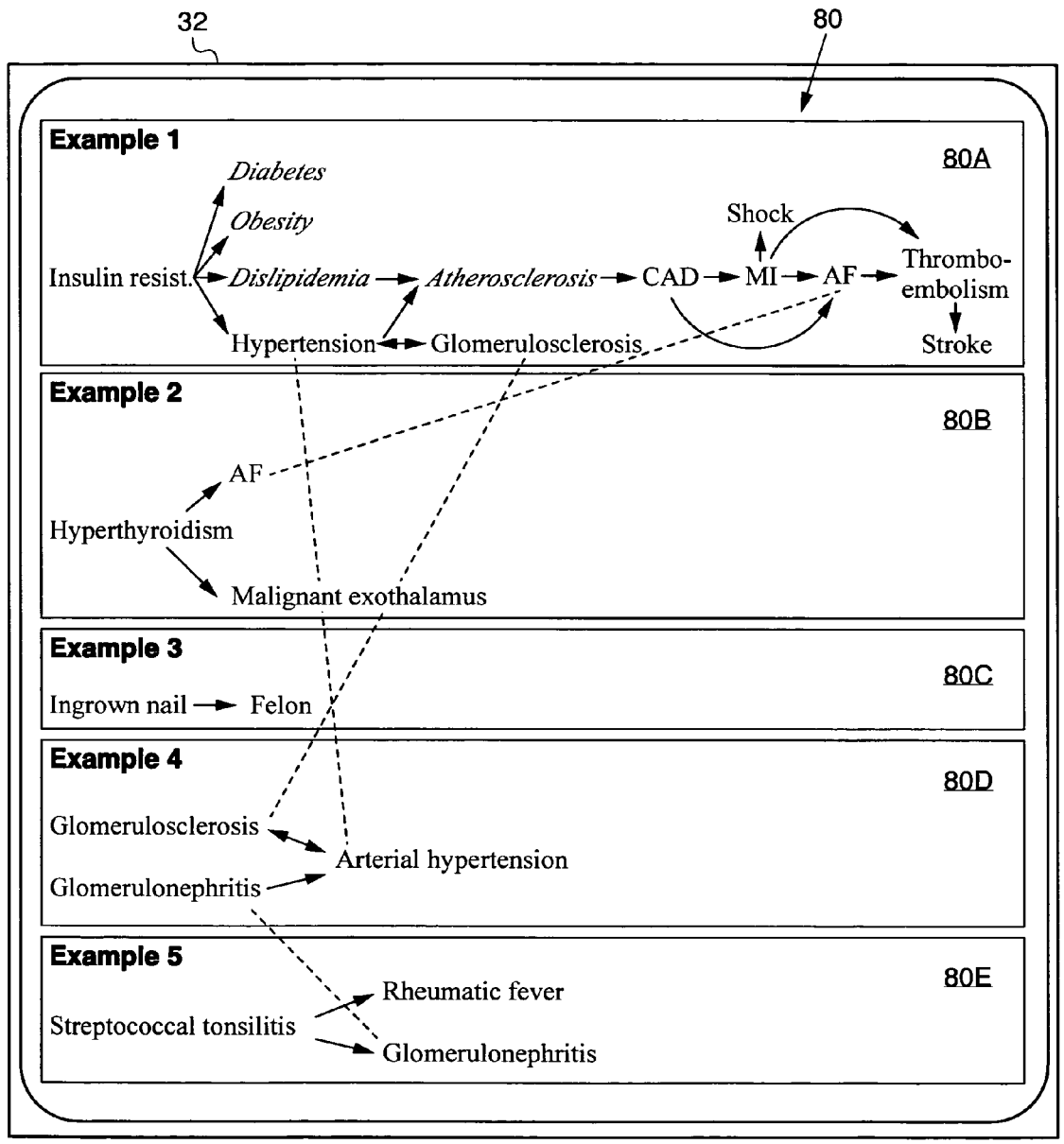

FIG. 9 is a diagrammatic representation of a complex clinical presentation model including diagnoses related causally or by statistical correlation, as displayed by the computer belonging to the system of FIG. 1.

FIGS. 10-28 are interrelated flow diagrams illustrating a preferred structure of the algorithm implementing the medical analytics method on the computer of the system shown in FIG. 1.

DETAILED DESCRIPTION

In contrast with prior art approaches, which are predominantly based on Bayes formula, entangled networks, Bayesian networks and neural networks, the present medical analytics method adopts a very straightforward mathematical perspective. Specifically, subjective qualities of clinical data as well as disease prevalence are disregarded. The probability calculations are thus vastly simplified, yet the clinical data collected from the patient is effectively matched with diverse kinds of models, including disease models and complex clinical presentation models.

Due to the many aspects of the present invention and in order to better teach a person skilled in the art, the detailed description will be broken down into sections. The first sections focus on defining terms and explaining the theoretical underpinnings of the medical analytics method and the basics of the mini-max procedure it employs. The latter sections are directed to a complete explanation of more advanced aspects of the method and the complete mini-max procedure. Finally, the last sections present examples to educate the practitioner about practical implementations.

Medical Concepts and Terminology

The history of medical terminology is long and nuanced. Therefore, it is important to define the terms employed throughout the application. The need to do so is rendered especially acute by the lack of consensus and incompleteness of definitions postulated in medical dictionaries and found in medical practice.

Disease is a condition in which physicochemical parameter values are out of range and health qualities, such as well-being, harmony in all body functions, and the ability to establish and fulfill goals in life, are altered; in other words, a malfunctioning of the organism. It typically leads to structural changes or lesions.

Etiology is the discipline that studies the causes of diseases; sometimes, the term is used as a synonym for cause of a specific disease.

Pathogenesis is the mechanism by which the cause of a disease produces lesions.

Pathophysiology is the study of the mechanisms by which a lesion causes abnormal function. Abnormal functioning is evidenced by three types of clues:

1. Symptoms, in the strict medical sense, are subjective clues (e.g., pain, nausea, vertigo) that the patient experiences. These clues are revealed by the patient during history taking.
2. Signs are objective clues (e.g., jaundice, swelling, wheezing) that a clinician detects during steps of the physical examination: inspection (observing the patient); palpation (feeling the shape, temperature, consistency, tenderness of organs); percussion (tapping and listening to the elicited sound); auscultation (listening to sounds produced by organs); and other maneuvers. A patient may or may not be aware of his or her signs.
3. Results of tests, studies, or procedures are clues obtained through laboratory tests, electrocardiograms, X-ray images, computed tomograms, sonograms, endoscopies, and other techniques.

Various synonyms (data, features, manifestations, traits, attributes, findings) are given to these clues that encompass symptoms, signs, and results of tests, studies, and procedures. Throughout this description the term clinical datum (pl. clinical data) will be used to refer to any of these clues. Clinical data tend to cluster into characteristic patterns called syndromes ("running together"). The clinical data that a syndrome comprises typically result from pathophysiologic mechanisms that originate in a common lesion. From the clinical data, tracing back these mechanisms leads to the diagnosis of the lesion.

Concurrent diseases are those that simultaneously afflict a single patient. They are unrelated concurrent diseases, when the concurrence is random and one disease is completely independent from the other. They are related concurrent diseases, when dependence exists.

Complication is a secondary disease or medical condition that is a consequence of a primary disease. Typically, a lesion of the primary disease conditions the action of a secondary cause producing the complication. Example: an ingrown nail (primary disease) that provokes a wound (primary lesion), which allows the entry of bacteria (secondary or added cause) provoking infection (secondary disease, which is the complication of the primary disease).

A specific disease may reveal diverse clinical pictures involving combinations of clinical data, syndromes, or complications. This diversity is referred to by several terms such as clinical form, clinical presentation, stage, or degree.

Clinical form: one of the diverse constellations of clinical data manifested, resulting from a single cause or type of lesion. An acute form, displays symptoms that appear suddenly and briefly evolve toward a cure, chronicity, or death (e.g., viral hepatitis.) A chronic form has a protracted course (e.g., rheumatoid arthritis.) Some forms depend on lesion localization (e.g., pulmonary, intestinal, renal, or genital tuberculosis.) Other forms depend on lesion characteristics (e.g., fibrotic, caseous, miliary, or cavitary tuberculosis.)

Complex clinical presentation is reserved for cases where two or more final diagnoses are needed to account for all manifested clinical data. For example, coronary artery disease, acute myocardial infarction, congestive heart failure, shock, and thromboembolism in a single patient.

Stage refers to the change of clinical data a disease presents over time. An example is syphilis that progresses through 3 stages, each with totally different syndromes that appear as if they pertain to unrelated diseases.

Degree refers to severity and often is related to duration and progression (stage) of the disease. Examples are congestive heart failure degrees I, II, III, and IV.

Clinical entity: a generic term for any element of a complex clinical presentation, such as a cause, lesion, syndrome, complication, disease, clinical form, stage, or degree.

Disease model or model of disease is an abstract concept subsuming all clinical data manifested by all patients with a specific disease. A patient typically never manifests all clinical data that his disease potentially can provoke. Integration of a specific disease model with all of its possible manifestations requires the statistical study of a large patient population. Each clinical form, stage, and degree of disease has its own disease model. Because health, death, and iatrogenic diseases are diagnoses that must be established clinically, the corresponding disease models must also be created.

Clinical data pertinent to a disease model can be collected either retrospectively or prospectively. Retrospectively, by reviewing medical records of past cases, journal articles, medical texts, etc. Prospectively, by accumulating clinical data from new cases; over time, the clinical data set will grow by apposition. This is related to the concept of "learning computers", where the computer gradually "learns" the disease, as the model is progressively refined.

In addition to its primary diagnostic purpose to enable sorting out all the diseases that can explain a given clinical datum, disease models also can provide the reciprocal information, listing all the clinical data that a given disease potentially can manifest. Disease models will be useful for study or research, if links to related medical information such as etiology, pathogenesis, pathology, pathophysiology, complications, prognosis, and treatment are created. All disease models are stored in the knowledge base introduced in the next section.

Diagnosis is the identification of an abnormal condition that afflicts a patient, based on manifested clinical data. Any diagnostic algorithm conceived is likely to be based on disease models stored in the computer knowledge base or in the physician's memory. Then, all available information from a specific patient is collected and compared with all disease models. When a successful match between the patient's clinical data and those included in a disease model is achieved, the patient's disease has been diagnosed. This interpretation is related to pattern recognition and is one way in which the human mind solves the diagnostic problem; artificial intelligence emulates this process with computers.

In the context of the present application, diagnosis means probability of disease. This definition refers properly to potential diagnosis; whereas the dictionary definition—the identification of an abnormal condition that affects a specific patient, based on manifested clinical data—is what is herein referred to as a final diagnosis or confirmed diagnosis. Unless otherwise qualified, diagnosis will denote potential diagnosis.

It is crucial to note, that the terms disease and diagnosis are sometimes wrongly interchanged: for example pneumonia disease for pneumonia diagnosis and vice versa. A disease is a change in the patient's body, whereas a diagnosis is a physician's mental construct.

Contradicting diseases (e.g., hyperthyroidism and hypothyroidism) cannot coexist in a given patient, but these two diagnoses could conceivably exist in the same differential diagnosis list, but with different probabilities, because both diseases may share certain symptoms (e.g., pretibial edema.) This confusion leads some computer program researchers to wrongly eliminate one of these apparently contradicting diagnoses from the differential diagnosis list.

Disease prevalence or prevalence of disease is the fraction of a population afflicted by a specific disease at a specific time. It also can be interpreted as the likelihood of a person belonging to that population to be afflicted by that disease.

Basic Theoretical Underpinnings

This invention presents a novel medical analytics method that can be used by physicians, clinicians, health care providers and other users as an aid in diagnosing diseases afflicting patients. FIG. 1 illustrates the most general aspects of a medical analytics system 10 that can be used to practice the invention in the form of an overall schematic diagram. System 10 has a computer 12 for implementing the algorithm at a hospital, clinic, or offices 14 of a physician or health care provider 24. Computer 12 is connected to a knowledge base 16 that is preferably stored off-site and updated with most recent medical information. In the present embodiment, knowledge base 16 is accessed by computer 12 via a network 18, such as the internet, a closed network or a suitable server network. Of course, a person skilled in the art will recognize that other interconnection architectures are possible. Alternatively, given a sufficiently powerful computer 12, knowledge base 16 could even be stored locally in the memory belonging to computer 12.

In contrast to prior art algorithms and systems, system 10 uses clinical data (m) in its clinical data files 20 that exclude subjective qualities. In addition, system 10 also excludes any reference to the prevalence of diseases (i) listed in its disease model files 22. For the purposes of this application indices (i) and (m) are used to uniquely and clearly label all corresponding diseases and clinical data. Each distinct value of index (i), e.g., i=17, corresponds to a specific disease (17). Similarly, each distinct value of index (m), e.g., m=23, corresponds to a unique clinical datum (23). This manner of indexing allows for unambiguous reference to specific data as well as aggregate data and will be applied throughout this application.

Clinical data (m) terms must be recognized and accepted by the algorithm and properly stored in files 20 of knowledge base 16. A given clinical datum (m) can be referred to by different synonyms (e.g., shortness of breath, dyspnea, or respiratory distress.) Standard terms for clinical data (m), for example Medical Subject Headings (MeSH) or Systematized Nomenclature of Medicine (SNOMED) are preferred, but if a synonym is used, the algorithm must be able to translate it into an acceptable standard term. When this happens, user 24 is notified; if no match is found, he or she is prompted to try another synonym. This synonym problem is addressed in the RECONSIDER program (Blois, et al, 1981); the idea of recognizing synonyms is not novel, but the manner in which the present algorithm addresses it is novel, as will be explained below.

Knowledge base 16 is compiled in such a way that disease (i) model files 22 and clinical data (m) files 20 are linked. This is accomplished by using indices and identifiers for clinical data (m). In knowledge base 16 there are three indices associated with each clinical datum (m), namely: sensitivity S, positive predictive value PP and cost C. Note that hereafter positive predictive value PP is also referred to as PP value or simply PP. Also, knowledge base 16 has two identifiers associated with selected clinical data (m): risk and interaction identifiers. All of these indices and identifiers will be explained in more detail below.

At this point it is important to note that diseases (i) contained in disease model files 22 are linked to clinical data (m) that are exhibited by the corresponding diseases (i). The relationships or mappings between diseases (i) and clinical data (m) are based on actual cases of diseases (i) or historical data. Clearly, more than one of diseases (i) may manifest a particular clinical datum (m). Similarly, any given disease (i) may be linked to any number of clinical data (m) that it manifests. Preferably, knowledge base 16 is continuously updated as new information about cases of known diseases (i) and clinical data (m) becomes available to the health profession.

A health care provider such as physician 24 obtains clinical data present (j) in an actual patient 26 in any known manner. For example, physician 24 may examine patient 26 directly, or they may access a case history file 28 of patient 26. Clinical data present (j) is also indexed and in the particular case shown in FIG. 1, it ranges from j=1 to j=z; or simply stated: j=1 . . . z. Of course, the number of clinical data present (j) may also be just one (j=1) at the time of initial consultation or visit of patient 26 with physician 24.

In addition to being connected with knowledge base 16 via network 18, computer 12 has an input interface 30, which can include a keyboard, a mouse, a digital tablet or a digital pen. In the present case physician 24 uses a keyboard 30A, a digital pen 30B and a voice system with a microphone 30C as parts of input interface 30. Depending on the manner of collecting clinical data present (j), physician 24 may check them off with digital pen 30B linked wirelessly to computer 12, enter them into computer 12 via a wired keyboard 30A during the course of examination of patient 26 or dictate them off-line using microphone 30C. Alternatively, some of clinical data present (j) may be uploaded directly if case history file 28 is in a suitable electronic format.

Once clinical data present (j) in patient 26 is available to computer 12, the medical analytics algorithm can perform its operations and display the results to physician 24 on a display 32. In the present embodiment, display 32 is a flat-screen monitor of sufficient active area to show complex results and large tables in particular. Of course, any suitable device for visual output to physician 24 may be used. Indeed, non-visual output (e.g., aural) is possible, but not preferred due to the complex nature of the data presentation, as will become apparent below.

The medical analytics algorithm of the invention is operating locally on computer 12 and specifically, it runs on computer processor 12A. Alternatively, it could be encoded by software executing anywhere on network 18 in a localized or distributed fashion. It will be appreciated by those skilled in the art that the exact method of implementation of the medical analytics algorithm should be adapted to system 10, volume of data, network rates and other well-known operating parameters that dictate the most efficient architecture. For the purposes of the present invention, when referring to the algorithm implementing the medical analytics method of invention it is described in an embodiment run by computer 12 on processor 12A, or simply on computer 12 for brevity.

According to the method of invention, medical analytics algorithm matches clinical data present (j) in patient 26 with clinical data (m) in knowledge base 16. In other words, each individual clinical datum present ( ) as ascertained by physician 24 is linked or matched with each corresponding clinical datum (m) contained in data files 20 of clinical data (m). Again, it should be noted that clinical data (m) corresponds to historical cases of diseases (i) observed and recorded in disease model files 22.

Matching of each clinical datum present (j) with a corresponding clinical datum (m) enables the medical analytics algorithm running on computer 12 to compose a differential diagnosis list 34 of ruled in diagnoses (k). Once again, diagnoses (k) are also indexed with their index k ranging from k=1 to k=n; or just k=1 ... n. Diagnoses (k) are included or ruled in into differential diagnosis list 34 for each disease (i) whose model as stored in file 22 links to or exhibits at least one clinical datum (m) as stored in file 20 that matches at least one clinical datum present (j) in patient 26.

Any specific clinical datum (m) is typically exhibited by several diseases (i). Thus, even a single clinical datum present (j), where j=1, will match a corresponding clinical datum (m) that usually links to a number of diseases (i). Any or even several of these diseases (i) may be afflicting patient 26. Hence, they are ruled in and added to differential diagnosis list 34 in the form of ruled in diagnoses (k) by the medical analytics algorithm. For example, files 20, 22 show a specific disease (1) linked to two different clinical data (1) and (3) (i.e., m=1, 3). Confirmation of either clinical datum (1) or clinical datum (3) among clinical data present (j) in patient 26 will cause the medical analytics algorithm to rule in a specific diagnosis (k) corresponding to disease (1) into differential diagnosis list 34.

Once all clinical data present G) in patient 26 are matched with corresponding clinical data (m) in file 20 and diagnoses (k) of diseases (i) exhibiting those clinical data (m) are ruled in into differential diagnosis list 34, the medical analytics algorithm running on computer 12 executes its core operations. During one of these core operations, computer 12 computes a probability P(k) for each one of ruled in diagnoses (k). The manner in which this operation is performed differs substantially from the prior art teachings and forms a part of a mini-max procedure introduced herein.

The mini-max procedure circumvents the restrictive nature of the Bayes formula, which is limited by the fact that it requires the clinical data manifested by a patient to be independent, and diagnoses to be exhaustive and incompatible. In prior art, clinical data values such as sensitivity, specificity, predictive value, weights, estimated values are added, subtracted, multiplied, averaged; or the Bayes formula is iterated with each additional clinical datum (m) to establish a total score or probability P(k) of diagnosis (k). These methods yield inaccurate results.

In contrast to prior art, the mini-max procedure computes the probability P(k) of diagnosis (k) by simultaneously processing clinical data present (j) that increase this probability, based on positive predictive value $PP(k)_j$ and clinical data absent that decrease this probability, based on sensitivity $S(i)_m$.

The mini-max procedure is broken down into several steps. In one step, computer 12 obtains sensitivities $S(i)_m$ of each of the clinical data (m) corresponding to disease (i) models, based on the historical information stored in knowledge base 16. Sensitivities $S(i)_m$ represent the first of the three indices associated with clinical data (m). To enable this indexing, disease model files 22 contain for each disease (i) a record of many prior instance of manifesting each particular clinical datum (m).

Differently stated, the historical information required to practice the medical analytics method of the invention is captured by a total number of sample cases of a given disease (i) and the number of those disease (i) cases that manifest a particular clinical datum (m). No record of the intensity of any clinical datum (m) or other subjective or tangential information is required by the method of the present invention. Also, no statistics about the prevalence of diseases (i) is included in files 22. The absence of both subjective qualities associated with clinical data (m) and prevalence information for diseases (i) as stored in files 20, 22 allows for smaller files 20, 22 and more efficient computations. The absence of these two parameters, frequently regarded as vital by prior art teachings and medical diagnostic systems is a very important distinguishing feature of the present medical analytics method.

The sensitivities $S(i)_m$ of manifested clinical data (m) for diseases (i) based on models of diseases (i) stored in knowledge base 16 are expressed as follows:

$$S(i)_m = \frac{\text{number of disease}(i) \text{ cases manifesting clinical datum}(m)}{\text{total number of disease}(i) \text{ cases}}. \quad (\text{Eq. 1})$$

Thus, sensitivity $S(i)_m$ is the statistically determined fraction of patients with a given disease (i) who manifest specific clinical datum (m) expressed as a decimal or percentage. For example, FIG. 1 shows for a specific disease (i) whose model is stored in file 22 with two sensitivities $S(i)_3$ and $S(i)_7$ indexing clinical data (m=3, 7) stored in file 20. Of course, any specific disease (i) is typically linked by sensitivities $S(i)_m$ to more than just two clinical data (m). However, this limited indexing is presented for pedagogical purposes and to help visualize how files 22 and 20 are linked in knowledge base 16 to efficiently encode the requisite historical information or information available from sample cases.

If the numerator and denominator of Eq. 1 are equal, then sensitivity $S(i)_m$ of clinical datum (m) for disease (i) will equal 1. This is unlikely, as it requires that all clinical cases of disease (i) so far reviewed manifested clinical datum (m). Otherwise, the numerator will always be smaller than the denominator and $S(i)_m$ will be less than 1. Every additional clinical case will increase $S(i)_m$ if clinical datum (m) is present, or reduce it if clinical datum (m) is absent.

To stay current, computer 12 recalculates sensitivity $S(i)_m$ of each clinical datum (m) each time knowledge base 16 is updated with new cases of disease (i). The greater the number of cases analyzed, the greater the accuracy of sensitivity $S(i)_m$. If a clinical datum (m) is never manifested by a specific disease (i), its sensitivity $S(i)_m$ equals 0 for this disease (i). When sufficient number of cases have been reviewed, the disease model will include all clinical data (m) that disease (i) can potentially manifest, and the sensitivities $S(i)_m$ will approach their true values.

A person skilled in the art will appreciate that in any practical embodiments it is preferable to pre-compute sensitivities $S(i)_m$. Such pre-computation can be performed locally by computer 12 or remotely by any processing device (not shown) of knowledge base 16 or other resource of network 18. These pre-computations are preferably made before physician 24 enters or approves clinical data present (j) to improve real-time performance of system 10.

In another step of the mini-max procedure, computer 12 computes the second of the three indices associated with clinical data (m), namely their positive predictive values PP. Positive predictive values PP indicate how strongly a clinical datum (m), if found as clinical datum present (j) in patient 26, supports a disease (i). In practicing the method of invention, we are particularly interested in how strongly a clinical datum present (j) supports each of the n number of ruled in diagnoses (k). In other words, we are interested in positive predictive values $PP(k)_j$ of clinical data present (j) for diagnoses (k) defined as follows:

$$PP(k)_j = \frac{S(k)_j}{S(1)_j + \ldots + S(k)_j + \ldots + S(n)_j}. \quad \text{(Eq. 2)}$$

Note that $PP(k)_j$ values are equivalent to $PP(i)_m$ values of clinical data (m) for diseases (i). The $PP(k)_j$ values can simply be picked out from among $PP(i)_m$ values stored in knowledge base 16 once clinical data present (j) and diagnoses (k) ruled in and included in differential diagnosis list 34 are known.

To elucidate some salient features of positive predictive values $PP(k)_j$, FIG. 1 illustrates clinical data present (j) organized in support of corresponding diagnoses (k) in a group list 36. Note that each clinical datum present (j) is likely listed many times on list 36 in support of several different diagnoses (k). For example, clinical datum present (j) being cough supports diagnoses (k) that include: tuberculosis, bronchitis, lung cancer, pneumonia and others. Sensitivities $S(k)_j$ of clinical data present (j) that do not support a ruled in diagnosis (k); e.g., clinical datum present (j) being cough does not support diagnosis (k) being myopia, end up making no contribution because their sensitivities $S(k)_j$ are zero.

Clinical data present (j) that do not support a diagnosis (k) due to zero sensitivity, $S(k)_j=0$, need not be placed on list 36. That is because the denominator in Eq. 2, namely $S(1)_j + \ldots + S(k)_j + \ldots + S(n)_j$, is evidently a sum of sensitivities $S(k)_j$ of a particular clinical datum present (j) for all possible diagnoses (k) ranging over $k=1 \ldots n$. Addition of sensitivity values equal to zero does not alter the sum. At the same time, placing a zero sensitivity, $S(k)_j=0$, in the numerator ensures that the corresponding positive predictive value $PP(k)_j$ will be zero irrespective of the value of the denominator.

To be efficient in the use of computer 12 and its computing resources, however, positive predictive values $PP(k)_j$ per Eq. 2 should be computed with just the non-zero sensitivities $S(k)_j$ of clinical data present (j) for diagnoses (k). In other words, only a number z of clinical data present (j) linked to each ruled in diagnosis (k) by a non-zero sensitivity value should be taken into account. This efficient approach and the z clinical data present (j) that should be used in the calculations are indicated in FIG. 1.

Just as in the case of sensitivities $S(i)_m$, it is possible and desirable to pre-compute positive predictive values $PP(i)_m$ for many or even all clinical data (m) in knowledge base 16 that can be found as clinical data present (j) in patient 26. Preferably, pre-calculated $PP(i)_m$ values are linked to corresponding clinical data (m) in disease (i) models stored in files 22 in knowledge base 16. Because $PP(i)_m$ values are based on statistically established sensitivities $S(i)_m$ stored in knowledge base 16, they do not depend on specific clinical cases. Therefore they can be calculated before medical analytics method is used by physician 24; i.e., before system 10 is actually placed into operation.

$PP(i)_m$ values remain fixed unless new disease (i) models are added to knowledge base 16 or revised statistics alter the values of sensitivities $S(i)_m$ upon which $PP(i)_m$ values are based. Should such changes occur as a result of an occasional update, all $PP(i)_m$ values must be re-calculated.

Thus, typical positive predictive values $PP(i)_m$, which represent the second index associated with each clinical datum (m), will be available before actual data present (j) are entered or confirmed by physician 24 and before corresponding diagnoses (k) are ruled in into differential diagnosis list 34. The actual pre-computation can be performed locally by computer 12 or remotely by any processing device (not shown) of knowledge base 16 or other resource of network 18.

From the above it is clear that $PP(k)_j$ values found for patient 26, and indeed all pre-computed $PP(i)_m$ values in knowledge base 16, are indeed distinct from sensitivities $S(i)_m$. Moreover, because the medical analytics method of the invention leaves out subjective qualities of clinical data (m) and prevalence of diseases (i), the resultant positive predictive values $PP(k)_j$ are defined differently and are numerically distinct from commonly accepted standard positive predictive values taught in the prior art.

A $PP(i)_m$ value is 1 when clinical datum (m) is manifested only by disease (i) under consideration (that is, when for all other diseases $S(i)_m=0$). Conversely, a $PP(i)_m$ value approaches zero (0) when clinical datum (m) is always manifested in all other diseases (i) (that is, when for all other diseases $S(i)_m=1$). In remaining situations, $PP(i)_m$ assumes an intermediate value between 0 and 1.

Any specific positive predictive value $PP(i)_m$ quantifies how characteristic or exclusive a clinical datum (m) is for a specific disease (i), or, equivalently, $PP(k)_j$ quantifies how exclusive a clinical datum present (j) is for a given diagnosis (k). According to Eq. 2, positive predictive value $PP(k)_j$ is influenced by the magnitude of the denominator. In turn, the magnitude of the denominator is influenced by both the number of sensitivity $S(i)_m$ terms and their individual magnitudes.

In terms of medical analytics, what this means is that the fewer the number of diseases (i) that manifest a given clinical datum (m) (number of S terms in the denominator), and the less often this clinical datum (m) is manifested by each of these diseases (i) (the smaller each S value in the denominator), the greater the $PP(i)_m$ value of the clinical datum (m) and the probability of the specific diagnosis (k) or disease (i). For example, the presence of *Mycobacterium tuberculosis* in sputum is pathognomonic of pulmonary tuberculosis because no other disease manifests this clinical datum; accordingly:

$$PP(\text{pulmonary tuberculosis})_{mycobacterium\ tuberculosis} = 1.$$

The present invention takes the position that $PP(k)_j$ is the most accurate index of how strongly a clinical datum present (j) supports a diagnosis (k).

For the medical analytics method to function properly, knowledge base 16 must include all currently known diseases (i). Should a disease (i) be omitted, its disease (i) model will not be created in files 22 and sensitivities $S(i)_m$ of the corresponding clinical data (m) will not be available and will miss from the denominator in Eq. 2. Consequently, the calculation of $PP(i)_m$ values of a clinical data (m) for any other disease (i) will be inaccurate. Still worse, the excluded disease (i) will never be included in differential diagnosis list 34. For this reason the entire medical analytics method can function properly only when models of all known diseases (i) are included in knowledge base 16.

It should be remarked, that Eq. 2 for calculating $PP(i)_m$ values of clinical data (m), derives from the Bayes formula, when prior probabilities are deleted. However, Eq. 2 does not violate the aforementioned condition or limitation of independent clinical data of Bayes formula, discussed in the background section. That is because all its terms refer to only one and the same clinical datum, although with different sensitivities for each diagnosis in its denominator. Eq. 2 can include in its denominator sensitivities $S(i)_m$ of all known diseases (i) capable of manifesting clinical datum (m). It is thus able to comply with the exhaustive condition. Because of the incompatible condition of the Bayes formula, the medical analytics method of the invention processes concurrent diseases (i) in a way that does not violate this condition, as explained later.

Returning to the actual steps of the method, once positive predictive values $PP(k)_j$ are available, the process can continue. In particular, equipped with these values, the mini-max procedure can now assign a single probability $P(k)$ to each ruled in diagnosis (k) in differential diagnosis list 34. Specifically, the mini-max procedure calls for assigning as probability $P(k)$ of each corresponding diagnosis (k) the maximum value among the positive predictive values $PP(k)_1$ through $PP(k)_z$, as follows:

$$P(k) = \max(PP(k)_1, PP(k)_2, \ldots, PP(k)_z). \quad \text{(Eq. 3)}$$

Since there are n diagnoses (k) on list 34, we obtain n corresponding probabilities $P(k)$.

After the above steps are completed and the above-described portion of mini-max procedure applied, differential diagnosis list 34 with probabilities $P(k)$ for each diagnosis (k) are displayed by computer 12 on display 32. Physician 24 can now use the information displayed for further medical analytics including a determination of directions for further investigation or treatment recommendations.

These initial steps of the present medical analytics method already present a significant advance over the prior art. For one, taking the maximum value among the positive predictive values $PP(k)_1$ through $PP(k)_z$ as probability $P(k)$ of diagnosis (k) avoids a common mathematical problem encountered in prior art diagnostic methods. Specifically, consider that many clinical data (m) are intimately related by a common cause or lesion. For example, clinical data (m) such as jaundice, dark urine and increased direct serum bilirubin are related by similar pathophysiologic mechanisms generated by a single lesion: biliary tract obstruction. Were we to arithmetically combine the several $PP(k)_j$ values of these three equivalent and "redundant" clinical data (m), the probability of diagnosis (k) being biliary tract obstruction would be improperly increased, thereby providing an undue advantage to this diagnosis, as compared to competing diagnoses. Additionally, if common bile duct-obstructing gallstones were revealed by endoscopic retrograde cholangiopancreatography (ERCP)—a clinical datum (m) that alone has a $PP(k)$ value of 1—then the probability $P(k)$ of diagnosis (k) being obstructing gallstones, if other supporting clinical data (m) were added, would exceed one (1). In standard probability theory this is mathematically impossible.

Thankfully, by taking just the greatest positive predictive value $PP(k)_j$ related to diagnosis (k) being gallstone obstruction as its probability $P(k)$ supersedes all other clinical data (m) with lesser $PP(k)_j$ values; i.e., jaundice, dark urine and increased serum bilirubin. That is because, whether present or absent, these three clinical data (m) would not change diagnosis (k) of obstructing gallstones already confirmed by ERCP. Differently put, taking the greatest of all positive predictive values $PP(k)_j$ for all clinical data present (j) that support diagnosis (k) as the probability $P(k)$ of that diagnosis (k) avoids serious incompatibilities with probability theory. Moreover, as discovered by the inventors, taking the maximum positive predictive value of clinical data supporting a diagnosis equal to the probability of that diagnosis is more rational, accurate and efficient than prior art scoring and Bayes methods.

So far, we have not yet processed clinical data absent in the patient, which will adversely affect or decrement the probability $P(k)$ of diagnoses (k). This aspect of the invention will be discussed at a later stage.

Before continuing, let us stress the fact that the present method justifies dismissal of subjective qualities of clinical data (m) for a number of reasons. First, qualities of clinical data (m) and chronology are subjective and widely variable. For example, chest pain of angina pectoris is sometimes mild, confined to the upper abdomen, not radiating, yet is burning, but may even be absent in patient 26 with diabetes. Accordingly, these subjective qualities may not be reliable. Anxious or hypochondriac patients can imagine such qualities. To confirm diagnosis (k) being angina pectoris, more reliable tests, such as stress ECG and even angiography are needed. These provide clinical data (m) with greater positive predictive values PP that will supersede the clinical datum present (j) being chest pain and having a smaller positive predictive value PP. Therefore, disregarding these unreliable qualities simplifies the diagnostic process without losing accuracy. Second, it would be difficult, if not impossible, to determine sensitivities $S(i)_m$ in Eq. 1 of each quality open to a patient's subjective interpretations given the thousands of known clinical data (m) and diseases (i) manifesting them.

Purposely disregarding prevalence of diseases (i) is doubly advantageous. First, prevalence, which is tantamount to prior probabilities of diseases (i), is eliminated from the Bayes formula. This reduces previously challenging mathematical expressions into the simple Eq. 2 for calculating positive predictive values $PP(k)_j$ from statistically established sensitivities $S(i)_m$ derived in Eq. 1. Second, marginally low prevalence values no longer justify excluding rare diseases (i) from differential diagnosis list 34. Thus, even infrequent diseases (i) can be included among diagnoses (k) to become a final diagnosis based on the merit of supporting clinical data (m).

Theory Behind the Mini-Max Procedure

In the preferred embodiment, the mini-max procedure extends beyond the basic steps discussed above. To restate succinctly, thus far the mini-max procedure computes the first two indices of clinical data (m): sensitivities $S(i)_m$ per Eq. 1 and positive predictive values $PP(i)_m$ per Eq. 2 (which then become $PP(k)_j$ for clinical data present (j) and diagnoses (k) placed in differential diagnosis list 34). The mini-max procedure also assigns probabilities $P(k)$ to ruled in diagnoses (k) in the differential diagnosis list 34. These probabilities $P(k)$ are the maximum values among positive predictive values $PP(k)_j$, of $PP(k)_1$ through $PP(k)_z$, with z being the number of clinical data present (j) that have a non-zero sensitivity $S(k)_j$ for the corresponding diagnosis (k) to which probability $P(k)$ is assigned (see Eq. 3).

To reduce the overall socioeconomic cost of diagnostic medicine and suffering of patients, the algorithm introduces a cost $C(m)$ for obtaining each clinical datum (m) in knowledge base 16. In fact, cost $C(m)$ represents the third index of clinical data (m).

Cost $C(m)$ in the context of this application, involves not only expense, but also risk and discomfort resulting from the required test or procedure. Expense is quantifiable in dollars or any other currency. Risk can be statistically quantified by outcomes of the procedure, although it also depends on operator skill. Discomfort is a subjective feeling that depends in part on the invasiveness of the procedure and in part on patient apprehension, although the latter can be controlled with sedation or anesthesia. Discomfort cannot be expressed as an exact numerical value, but only can be assigned an estimated qualitative level such as none, small, intermediate, or great. Expense, risk, and discomfort—like apples and oranges—cannot be arithmetically combined into an exact overall cost. Expense and risk, however, can be qualitatively expressed in levels similar to discomfort, to make the latter comparable to the former two. It is practical, and novel, to consider the maximal qualitative level of expense, risk, and discomfort, as representative of overall cost level for obtaining clinical datum (m):

$$C(m)=\max(\text{expense}(m), \text{risk}(m), \text{discomfort}(m)).$$

Because cost does not participate in the calculation of probability P(k) of diagnoses (k), its inexactness is not critical. This third index is considered only when selecting the most suitable clinical datum (m) to investigate next in patient 26.

Each clinical datum (m) is assigned one of four overall cost categories: no cost (clinical data typically obtained through medical history and physical examination), small cost (e.g., obtained through routine laboratory analysis, ECG, and other ancillary studies), intermediate cost (e.g., colonoscopy, lymph node excision biopsy), and great cost (e.g., liver biopsy, laparotomy.)

Cost C(m) must be compared to the benefit expected from acquiring clinical datum (m). Benefit has two components: a quantitative component and a qualitative component. The quantitative component depends on positive predictive value $PP(i)_m$ and sensitivity $S(i)_m$ of clinical datum (m) for disease (i), which in turn determine probabilities P(k) of corresponding diagnoses (k) in the manner explained above. Positive predictive value $PP(k)_j$ of clinical datum present (j) in patient 26 tends to increase probabilities P(k) of corresponding diagnoses (k). Sensitivity $S(i)_r$ of a clinical datum absent (r) tends to reduce probability P(k) of corresponding diagnoses (k). Therefore, a clinical datum (m) that has the greatest positive predictive value $PP(i)_m$ or the greatest sensitivity $S(i)_m$ will result in the greatest benefit because it increments the difference between probability P(k) of most likely diagnoses (k) and decrements probabilities P(k) of less likely diagnoses (k). Eventually, the less likely diagnoses (k) are eliminated from differential diagnosis list 34 (ruled out), whereas the most likely diagnoses (k) are confirmed as final diagnoses.

The magnitude of the increment or decrement of the aforementioned difference of diagnostic probabilities P(k) quantifies the benefit of clinical datum (m) that produces it. The quantitative component of benefit can thus be determined before actually investigating clinical datum (m) for its presence (as clinical datum present (j)) or its absence (as clinical datum absent (r)) in patient 26, by virtually testing with the algorithm both possible outcomes. The qualitative component of benefit cannot be quantified. It depends on multiple factors such as health status of patient 26 and ability to tolerate the procedure, patient financial status, insurance company approval, prognosis, involved physician liability, and existence of efficacious and available treatments for diseases (i) ruled in as possible diagnoses (k) in differential diagnosis list 34. Benefit must equal or exceed cost C(m). The evaluation of cost-to-benefit of clinical datum (m) and the decision to implement a procedure to obtain it must be discussed with and approved by patient 26. If patient 26 is wealthy, is not discouraged by the risk, or can tolerate discomfort, a procedure that incurs a greater cost C(m) may be acceptable. Confirmation of an uncertain diagnosis (k) of a potentially life-threatening but treatable disease (i) also may justify implementation of a more costly procedure.

As mentioned above, knowledge base 16 also has two identifiers associated with each clinical datum (m): risk (Rsk) and interaction (Int) identifiers. These (Rsk) and (Int) identifiers are assigned to clinical datum (m) when potentially dangerous circumstances prevail. They typically prompt a more extensive diagnostic work-up. Risk identifier (Rsk) flags any high-risk clinical datum (m) (e.g., dyspnea, chest pain, bleeding, laboratory test "panic" values) and any diagnosis with potentially bad outcome (e.g., myocardial infarction, pulmonary embolism, malignancy.) Interaction identifier (Int) flags a clinical datum that might have been modified or masked by a drug interaction or a concurrent disease. The medical analytics method checks for such interactions.

At this point clinical data (m) in knowledge base 16 has been properly indexed by their three indices (sensitivity S, positive predictive value PP, cost C) and flagged by the risk (Rsk) and interaction (Int) identifiers. A closer view of this structure and implementation in data files containing clinical data (m) is afforded by the schematic diagram of FIG. 2. Once clinical data (m) in knowledge base 16 are associated with these three indices (S, PP, C), which are preferably pre-computed, the connections between clinical data (m) and corresponding diseases (i) listed in disease (i) models can be established prior to examination of patient 26. This preparation will ensure high-speed performance during implementation. Meanwhile, the two identifiers (Rsk, Int) will preclude overlooking risky diseases (i).

Now, the complete mini-max procedure can be implemented. In order for this portion of the teaching to be as intuitive as possible to a person skilled in the art, the explanation of the mini-max procedure will be referenced to the manner in which physician 24 obtains clinical data (m) and proceeds from initial diagnoses (k) to the one or more final diagnoses (k). Recall first, that diagnoses (k) were ruled in into differential diagnosis list 34 when clinical data present (j) in patient 26 matched at least one clinical datum (m) in the corresponding disease (i) model stored in knowledge base 16. Any diagnosis (k) can be deleted or ruled out from differential diagnosis list 34 when probability P(k) of that diagnosis (k) falls below an empirical deletion threshold DT. Therefore, clinical data (m) that reduce probability P(k) of a diagnosis (k) favor the deletion of this diagnosis (k) from differential diagnosis list 34.

Notice that any given diagnosis (k) must first be ruled in into differential diagnosis list 34 before it can be ruled out and deleted from list 34. When patient 26 is new and clinical data present (j) are not known to doctor 24, there are two methods of achieving a final diagnosis.

The first method begins with a blank page, i.e., not knowing disease(s) (i) afflicting patient 26, and then formulating differential diagnosis list 34 based on clinical data present (j) or manifested by patient 26. These clinical data present (j) in patient 26, when matched with clinical data (m) for disease(s) (i), gradually increment the number of possible diagnoses (k); this process is called ruling in diagnoses. The greater the positive predictive value $PP(k)_j$ of clinical datum present (j), the more likely corresponding diagnosis (k).

For example, microhemagglutination for *Treponema pallidum* test (MHA-TP) is a clinical datum (m) of great positive predictive value $PP(i)_m$ for disease (i) being syphilis. Accordingly, if positive, it rules in this disease (i) as corresponding diagnosis (k) with great probability, because no other disease (i) manifests this clinical datum (m). Therefore, a clinical datum present (j) having a great positive predictive value $PP(k)_j$, strongly rules in diagnosis (k), even if sensitivity $S(i)_m$ (or, equivalently $S(k)_j$) is small, meaning that clinical datum (m) is not frequently found, but as it is already present in this case, sensitivity $S(i)_m$ is irrelevant. For example, filarias present in a blood sample is a clinical datum (m) with great positive predictive value $PP(i)_m$ for disease (i) filariasis, confirming corresponding diagnosis (k), despite low sensitivity $S(i)_m$.

On the other hand, clinical datum present (j), typically would not favor diagnosis (k) only because it has a great sensitivity $S(k)_j$. This simply says that clinical datum present (j) is frequently manifested by specified disease (i) corresponding to diagnosis (k), but many other diseases (i) also may manifest it (it has a small PP value). For example, weight loss has a great sensitivity S for hyperthyroidism, but a small PP value. Therefore, to rule in hyperthyroidism, another clinical datum (m) with a greater PP value, such as suppressed thyroid stimulating hormone (TSH) must be investigated. When clinical datum present (j) has a small $S(k)_j$, then this typically would not rule in diagnosis (k), because it simply means that this clinical datum (m) is rare for the disease (i), which is not a reason per se to rule in disease (i) as diagnosis (k). For example, consider diarrhea (small S and small PP value) for duodenal ulcer. Accordingly, ruling in a diagnosis (k) relies on clinical data that are present (j) and the greater their $PP(k)_j$ the more they will support this diagnosis (k). Sensitivity $S(k)_j$ is irrelevant if the clinical datum is present (j).

The second method of achieving a final diagnosis (k) begins with all known diseases (i), and then gradually decrementing the number of possible diagnoses (k) as sequentially investigated clinical data (m) for presence (j) in patient 26 are actually found absent (r). An unknown patient 26 could have any disease (i). For example, when we notice that he is a male, we realize that he cannot have an ovarian cancer; because he is young, prostate cancer is unlikely, and so forth. This process is called ruling out potential diagnoses (k).

To rule out a potential diagnosis (k), we rely on the sensitivity S of clinical data (m) that are absent (r) in patient 26. The greater the sensitivity $S(k)_r$ of a clinical datum absent (r), the less likely the corresponding diagnosis (k), even if the PP value is great, because clinical datum (m) is found absent (r). For example, microhemagglutination for *Treponema pallidum*, test (MHA-TP) is a clinical datum (m) of great S for syphilis; accordingly, if negative or absent (r), it rules out this disease (i) because it is positive in essentially all cases of syphilis (rare false negative tests). As mentioned in the previous paragraph, weight loss is a clinical datum (m) with great S for severe hyperthyroidism, because it is manifested in all such cases. Accordingly, if this clinical datum (m) is absent (r), the disease is ruled out.

A clinical datum (m) that is absent (r), with small S, has little influence on probability P(k) of diagnosis (k), even if its PP value is great. For example, filarias negative in blood (great PP value, but small S) for filariasis. Small sensitivity S of a clinical datum absent (r) does not rule out the corresponding diagnosis (k) because it only means that clinical datum (m) is rare for disease (i) corresponding to diagnosis (k). The absence of a rare clinical datum (m) does not exclude a diagnosis (k). For example diarrhea with small S and small PP value for duodenal ulcer, if absent, does not rule out this diagnosis. Accordingly, ruling out a diagnosis (k) relies on clinical data (m) that are absent and with great S, PP value is irrelevant if clinical datum (m) is absent.

This second method to achieve a final diagnosis is impractical because to analyze the several thousand known diseases (i) would require a prohibitively large number of clinical data absent (r) to rule out all but one or a few diseases (i). In reality, ruling in or ruling out is applied according to whether clinical datum (m) under consideration is present or absent, respectively.

The presence of clinical datum (m) rules in the corresponding diagnosis (k) with strength proportional to the PP value. The absence of clinical datum (m) rules out a diagnosis (k) with strength proportional to sensitivity S.

Table 1 shows how PP value and S of clinical datum (m) affect probability P(k) and the process of ruling in or ruling out of diagnosis (k) according to whether clinical datum (m) is present or absent in patient 26.

TABLE 1

Ruling In and Ruling Out of Diagnoses

| Clinical datum | PP value | S | P | Effect on Diagnosis | Example | Comments |
| --- | --- | --- | --- | --- | --- | --- |
| Present | Great | Great | Increased | Strongly ruled in | MHA-TP test for syphilis | Ruling in a diagnosis relies on clinical data present, with great PP value; S is irrelevant |
| | Great | Small | Increased | Strongly ruled in | Filariae in blood for filariasis | |
| | Small | Great | Unchanged | Weakly ruled in | Weight loss for hyperthyroidism | |
| | Small | Small | Unchanged | Weakly ruled in | Diarrhea for duodenal ulcer | |
| Absent | Great | Great | Reduced | Strongly ruled out | MHA-TP test for syphilis | Ruling out a diagnosis relies on clinical data absent, with great S; PP value is irrelevant |
| | Great | Small | Slightly changed according to value of S | Weakly ruled out | Filariae in blood for filariasis | |
| | Small | Great | Reduced | Strongly ruled out | Weight loss for hyperthyroidism | |
| | Small | Small | Slightly changed according to value of S | Weakly ruled out | Diarrhea for duodenal ulcer | |

Legend:
MHA-TP, microhemagglutination for *Treponema pallidum*, a highly exclusive and sensitive test for syphilis;
PP value, positive predictive value;
S, sensitivity;
P, probability.

Evidently, eight combinations are possible: clinical datum present with great PP value, clinical datum present with small PP value, clinical datum absent with great PP value, clinical datum absent with small PP value, clinical datum present with great S, clinical datum present with small S, clinical datum absent with great S, and clinical datum absent with small S. Of these eight combinations, only two are useful: clinical datum present with great PP value and clinical datum absent with great S. That is because only these can significantly change the probability P(k) of the corresponding diagnosis (k); all other combinations are disregarded.

So far, we have seen how clinical data present (j) and their associated PP values determine probability P(k) of diagnosis (k). Now, let us see how clinical data absent (r) and their associated sensitivity S(k)$_r$ values further influence probability P(k). In accordance with the medical analytics method of the invention, probability P(k) can be expressed as:

$$P(k) = \frac{PP(k)_j(1-S(k)_r)}{PP(1)_j(1-S(1)_r)+\ldots PP(k)_j(1-S(k)_r)+\ldots PP(n)_j(1-S(n)_r)} \quad (\text{Eq. 4})$$

Here P(k) is the probability of diagnosis (k) (e.g., tuberculosis), PP(k)$_j$ is the positive predictive value of one particular clinical datum present (j) for diagnosis (k) (e.g., *Mycobacterium tuberculosis* in sputum for tuberculosis), S(k)$_r$ is sensitivity of one particular clinical datum absent (r) for diagnosis (k) (e.g., fever for tuberculosis). PP(1)$_j$ through PP(n)$_j$ are positive predictive values of same clinical datum present (j) (*Mycobacterium tuberculosis*) for each respective diagnosis 1 through n in differential diagnosis list 34. S(1)$_r$ through S(n)$_r$ are sensitivities of clinical datum absent (r) (fever) for each respective diagnosis (k) in differential diagnosis list 34.

Note that the denominator of Eq. 4 has a series of terms, each of which refers to one of the 1 through n diagnoses (k) in differential diagnosis list 34. Each of these terms has two components: the PP(k)$_j$ value of clinical datum present (j) (*Mycobacterium tuberculosis*) and sensitivity S(k)$_r$ of clinical datum absent (r) (fever). These clinical data present and absent (j), (r) remain unchanged for all terms; but their respective PP values and S values change to values associated with each of the 1 through n diagnoses (k). Eq. 4 is related to Bayes formula, but is here used differently than in other prior art programs. It involves two independent clinical data: one present (j) and the other absent (r). Accordingly, Bayes condition of independence is not violated.

Referring to the example of *Mycobacterium tuberculosis* present in sputum (j=MTb) and fever absent (r=FA), we now explicitly apply Eq. 4 to illustrate how to specifically calculate the probability of tuberculosis P(TB):

$$P(TB) = \frac{PP(TB)_{MTS}(1-S(TB)_{FA})}{PP(BR)_{MTS}(1-S(BR)_{FA})+\ldots PP(TB)_{MTS}(1-S(TB)_{FA})+\ldots PP(EB)_{MTS}(1-S(EB)_{FA})},$$

where BR=bronchiectasis and EB=embolism are among the competing diagnoses (k) ruled in on list 34. Of course, more competing diagnoses (k) than just TB, BR, and EB are possible, e.g., LC=lung cancer. As far as P(TB) goes, we know that for *Mycobacterium tuberculosis* found in the sputum being a clinical datum present (j) PP(TB)$_{MTb}$=1. Next, fever as a clinical datum absent (r) when relating to TB diagnosis has a sensitivity S(TB)$_{FA}$=0.7. Knowledge of the remaining PP and S values allows one to compute P(TB) while also including the fourth diagnosis of lung cancer (LC) (last term in denominator PP(LC)$_{MTb}$(1−S(LC)$_{FA}$) to obtain:

$$P(TB) = \frac{1.00(1-0.70)}{0.00(1-0.00)+1.00(1-0.70)+0.00(1-0.30)+0.00(1-0.10)} = 1.$$

The result of Eq. 4 produces the correct probability value of P(TB)=1 for confirmed tuberculosis.

Eq. 4 is iterated to calculate the remaining probabilities P(BR), P(EB) and P(LC), that the *Mycobacterium tuberculosis* present in sputum (j) and fever absent (r), which taken together are called a clinical data pair (j, r) confers to pulmonary embolism and the other remaining diagnoses (k) in differential diagnosis list 34. PP values and S corresponding to each diagnosis (k) must be substituted in the numerator; the denominator remains unchanged. Eq. 4 also normalizes the probabilities of diagnoses (k), meaning that their sum P(TB)+P(BR)+P(EB)+P(LC) equals 1. Referring to our example:

Clinical data pair (j, r): *Mycobacterium* TB present, fever absent

| (k) | Full name of diagnosis | PP(k)$_j$ | S(k)$_r$ | P(k) |
|---|---|---|---|---|
| 1 | Pulmonary tuberculosis | 1.000 | 0.70 | 1.000 |
| 2 | Pulmonary embolism | 0.000 | 0.30 | 0.000 |
| 3 | Bronchiectasis | 0.000 | 0.00 | 0.000 |
| 4 | Lung cancer | 0.000 | 0.10 | 0.000 |
| | TOTAL PROBABILITY = | | | 1.000 |

The above examples were provided to illustrate the motivation behind the next step of the mini-max procedure; namely creation of clinical data pairs (j, r). One particular data pair (j, r) is illustrated on display 32 in FIG. 3. To create all possible clinical data pairs (j, r) the method instructs computer 12 to select from among all clinical data present (j) in patient 26 and all clinical data absent (r).

For reasons of clarity, sensitivities of clinical datum absent (r) will be denoted as S(k)$_r$ to refer directly to ruled in diagnosis (k), rather than S(i)$_r$, which refers back to disease (i) among the various models stored in file 22. Of course, the latter choice is permissible but would become less tractable in view of the remainder of the method of invention and the practical examples to follow in the implementation and examples section.

To calculate a total probability TP(k) (as explained later) of each diagnosis (k), the mini-max procedure must generate all possible clinical data pairs (j, r) with all thus-far investigated clinical data present (j) and absent (r). The number of clinical data pairs (j, r) generated will thus equal the number of clinical data present (j) multiplied by the number of clinical data absent (r). In other words, this portion of the mini-max procedure involves computing partial probabilities of diagnoses (k) denoted by partial P(k)$_{j,r}$ given clinical data pair (j, r) in a manner that simply builds on, or effectively re-states Eq. 4 as follows:

$$\text{partial } P(k)_{j,r} = \frac{PP(k)_j(1-S(k)_r)}{PP(1)_j(1-S(1)_r) + \ldots PP(k)_j(1-S(k)_r) + \ldots PP(n)_j(1-S(n)_r)}. \quad \text{(Eq. 5)}$$

Let us continue with the previous example to gain a better intuition about clinical data pairs (j, r) and the partial probabilities $P(k)_{j,r}$ they yield. Assume that we have 5 clinical data present (j) (cough, expectoration, hemoptysis, dyspnea, and *Mycobacterium tuberculosis*) and 2 clinical data absent (r) (cavity and fever). These will generate a total of 10 clinical data pairs (j, r): (cough, cavity); (cough, fever); (hemoptysis, cavity); (hemoptysis, fever); (dyspnea, cavity); (dyspnea, fever); (expectoration, cavity); (expectoration, fever); (Mycobacterium tuberculosis, cavity); (*Mycobacterium tuberculosis*, fever).

The resultant number of partial $P(k)_{j,r}$ values equals the number of clinical data pairs (j, r) multiplied by the number of diagnoses (k) in differential diagnosis list 34. In our example, we had 10 clinical data pairs (j, r) and 4 diagnoses (k) (pulmonary tuberculosis TB, pulmonary embolism EB, bronchiectasis BR, and lung cancer LC), yielding a total of 40 partial $P(k)_{j,r}$ values.

Below we show the tables of clinical data pairs (j, r) with these 40 partial $P(k)_{j,r}$ values. In particular, the partial $P(k)_{j,r}$ values are organized in 10 clinical data pair tables, one table for each clinical data pair (j, r). The first column lists diagnoses (k) from differential diagnosis list 34, and the intermediate columns apply Eq. 5. The last column lists the resultant partial $P(k)_{j,r}$ values obtained by dividing $PP(k)_j(1-S(k)_r)$ representing the numerator of Eq. 5 by the sum $$\sum_{k=1}^{n} PP(k)_j(1-S(k)_r)$$

representing its denominator. Note that n=4 in this case, since we have four possible diagnoses (k).

1. Clinical data pair table for clinical data pair (j, r): (cough, cavity)

| (k) | Abbr. name of diagnosis | $PP(k)_j$ | $S(k)_r$ | $PP(k)_j(1-S(k)_r)$ | $\sum_{k=1}^{4} PP(k)_j(1-S(k)_r)$ | partial $P(k)_{j,r}$ |
|---|---|---|---|---|---|---|
| 1 | TB | 0.276 | 0.60 | 0.110 | 0.730 | 0.151 |
| 2 | EB | 0.172 | 0.00 | 0.172 | 0.730 | 0.236 |
| 3 | BR | 0.310 | 0.10 | 0.279 | 0.730 | 0.382 |
| 4 | LC | 0.241 | 0.30 | 0.169 | 0.730 | 0.231 |
| | TOTAL OF PARTIAL PROBABILITIES $P(k)_{j,r}$ | | | | | 1.000 |

2. Clinical data pair table for clinical data air (j, r): (cough, fever)

| (k) | Abbr. name of diagnosis | $PP(k)_j$ | $S(k)_r$ | $PP(k)_j(1-S(k)_r)$ | $\sum_{k=1}^{4} PP(k)_j(1-S(k)_r)$ | partial $P(k)_{j,r}$ |
|---|---|---|---|---|---|---|
| 1 | TB | 0.276 | 0.70 | 0.083 | 0.731 | 0.113 |
| 2 | EB | 0.172 | 0.30 | 0.121 | 0.731 | 0.165 |
| 3 | BR | 0.310 | 0.00 | 0.310 | 0.731 | 0.425 |
| 4 | LC | 0.241 | 0.10 | 0.217 | 0.731 | 0.297 |
| | TOTAL OF PARTIAL PROBABILITIES $P(k)_{j,r}$ | | | | | 1.000 |

3. Clinical data pair table for clinical data pair (j, r): (hemoptysis, cavity)

| (k) | Abbr. name of diagnosis | $PP(k)_j$ | $S(k)_r$ | $PP(k)_j(1-S(k)_r)$ | $\sum_{k=1}^{4} PP(k)_j(1-S(k)_r)$ | partial $P(k)_{j,r}$ |
|---|---|---|---|---|---|---|
| 1 | TB | 0.222 | 0.60 | 0.089 | 0.767 | 0.116 |
| 2 | EB | 0.333 | 0.00 | 0.333 | 0.767 | 0.435 |
| 3 | BR | 0.167 | 0.10 | 0.150 | 0.767 | 0.196 |
| 4 | LC | 0.278 | 0.30 | 0.194 | 0.767 | 0.254 |
| | TOTAL OF PARTIAL PROBABILITIES $P(k)_{j,r}$ | | | | | 1.000 |

4. Clinical data pair table for clinical data pair (j, r): (hemoptysis, fever)

| (k) | Abbr. name of diagnosis | $PP(k)_j$ | $S(k)_r$ | $PP(k)_j(1-S(k)_r)$ | $\sum_{k=1}^{4} PP(k)_j(1-S(k)_r)$ | partial $P(k)_{j,r}$ |
|---|---|---|---|---|---|---|
| 1 | TB | 0.222 | 0.70 | 0.067 | 0.717 | 0.093 |
| 2 | EB | 0.333 | 0.30 | 0.233 | 0.717 | 0.325 |
| 3 | BR | 0.167 | 0.00 | 0.167 | 0.717 | 0.233 |

4. Clinical data pair table for clinical data pair (j, r): (hemoptysis, fever)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 4 | LC | 0.278 | 0.10 | 0.250 | 0.717 | 0.349 |
| | TOTAL OF PARTIAL PROBABILITIES $P(k)_{j,r}$ | | | | | 1.000 |

5. Clinical data pair table for clinical data pair (j, r): (dyspnea, cavity)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 0.148 | 0.60 | 0.059 | 0.774 | 0.077 |
| 2 | EB | 0.370 | 0.00 | 0.370 | 0.774 | 0.478 |
| 3 | BR | 0.037 | 0.10 | 0.033 | 0.774 | 0.043 |
| 4 | LC | 0.444 | 0.30 | 0.311 | 0.774 | 0.402 |
| | TOTAL OF PARTIAL PROBABILITIES $P(k)_{j,r}$ | | | | | 1.000 |

6. Clinical data pair table for clinical data pair (j, r): (dyspnea, fever)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 0.148 | 0.70 | 0.044 | 0.741 | 0.060 |
| 2 | EB | 0.370 | 0.30 | 0.259 | 0.741 | 0.350 |
| 3 | BR | 0.037 | 0.00 | 0.037 | 0.741 | 0.050 |
| 4 | LC | 0.444 | 0.10 | 0.400 | 0.741 | 0.540 |
| | TOTAL OF PARTIAL PROBABILITIES $P(k)_{j,r}$ | | | | | 1.000 |

7. Clinical data pair table for clinical data pair (j, r): (expectoration, cavity)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 0.417 | 0.60 | 0.167 | 0.672 | 0.248 |
| 2 | EB | 0.010 | 0.00 | 0.010 | 0.672 | 0.016 |
| 3 | BR | 0.469 | 0.10 | 0.422 | 0.672 | 0.628 |
| 4 | LC | 0.104 | 0.30 | 0.073 | 0.672 | 0.109 |
| | TOTAL OF PARTIAL PROBABILITIES $P(k)_{j,r}$ | | | | | 1.000 |

8. Clinical data pair table for clinical data pair (j, r): (expectoration, fever)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 0.417 | 0.70 | 0.125 | 0.695 | 0.180 |
| 2 | EB | 0.010 | 0.30 | 0.007 | 0.695 | 0.010 |
| 3 | BR | 0.469 | 0.00 | 0.469 | 0.695 | 0.675 |
| 4 | LC | 0.104 | 0.10 | 0.094 | 0.695 | 0.135 |
| | TOTAL OF PARTIAL PROBABILITIES $P(k)_{j,r}$ | | | | | 1.000 |

9. Clinical data pair table for clinical data pair (j, r): (Mycobacterium TB, cavity)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 1.000 | 0.60 | 0.400 | 0.400 | 1.000 |
| 2 | EB | 0.000 | 0.00 | 0.000 | 0.400 | 0.000 |
| 3 | BR | 0.000 | 0.10 | 0.000 | 0.400 | 0.000 |
| 4 | LC | 0.000 | 0.30 | 0.000 | 0.400 | 0.000 |
| | TOTAL OF PARTIAL PROBABILITIES $P(k)_{j,r}$ | | | | | 1.000 |

10. Clinical data pair table for clinical data pair (j, r): (Mycobacterium TB, fever)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 1.000 | 0.70 | 0.300 | 0.300 | 1.000 |
| 2 | EB | 0.000 | 0.30 | 0.000 | 0.300 | 0.000 |
| 3 | BR | 0.000 | 0.00 | 0.000 | 0.300 | 0.000 |
| 4 | LC | 0.000 | 0.10 | 0.000 | 0.300 | 0.000 |
| | TOTAL OF PARTIAL PROBABILITIES $P(k)_{j,r}$ | | | | | 1.000 |

The above clinical data pair tables illustrate an important normalization aspect of the mini-max procedure. For each clinical data pair (j, r), in each corresponding clinical data pair table, the sum of partial probabilities $P(k)_{r,j}$ for each of the ruled in diagnoses (k) is one. In other words, for every specific clinical data pair (j, r) we obtain $P(1)_{j,r} + \ldots P(k)_{j,s} + \ldots P(n)_{j,r} = 1$, or, expressed in standard summation convention:

$$\sum_{k=1}^{n} P(k)_{i,j} = 1.$$

Thus, we have calculated partial probability $P(k)_{j,r}$ that each clinical data pair (j, r) confers to each diagnosis (k).

Now, we must determine total probability TP(k) that partial probabilities $P(k)_{j,r}$ confer to each diagnosis (k) in differential diagnosis list 34. This is achieved by generating a mini-max table 38(k) for each diagnosis (k) ruled in into differential diagnosis list 34 as shown in FIGS. 4I-IV.

A first data column 38A(k) of each mini-max table 38(k) (i.e., the first column containing numerical data) lists the positive predictive values $PP(k)_j$ of clinical data present (j) in patient 26 for diagnosis (k) considered in the particular mini-max table 38(k). Meanwhile, an actual first column 38B(k) of table 38(k) as shown in FIG. 41 lists the names of these clinical data present (j) for a more understandable and intuitive presentation.

A first row 38C(k) of each mini-max table 38(k) lists the sensitivities $S(k)_r$ of clinical data absent (r) from patient 26 for diagnosis (k) considered in that particular mini-max table 38(k).

Mini-max tables 38(k) are preferably displayed to physician 24 on display 32 to aid in the diagnostic quest and are intended to help find the total probabilities TP(k) of corresponding diagnoses (k). To achieve this goal, the instructions executed by computer 12 to create them further involve: a) transferring each partial probability $P(k)_{j,r}$ into cells of the mini-max table where the $PP(k)_j$ value of each clinical datum present (j) and the sensitivity $S(k)_r$ of each clinical datum absent (r) converge; and b) selecting from among the partial probabilities $P(k)_{j,r}$ in the cells a determining partial probability $DP(k)_{j,r}$ having the smallest value in its row and the greatest value in its column. At this point, the determining probability $DP(k)_{j,r}$ is selected as the total probability $TP(k)$ for the diagnosis (k) for which the mini-max table in question was created. //

FIGS. 4I-IV and the clinical data pair tables are helpful in understanding how computer 12 implements the steps of transferring into and selecting partial probabilities $P(k)_{j,r}$ from each mini-max table 38(k). Returning to the specific example from above, total probability TP(k) for (k)=(TB or tuberculosis) at this diagnostic step is the maximum value TP(TB)=1.000, which is the value found in the last column of mini-max table 38(TB) in FIG. 4I. Similarly, total probability for diagnosis (k) being pulmonary embolism, TP(EB), at this diagnostic step is the maximum value TP(EB)=0.350 in the last column of mini-max table 38(EB) in FIG. 4II. According to mini-max table 38(BR) in FIG. 4III total probability of bronchiectasis at this diagnostic step is the maximum value 0.469 in the last column: TP(BR)=0.469. Were the second column not included in the calculation, TP(BR) would be 0.628. The reasons for working with first data column 38A(k) will be addressed below. Finally, total probability of lung cancer at this diagnostic step is the maximum value 0.402 in the last column of mini-max table 38(LC) shown in FIG. 4IV: TP(LC)=0.402.

Mini-max tables 38(k) aid the physician 24 in following the manner in which total probabilities TP(k) are found. In general, the determination of total probabilities TP(k) for diagnoses (k) by the medical analytics method executed by computer 12 is based on partial probabilities $P(k)_{j,r}$ and the following eight simple concepts listed below in steps.

1. A clinical data pair (j, r) is composed of a clinical datum present (j) and a clinical datum absent (r).
2. A specific clinical data pair (j, r) (in some clinical data pair tables) is responsible for the total probability TP(k) of a specific diagnosis (k).
3. In this specific data pair (j, r), the clinical datum present (j) has the greatest positive predictive value $PP(k)_j$ of all clinical data present (j), and the greatest rule-in effect for the specific diagnosis (k).
4. In this specific data pair (j, r), the clinical datum absent (r) has the greatest sensitivity $S(k)_r$ of all clinical data absent (r) and the greatest rule-out effect for the specific diagnosis (k).
5. Applying Eq. 5 to the positive predictive value $PP(k)_j$ of the clinical datum present (j) and the sensitivity $S(k)_r$ of the clinical datum absent (r) in the specific clinical data pair (j, r) yields a specific partial probability $P(k)_{j,r}$ for the specific diagnosis (k).
6. A specific cell for this specific partial probability $P(k)_{j,r}$ exists in the corresponding mini-max table 38(k) created for this specific diagnosis (k).
    a) In this specific cell, the clinical datum present (j) (of step 3) converges with the clinical datum absent (r) (of step 4).
    b) In this specific cell, the value of the specific partial probability $P(k)_{j,r}$ (of step 5) was transferred from the corresponding clinical data pair table to mini-max table 38(k).
    c) In this specific cell, the value of the specific partial probability $P(k)_{j,r}$ is simultaneously the smallest in its row and the greatest in its column.
7. We call the specific clinical data pair (j, r) (of step 2) the determining clinical data pair (j, r), because it determines the value of the specific partial probability $P(k)_{j,r}$ (of step 5).
8. We call this specific partial probability $P(k)_{j,r}$ the determining partial probability $DP(k)_{j,r}$ because it determines and equals the value of the total probability TP(k) of the specific diagnosis (k) (see marked cells in mini-max tables 38(k)).

To find the clinical data pair (j, r) that is the determining clinical data pair responsible for the current total TP(k) of diagnosis (k), we must backtrack the steps that lead from that pair to total TP(k). Start at the last cell (TP(k)) of a mini-max table 38(k) and ascend (following the arrows in any mini-max diagnosis table) to any cell with the same value, then go left on that row until any cell with the same value (determining partial probability $DP(k)_{j,r}$) is encountered. Clinical datum present (j) and clinical datum absent (r) that converge to this cell comprise the determining clinical data pair (j, r); their respective $PP(k)_j$ and S values are as shown in mini-max table 38(k).

Example: In mini-max table 38(LC) shown in FIG. 4IV the last cell shows total probability TP(LC)=0.402 of diagnosis (LC or lung cancer). Following the arrows takes us to another cell with the italicized value 0.402, which is the determining partial probability $DP(k)_{j,r}$. To this cell converge $PP(k)_j$, $_r$=0.444 of dyspnea present and sensitivity $S(k)_r$=0.3 of pulmonary cavity absent. The clinical data pair (dyspnea, cavity) is thus responsible for the current determining partial $DP(k)_{j,r}$ and total TP(LC)=0.402.

In a practical diagnostic quest, it is necessary to establish some criteria for confirming and ruling out diagnoses (k) in differential diagnosis list 34. In accordance with the method of invention, a diagnosis (k) is confirmed as a final diagnosis (k) when its total probability TP(k) is greater than a confirmation threshold value CT. Similarly, a diagnosis (k) is deleted or ruled out when its total probability TP(k) is smaller than a deletion threshold DT. Under normal circumstances, the numerical values of CT and DT are determined empirically. Once all of the diagnoses (k) in differential diagnosis list 34 have satisfied either the confirmation threshold CT or the deletion threshold DT the method can be stopped.

At this point the fundamental properties of the mini-max procedure are recapitulated in nine points with additional examples and insights to enhance the skilled artisan's understanding.

1. Each additional clinical datum present (j) generates a new row in an existing mini-max table 38(k).
2. Each additional clinical datum absent (r) generates a new column in an existing mini-max table 38(k).
3. A mini-max table 38(k) has only one determining partial P cell, the value of which (italicized in the tables shown in FIGS. 4I-IV) is the smallest of its row and the greatest of its column. The clinical datum present (j) and the clinical datum absent (r) that converge to this cell constitute the clinical data pair (j, r) that originated this partial probability $P(k)_{j,r}$ that equals the total probability TP(k) of diagnosis (k).
4. When an additional clinical datum present (j) is processed with the mini-max procedure, total probability TP(k) of diagnosis (k) may increase, depending on positive predictive value $PP(k)_j$ of clinical datum present (j). Typically, when an additional clinical datum absent (r) is processed with the mini-max procedure, the greater its sensitivity $S(k)_r$ the more it decreases total probability TP(k) of diagnosis (k). However, exceptions to this rule result from the effect sensitivity S values of any clinical datum (m) have for the other diagnoses (k) in the clinical data pair tables and from the interaction of the resulting partial probabilities $P(k)_{j,r}$ in mini-max table 38(k). Thus, total probability TP(k) of diagnosis (k) will either decrease, increase, or remain unchanged according to the following patterns:

A. Total probability TP(k) decreases. Let's concentrate on a clinical data pair table. For a specific diagnosis (k), the S(k)$_r$ of clinical datum absent (r) is inversely related to its partial probability P(k)$_{j,r}$ and directly related to partial probabilities P(k)$_{j,r}$ of other diagnoses (k). An additional clinical datum absent (r) typically reduces total probability TP(k) of diagnosis (k) if its sensitivity S(k)$_r$ is greater than sensitivity S(k)$_r$ of clinical datum absent (r) in determining clinical data pair (j, r). The latter being responsible for the current determining partial probability DP(k)$_{j,r}$ of diagnosis (k). If this condition is fulfilled, this new partial probability P(k)$_{j,r}$ will be less than current determining partial probability DP(k)$_{j,r}$ and becomes the new determining partial probability DP(k)$_{j,r}$ that equals total probability TP(k) in mini-max table 38(*k*).

B. TP(k) increases. The mini-max procedure is not intended to increase TP(k) of diagnosis (k) based on clinical data absent (r). Nevertheless, this occasionally occurs, but only when initial clinical datum absent (r) is processed; because at this point only one clinical datum absent (r) column is generated, smaller values do not exist in the rows. The greatest P(k)$_{j,r}$ value in this column becomes the determining partial probability DP(k)$_{j,r}$ and if it exceeds the current TP(k), it will replace the latter. Any subsequent clinical datum absent (r) that is processed—regardless of its S value and resulting P(k)$_{j,r}$—can only decrease TP(k), because only the smallest P(k)$_{j,r}$ in a row can become determining partial DP(k)$_{j,r}$. If we do not want an initial clinical datum absent (r) to increase current TP(k) of diagnosis (k), then the first data column of mini-max table 38(*k*) must be included in the calculation. In this way, we avoid violating the general rule that clinical datum absent (r) must never increase TP(k).

An example is mini-max table 38(BR) for bronchiectasis (see FIG. 4III), where total probability TP(BR) would have been 0.628 (italicized) instead of 0.469, were the second column not included in the calculation.

C. TP(k) does not change, when clinical datum absent (r) does not fulfill any of the conditions for decreasing or increasing TP(k). This occurs frequently; furthermore, TP(k) of diagnosis (k) is quite resistant to change, especially for diagnoses (k) with a great TP(k). This is an important advantage of the mini-max procedure, because it precludes ruling out a confirmed diagnosis (k) strongly supported by clinical data present (j) by some relatively unimportant clinical datum absent (r).

5. The order in which clinical data are processed is irrelevant; it will change only the relative position of the generated new row or column without affecting total probability TP(k) of diagnosis (k). This commutative order is intuitive and consistent with experience.

6. When an additional clinical datum present (j) or absent (r) is incorporated into mini-max table 38(*k*), the previously calculated P(k)$_{j,r}$ values for diagnosis (k) in table 38(*k*) remain unchanged and need not be recalculated. Such P values are retained in case a need arises to determine which clinical datum pair (j, r) generated a specific partial probability P(k)$_{j,r}$ in a cell. The algorithm on computer 12, however, need remember the values in the last column only. Whenever an additional clinical datum (m) is processed, new clinical data pairs are generated and new partial P values are calculated. The algorithm then compares these new partial P values with the existing partial P values in the last column and calculates the new TP(k) of diagnosis (k).

7. An interesting property of the mini-max procedure is revealed when the sum of total probabilities TP(k) of all diagnoses (k) in differential diagnosis list 34 is substantially greater than 1, i.e., $$\sum_{k=1}^{n} TP(k) > 1.$$

This suggests that not all diagnoses (k) are competing, but that some represent concurrent diseases (i). The degree of support that clinical datum (m) when found as clinical datum present (j) in patient 26 gives to diagnosis (k) is directly proportional to its corresponding positive predictive value PP(k)$_j$. This value can be found in the clinical datum (m) list associated with diagnosis (k) or in the first data column 38A(k) of the corresponding mini-max table 38(*k*). If all clinical data present (j) predominantly support the same diagnosis (k), the remaining diagnoses (k) tend to compete and the sum of total probabilities TP(k) of all diagnoses (k) in differential diagnosis list 34 is close to 1. When some clinical data (m) as found present (j) predominantly favor one diagnosis (k) and other clinical data (m) as found present (j) predominantly favor another diagnosis (k), these diagnoses (k) tend to be concurrent; the sum of their probabilities $$\sum_{k=1}^{n} TP(k)$$

will be considerably greater than 1. Concurrent diagnoses (k) are supported by different clinical data (m); accordingly, each concurrent diagnosis (k) can by itself attain a probability up to 1. The greater the sum of probabilities TP(k), the greater the number of concurrent diseases.

8. When a clinical datum present (j) with PP(k)$_j$ that approaches or equals 1 strongly supports or confirms a diagnosis (k), a clinical datum absent (r)—regardless of its S value—cannot reduce the great P that such a clinical datum present (j) confers to diagnosis (k). This property also is true for concurrent diagnoses (k) with great probability in differential diagnosis list 34. This important advantage precludes a confirmed diagnosis (k) from being ruled out by a relatively unimportant clinical datum absent (r). However, the P of a diagnosis (k) without a confirming clinical datum present may be reduced by the S of such clinical datum absent (r). Retaining diagnoses (k) with great P, while simultaneously ruling out diagnoses (k) with a small P, enables concurrent diagnoses (k) to be distinguished from competing diagnoses (k) in differential diagnosis list 34. The manner in which the algorithm running on computer 12 processes concurrent diagnoses (k) will be addressed later.

9. Each time an additional clinical datum absent (r) becomes available, the mini-max procedure implemented by computer 12 recalculates de novo the TP(k) values of diagnoses (k), simultaneously processing all present and absent clinical data (j) and (r). Prior art diagnostic programs that sequentially apply Bayes or other formulas for each additional clinical datum absent (r), typically cause an excessive reduction of P, even if only one clinical datum absent (r) is processed.

A diagnosis (k) with a great P, based on clinical datum present (j) with PP(k)$_j$=1, may be confronted with an additional clinical datum absent (r) with an $S(k)_r=1$. In this case display 32 should alert physician 24 to review if clinical datum present (j) or clinical datum absent (r) should win the rule in/rule out contest. In actual medical practice, this confrontation would be most unlikely to occur because S=1 means that this clinical datum (m) is always present. Furthermore, the mini-max procedure precludes the discredit of diagnosis (k) with a great TP(k) by clinical data absent (r).

Extending the Mini-Max Procedure to Recommending a Best Cost-Benefit Clinical Datum to Investigate Having thus reviewed the practical aspects of the mini-max procedure, we are ready to consider the best cost-benefit clinical datum (m) to investigate next for presence (j) or absence (r) in patient 26. This function can substantially shorten and reduce the cost of a diagnostic quest by precluding searches for futile clinical data (m). This has important socioeconomic implications, especially in this era of managed care, when insurance companies curtail tests and procedures, and when physicians are rated by their proficiency in ordering tests in general.

Computer 12 is faster and more accurate than physician 24 in selecting the most convenient clinical datum (m) next to investigate for presence (j) or absence (r) at each diagnostic step. Because the term best cost-benefit clinical datum (m) next to investigate in patient 26 is lengthy, we shorten it to best cost-benefit clinical datum (m). This best cost-benefit clinical datum (m) enables us to predict which new clinical datum (m) when found present (j) or absent (r) will most increase or decrease TP(k) of diagnosis (k), reducing the number of clinical data (m) required to achieve a final diagnosis.

Figure 2:
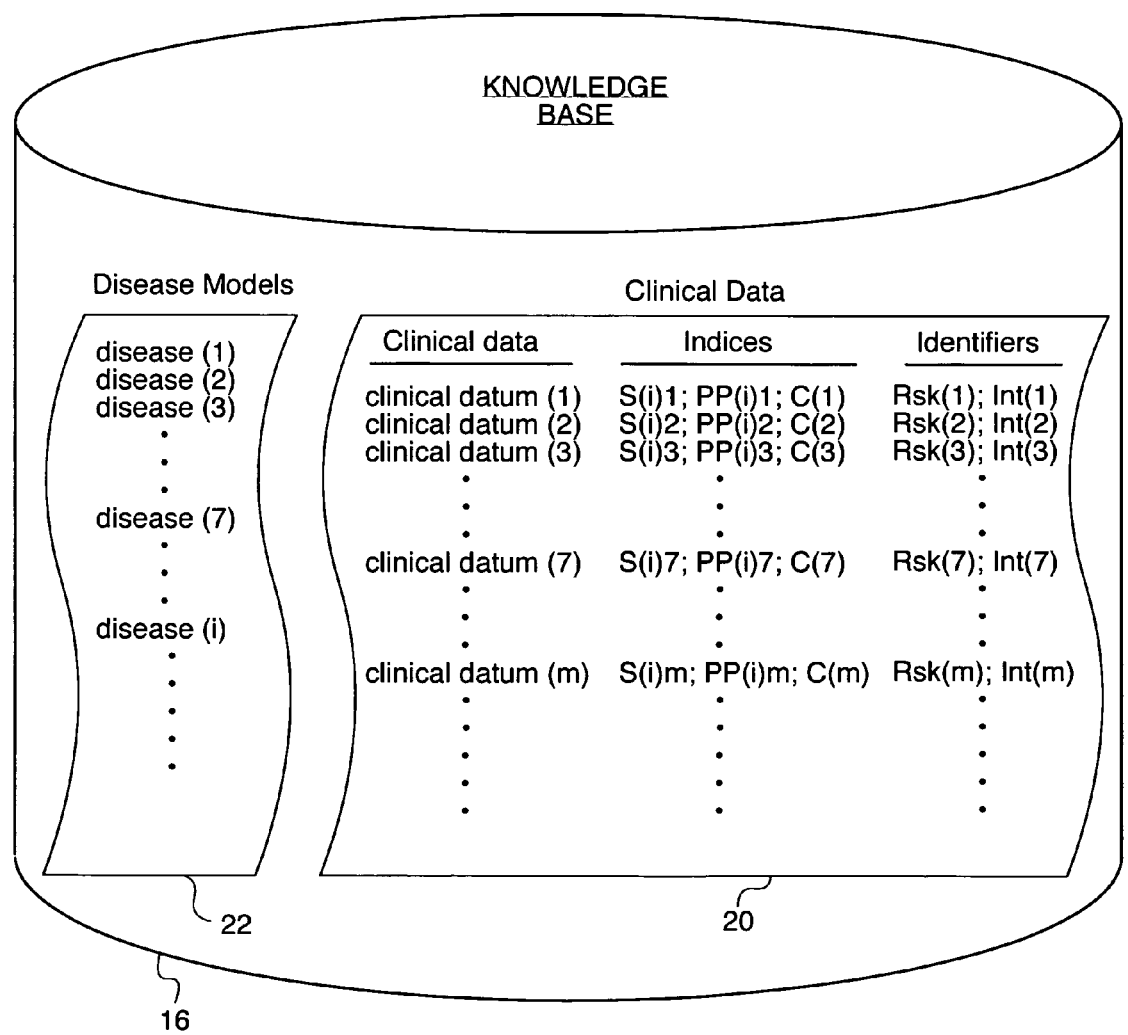
FIG. 2 is a schematic diagram of the knowledge base showing the use of three indices and two identifiers for clinical data.

The recommendation takes advantage of the third index associated with each clinical datum (m) as shown in the knowledge base 16 of FIG. 2, namely its cost C(m), as defined in the previous section entitled Theory behind the Complete Mini-Max Procedure. Cost C(m) represents the overall cost level associated with obtaining clinical datum (m):

$$C(m)=\max(\text{expense}(m), \text{risk}(m), \text{discomfort}(m)).$$

Because C(m) does not participate in the calculation of probability P(k) of diagnoses (k), its inexactness is not critical. This third index is considered now in selecting the most suitable clinical datum (m) to investigate next in patient 26.

To recommend a best cost-benefit clinical datum (m) to physician 24, computer 12 first selects in disease (i) models stored in knowledge base 16 and corresponding to diagnoses (k) that have been ruled in and included in differential diagnosis list 34 a specific clinical datum not yet investigated (y) in patient 26. This datum (y), of course, is taken from among the clinical data (m) that belong to disease (i) models. Preferably, the algorithm running on computer 12 examines every diagnosis (k) in differential diagnosis list 34 and selects from its respective disease (i) model all clinical data not yet investigated (y). These clinical data (y) differ from those initially collected; they are expected to be numerous because each disease (i) model will contribute many new clinical data (m). However, only clinical data (m) of appropriate cost C(m) and either of great PP value or great S need be among those investigated (y) for presence or absence.

In the next step, cost C(y) of collecting clinical datum not yet investigated (y) is computed with the above equation, namely:

$$C(y)=\max(\text{expense}(y), \text{risk}(y), \text{discomfort}(y)).$$

Then, the not yet investigated clinical data (y) are classified hierarchically by cost C(y) and probability $P(k)_y$ of corresponding diagnoses (k). Specifically, data (y) is organized according to three hierarchical levels shown in the diagram of FIG. 5. The first level is COST CATEGORIES, comprising four vertically arranged categories: none, small, intermediate, and great. The second level is DIAGNOSES, comprising all diagnoses (k) in differential diagnosis list 34, identically repeated in each cost category, in order of decreasing P value.

The third level is CLINICAL DATA, comprising two lists called PP LIST 50 and S LIST 52 containing only those clinical data not yet investigated (y) that have a cost C(y) that conforms with the corresponding cost category. Both lists 50, 52 contain the same clinical data (y), but ordered according to decreasing PP value and decreasing S, respectively. Consequently, these clinical data (y) generally exhibit different sequences in list 50 and 52.

Having thus organized the data hierarchically, computer 12 can consider recommending a new clinical datum not yet investigated (y) to be the best cost-benefit clinical datum by treating it as if present (j) in patient 26. To accomplish this, the algorithm moves to the lowest as-yet-unprocessed COST category, selects the as-yet-unprocessed DIAGNOSIS with greatest P, and from corresponding PP LIST 50, selects the as-yet-unprocessed clinical datum (y) with the greatest PP value. This PP value then is compared to the PP value of clinical datum present (j) in the current determining clinical data pair (j, r). The value of the latter appears in the bottom cell of the second column of mini-max table 38(k) for this diagnosis (k), and equals the current P(k) of diagnosis (k) before processing clinical data absent (r). New clinical data (y) with equal or smaller PP can be disregarded because—even if present—they will not change the current P(k) of this diagnosis (k).

When clinical datum (y) has a PP value that exceeds the current P of diagnosis (k) before considering clinical data absent (r) (bottom cell of second column), the algorithm recommends it as best cost-benefit clinical datum not yet investigated (y). Physician 24 then verifies whether this clinical datum (y) is absent (r) or present (j). When this clinical datum is absent (r) it is disregarded, because if able to change the total P of diagnosis (k), it will be detected by S loop 56 discussed at the next step, which processes clinical data assumed absent (r) in patient 26.

When the recommended best cost-benefit clinical datum to be investigated (y) is found present (j), the algorithm generates a new clinical datum list headed by this datum (j), and the partial P of diagnosis (k) before considering clinical data absent (r) assumes the PP value of this new datum (j).

To recalculate the total P of diagnosis (k) after considering clinical data absent (r), several new clinical data pairs (j, r), combination of the best cost-benefit clinical datum present (j) with each clinical datum absent (r), are generated. New clinical data pair tables are created and the partial $P(k)_{j,r}$ values for diagnosis (k) are calculated. A new row with these values is inserted in each mini-max table 38(k) and the total TP(k) of the corresponding diagnosis (k) is established. Computer 12 keeps selecting from the top of S list 52 clinical data (y) for processing as if they were absent (r), until no further clinical datum (y) is capable of decreasing current total TP(k) of respective diagnoses (k).

In this manner, one obtains total probabilities TP(k) for each of the diagnoses (k) ruled in into differential diagnosis list 34 under inclusion of clinical datum not yet investigated (y) into the mini-max procedure. Once all mentioned results are available, clinical datum (y) that would be responsible for the largest or maximum change to current total probabilities TP(k) of corresponding diagnoses (k) are identified. Now, the benefit (as defined earlier) of each clinical datum not yet investigated (y) for each diagnosis (k) becomes evident and provides a rational basis for selecting and recommending best cost-benefit clinical data that minimize cost and maximize benefit. Differently put, clinical datum not yet investigated (y) is selected to best balance the cost C(y) of obtaining it against its impact or change to total probability TP(k) for corresponding diagnosis (k).

Clearly, this approach can be extended to dealing with a number of clinical data not yet investigated (y) in the patient while balancing cost C(y) against the benefit expressed in terms of maximizing the change in the values of total probabilities TP(k) for corresponding diseases (k). As before, this balance between cost and benefit is ensured by computing a total probability TP(k) for each of the diagnoses (k) ruled in into differential diagnosis list 34 while first treating clinical data not yet investigated (y) as if they were present (j) and then as if they were absent (r) in patient 26.

Once recommended best cost-benefit clinical data have been investigated in patient 26, the resulting presence (j) or absence (r) of such clinical data is entered by physician 24 via input device 30 into computer 12. Computer 12 then iterates this portion of the method. Each time, the mini-max procedure computes the new total probabilities TP(k) of diagnoses (k) in differential diagnosis list 34 sorted by decreasing probabilities. The described steps are iterated sequentially with nested loops 54, 56, as indicated in FIG. 5 by boxes with circumferential arrows. The iterations proceed while increasing cost categories from none towards great, i.e., from top to bottom in FIG. 5, until the diagnostic quest is completed.

The implementation of this recommendation is explained in detail with reference to the example presented in the previous section. We start by organizing the four diagnoses (k) ruled in into differential diagnosis list 34 in accordance with decreasing total probabilities TP(k) as follows:

| Differential Diagnosis List 34 | | |
|---|---|---|
| Diagnosis (k) | Name of Diagnosis (k) | TP(k) |
| (k) = (1) | Tuberculosis | 1.000 |
| (k) = (2) | Bronchiectasis | 0.469 |
| (k) = (3) | Lung cancer | 0.402 |
| (k) = (4) | Pulmonary embolism | 0.350 |

Note that the total probabilities TP(k) of diagnoses (k) do not satisfy, except for tuberculosis, any reasonable confirmation or deletion thresholds CT, DT that would be deemed sufficient by physician 24 for a meaningful selection of a final diagnosis. Therefore, additional clinical data not yet investigated (y) must be collected and the mini-max procedure must be iterated with each such additional clinical datum (y). Then, total probabilities TP(k) of all diagnoses (k) have to be recalculated, until requirements for conclusion of the diagnostic quest are satisfied; i.e., reaching a reasonable confirmation threshold CT and a reasonable deletion threshold DT.

In the exemplary case, we can ask whether clinical datum not yet investigated (y) of pulmonary mass as evidenced by X-ray plain films, when found as clinical datum present (j), can increase the current total P of diagnosis (k) being lung cancer. The $PP(i)_m$ value of clinical datum (m) being pulmonary mass for disease (i) being lung cancer, as stored in the disease (i) model in knowledge base 16, is 0.857. Eq. 3 states that the greatest of the $PP(k)_j$ values supporting a diagnosis (k) equals the probability P(k) of this diagnosis. Therefore, applying Eq. 3 and treating pulmonary mass as if it were a clinical datum present (j) yielding $PP(LC)_{mass}$ we obtain:

$$P(LC)=\max(PP(LC)_{cough}, PP(LC)_{hemoptysis}, PP(LC)_{dyspnea}, PP(k)_{expectoration}, PP(LC)_{MTb}, PP(LC)_{mass})\ P(LC)=\max(0.241, 0.278, 0.444, 0.104, 0.000, 0.857)=0.857.$$

Accordingly, the previous P(LC)=0.444, before considering clinical data absent (r) (bottom cell of second column in the lung cancer mini-max table 38(LC) in FIG. 4IV), is increased to its new value of 0.857.

The algorithm running on computer 12 now generates and displays on display 32 a new clinical datum list as follows:

| Pulmonary mass | S | PP value |
|---|---|---|
| Lung cancer (LC) | 0.9 | 0.857 |
| Pulmonary tuberculosis (TB) | 0.1 | 0.095 |
| Pulmonary embolism (EB) | 0.05 | 0.048 |
| Bronchiectasis (BR) | 0.0 | 0.000 |

To determine the total P(k) of diagnosis (k), after considering clinical data absent (r), the algorithm generates two new clinical data pair tables and calculates the partial P values for lung cancer:

11. Clinical data pair table for clinical data pair (j, r): (mass, cavity)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | LC | 0.857 | 0.30 | 0.600 | 0.686 | 0.875 |
| 2 | TB | 0.095 | 0.60 | 0.038 | 0.686 | 0.055 |
| 3 | EB | 0.048 | 0.00 | 0.048 | 0.686 | 0.070 |
| 4 | BR | 0.000 | 0.10 | 0.000 | 0.686 | 0.000 |
| | TOTAL OF PARTIAL PROBABILITIES $P(k)_{j,r}$ | | | | | 1.000 |

12. Clinical data pair table for clinical data pair (j, r): (mass, fever)

| (k) | Abbr. name of diagnosis | $PP(k)_j$ | $S(k)_r$ | $PP(k)_j(1-S(k)_r)$ | $\sum_{k=1}^{4} PP(k)_j(1-S(k)_r)$ | partial $P(k)_{j,r}$ |
|---|---|---|---|---|---|---|
| 1 | LC | 0.857 | 0.10 | 0.771 | 0.833 | 0.925 |
| 2 | TB | 0.095 | 0.70 | 0.028 | 0.833 | 0.034 |
| 3 | EB | 0.048 | 0.30 | 0.034 | 0.833 | 0.041 |
| 4 | BR | 0.000 | 0.10 | 0.000 | 0.833 | 0.000 |
| | TOTAL OF PARTIAL PROBABILITIES $P(k)_{j,r}$ | | | | | 1.000 |

Now, in the manner outlined above, computer 12 re-processes mini-max table 38(k) for lung cancer, i.e., 38(LC) to obtain the table as shown in FIG. 6A. Specifically, the algorithm generates a new row 38D(k) that shows these partial P values. Then, the total TP(LC) of diagnosis (LC) after considering clinical data absent (r) is established.

The total probability TP(LC) of lung cancer (LC) at this diagnostic step is the maximum value, i.e., TP(LC)=0.857 in the last column. Because of treating clinical datum not yet investigated (y) being pulmonary mass as if present (j) and evidenced in chest X-ray plain films, the TP(LC) increased from 0.402 to 0.857. Notice that except for the last two rows, partial P values shown in all other cells remain unchanged. However, the value and location of the determining partial $DP(k)_{j,r}$ cell has changed.

Having treated a clinical datum not yet investigated (y) as if it were a clinical datum present (j), computer 12 can now consider recommending this particular clinical datum (m) to be the best cost-benefit clinical datum not yet investigated (y) by now treating it as if were absent (r) in patient 26. Typically, the greater the S of a clinical datum absent (r), the more it decreases the TP(k) of diagnosis (k). However, with the mini-max procedure, clinical datum absent (r) can occasionally increase TP(k). It can also occur that a clinical datum (m) with a lesser $S(i)_m$, can decrease TP(k) more than another clinical datum absent (r) with a greater $S(k)_r$.

To verify whether a new clinical datum absent (r) will indeed decrease TP(k), the mini-max procedure needs not always be applied in its entirety. Preferably, and in order to save computer 12 time a 3-step method is applied. Should the first or second of these steps prove that a clinical datum not yet investigated (y) and found absent (r) does not decrease TP(k), the following steps would be rendered unnecessary and the algorithm will move to next diagnosis (k) or cost category in FIG. 5.

Besides shortening the processing time, the 3-step method also determines whether another clinical datum not yet investigated (y) with lesser $S(k)_r$ value if found as clinical datum absent (r) is nevertheless able to reduce TP(k) of diagnosis (k). This determination is accomplished by the first step only. When a clinical datum absent (r) is proved not to reduce P, neither will another datum (y) of lesser S, and the algorithm moves to next diagnosis (k). This is not true for the second and third steps. Even when these steps prove that the new clinical datum absent (r) does not reduce P, the next clinical datum (y) with lesser S must be processed with the first step, to determine whether this lesser S clinical datum (y) can reduce P.

Referring back to the diagram of FIG. 5, in the same COST category and DIAGNOSIS in which a new best cost-benefit clinical datum (y) treated as if it were a clinical datum present (j) was processed from PP LIST 50, the algorithm moves now to S LIST 52. From this list, a clinical datum (y) of greatest S, not yet selected, is chosen. This datum (y) substitutes the clinical datum absent (r) in the current determining clinical data pair, thereby creating a new clinical data pair (j, r).

Now, the steps of the 3-step method are implemented in S loop 56 to determine whether this new clinical datum (y) if found absent (r) would decrease TP(k). This will make recommendations of best cost-benefit clinical data (y) to investigate next effective and efficient. Specifically, determining whether the absence (r) of any clinical datum (y) among clinical data (y) will decrease a total probability TP(k) of the corresponding diagnosis (k) is useful. The mini-max procedure for that clinical datum (y) can be discontinued if the absence (r) of such clinical datum (y) does not decrease the total probability TP(k).

First Step (4.1) of 3-Step Method

In the newly created clinical data pair (j, r), an equation related to Eq. 5 is applied to PP(k) based on clinical data present (j). Specifically, this equation expresses the probability $P(k)_s$ of the same diagnosis (k) after considering the sensitivity $S(k)_r$ of clinical datum absent (r) pertaining to the same diagnosis (k):

$$P(k)_s = PP(k)(1-S(k)_r). \tag{Eq. 6}$$

PP(k) stands for the probability of diagnosis (k) before considering the sensitivity $S(k)_r$ of clinical datum absent (r); this PP(k) is the maximum $PP(k)_j$ value of all clinical data present (j) that support the same diagnosis (see Eq. 3). $S(k)_r$ is the sensitivity of clinical datum absent (r) pertaining to the same diagnosis (k). When more than one clinical datum absent (r) refers to this diagnosis (k), then Eq. 6 should be applied to the clinical datum absent (r) having the largest S.

Thus, the S of the new clinical datum (y) from S list 52 is treated as if it belonged to a clinical datum absent (r). When the resulting P equals or exceeds the current TP(k) of diagnosis (k), neither this nor any other clinical datum in the same S list will decrease TP(k). Thus, following steps 4.2 and 4.3 can be skipped and the 3-step method can advance to the next diagnosis. Conversely, when the resulting P is smaller, TP(k) of diagnosis (k) under consideration might decrease; the resulting P is stored and method now proceeds with Step 4.2. Note that the Computational time of Step 4.1 (applying Eq. 6) involves only one subtraction and one multiplication.

Using the same example as above, consider that we need to know whether clinical datum not yet investigated (y) being pulmonary mass as evidenced by chest X-ray plain films, when treated as clinical datum absent (r) can decrease the current TP(k) of diagnosis (k) being lung cancer. Currently TP(LC)=0.402, as shown in the last cell of the corresponding mini-max table 38(LC) in FIG. 4IV. The P of lung cancer before considering clinical data absent (r) was 0.444 (equal to greatest PP value in the second column, corresponding to dyspnea present). The $S(k)_r$ of pulmonary mass on X-ray films for lung cancer is 0.9, as shown in corresponding S LIST 52. Substituting these values in Eq. 6, we obtain:

$$P(k)_s = PP(LC)_{dyspnea}(1 - S(LC)_{mass}) = 0.444(1 - 0.9)$$
$$= 0.044.$$

This $P(k)_s = 0.044$ is smaller than the prior TP(k) of lung cancer (TP(LC)=0.402). Therefore, absence (r) of mass in chest X-ray films might decrease TP(LC). The method now proceeds with Step 4.2.

Second Step (4.2) of 3-Step Method

A clinical data pair table is generated for the newly created clinical data pair (j, r) of first step (4.1). This table is headed by the clinical data pair (j, r) and lists all the diagnoses (k) in the differential diagnosis list 34. For each diagnosis (k), Eq. 6 is iterated, being applied to the corresponding PP value and S that the heading clinical data pair (j, r) has for this diagnosis (k), to obtain the corresponding not yet normalized P (these P values do not sum 1.) Eq. 5 is applied only to the diagnosis (k) associated with S LIST 52 from which clinical datum (y) with greatest S was selected. The numerator of Eq. 5 is the non-normalized P of this diagnosis (k) and the denominator is the sum of all non-normalized P values corresponding to diagnoses (k) in the clinical data pair table. The value of the numerator of Eq. 5 was calculated in first step (4.1). In the denominator, the clinical data pair (j, r) for each term is the same, but with PP values and S values related to respective diagnoses (k). The result is the normalized partial P of the mentioned diagnosis (k).

When the resulting partial P for diagnosis (k) under consideration equals or exceeds current TP(k), neither second step (4.2) nor third step (4.3) will decrease it. When this happens, the algorithm disregards clinical datum (y) being treated as if absent (r) and iterate the 3-Step method with the next greatest S clinical datum (y) in S list 52 for the same diagnosis (k), until first step (4.1) proves that no other clinical datum (y) with a smaller S can decrease TP(k). Then, the algorithm advances the 3-Step method to the next diagnosis (k). Conversely, when the resulting partial P is smaller than the current TP(k), the clinical datum not yet investigated (y) if found absent (r) might decrease total P. Thus, the resulting P is stored and the algorithm proceeds with third step (4.3).

Only if the new clinical datum (y) is indeed confirmed to be absent (r), will a new column be generated in mini-max diagnosis table 38(k). At second step (4.2), only one cell—at the intersection of the clinical datum present (j) and absent (r)—of this column (see example below) can show the result of Eq. 5. This cell shows the partial P that this clinical data pair (j, r) confers to diagnosis (k); all other cells of this column remain blank. Because Eq. 5 was applied to a clinical data pair (j, r) with a greater S than the previous one, we know that the resulting partial P is the smallest in its row, but we do not know yet whether it also will be the greatest in its column and become the determining partial P.

Note that second step (4.2) involves Eq. 5, whose numerator is equivalent to Eq. 6 and the denominator of which always is equal or less than 1. Accordingly, the result of Eq. 5 (partial P of the diagnosis in second step (4.2)) will always be greater than its numerator (P of the diagnosis in first step (4.1)). For this reason, it is unnecessary to proceed with second step (4.2) when first step (4.1) already yielded a P that equals or exceeds prior P.

In terms of computational time requirements on computer 12, second step (4.2) involves the application of Eq. 6 to all diagnoses (k) in only one clinical data pair table, and Eq. 5 to only one diagnosis (k) in this table. Computational time equals that of first step (4.1) (Eq. 6) times the number of diagnoses (k) (denominator of Eq. 5) plus the sum of the resulting terms (one sum for each diagnosis (k)) plus the division of the numerator by the denominator.

Returning now to our on-going example, the algorithm creates the (dyspnea, mass) clinical data pair table with the differential diagnoses showing the respective PP values and S values and then applies Eq. 5 to each diagnosis (k).

13. Clinical data pair table for clinical data pair (j, r): (dyspnea, mass)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 0.148 | 0.10 | 0.133 | | |
| 2 | EB | 0.370 | 0.05 | 0.352 | | |
| 3 | BR | 0.037 | 0.00 | 0.037 | | |
| 4 | LC | 0.444 | 0.90 | 0.044 | | |
| | | | | TOTAL OF PARTIAL PROBABILITIES $P(k)_{j,r}$ | | |

Now the algorithm applies Eq. 5 only to diagnosis (k) being processed, to obtain the partial P values that this clinical data pair (dyspnea, mass) confers to diagnosis (k) being processed. Here, diagnosis (k) is lung cancer, so we obtain:

$$P(LC) = \frac{PP(LC)_{dispnea}(1 - S(LC)_{mass})}{\begin{array}{l}PP(LC)_{dyspnea}(1 - S(LC)_{mass}) + \\ PP(TB)_{dispnea}(1 - S(TB)_{mass}) + \\ PP(EB)_{dispnea}(1 - S(EB)_{mass}) + \\ PP(BR)_{dyspnea}(1 - S(BR)_{mass})\end{array}}$$

$$P(LC) = \frac{0.444(1 - 0.90)}{\begin{array}{l}0.444(1 - 0.90) + \\ 0.148(1 - 0.10) + \\ 0.370(1 - 0.05) + \\ 0.037(1 - 0.00)\end{array}} = 0.078$$

The algorithm adds this result in clinical data pair table 13.

13. Clinical data pair table for clinical data pair (j, r): (dyspnea, mass)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 0.148 | 0.10 | 0.133 | | |
| 2 | EB | 0.370 | 0.05 | 0.352 | | |
| 3 | BR | 0.037 | 0.00 | 0.037 | | |
| 4 | LC | 0.444 | 0.90 | 0.044 | 0.566 | 0.078 |
| | TOTAL OF PARTIAL PROBABILITIES $P(k)_{j,r}$ | | | | | |

At this point, the algorithm sets up mini-max table 38(k) for lung cancer (38(LC)) when clinical datum absent (r) is pulmonary mass, as shown in FIG. 6B. Table 38(LC) includes new column 38E(k) titled "absent mass", listing only one partial P conferred by (dyspnea, mass) clinical data pair to diagnosis (k) being lung cancer. The other cells of column 38E(k) remain empty.

Because 0.078 is less than 0.402 (current TP(LC)), the possibility remains that this TP(LC) might be decreased. Therefore, the algorithm proceeds to third step (4.3).

Third Step (4.3) of 3-Step Method

All possible new clinical data pairs (j, r) are generated, with each clinical datum present (j) combined with clinical datum not yet investigated (y) being treated as clinical datum absent (r). Same as in second step (4.2), Eq. 6 is applied to all diagnoses (k) and then Eq. 5 is applied only to diagnosis (k) being processed, but now in all the clinical data pair tables. This yields the partial $P(k)_{j,r}$ values that the new clinical data pairs (j, r) confer to diagnosis (k). These partial P values are entered in all cells of new column 38E(k) of mini-max table 38(k) as shown in FIG. 6C. Doing this yields the total TP(k) of diagnosis (k), showing whether this clinical datum not yet investigated (y) treated as if absent (r) and having the greatest S would indeed decrease TP. If so, this clinical datum (y), based on its treatment as being absent (r), is recommended as the best cost-benefit clinical datum (y) next to investigate. Otherwise it is disregarded and the algorithm moves to next diagnosis (k).

The computational time equals the duration of second step (4.2) multiplied by the number of new clinical data pairs (j, r).

To demonstrate this third step on the basis of the example, the algorithm creates the remaining new clinical data pair tables and iterates Eq. 5 for lung cancer in all of them.

14. Clinical data pair table for clinical data pair (j, r): (cough, mass)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 0.276 | 0.10 | 0.248 | | |
| 2 | EB | 0.172 | 0.05 | 0.164 | | |
| 3 | BR | 0.310 | 0.00 | 0.310 | | |
| 4 | LC | 0.241 | 0.90 | 0.024 | 0.747 | 0.032 |
| | TOTAL OF PARTIAL PROBABILITIES $P(k)_{j,r}$ | | | | | |

15. Clinical data pair table for clinical data pair (j, r): (hemoptysis, mass)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 0.222 | 0.10 | 0.200 | | |
| 2 | EB | 0.333 | 0.05 | 0.317 | | |
| 3 | BR | 0.167 | 0.00 | 0.167 | | |
| 4 | LC | 0.278 | 0.90 | 0.028 | 0.711 | 0.039 |
| | TOTAL OF PARTIAL PROBABILITIES $P(k)_{j,r}$ | | | | | |

16. Clinical data pair table for clinical data pair (j, r): (expectoration, mass)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 0.417 | 0.10 | 0.248 | | |
| 2 | EB | 0.010 | 0.05 | 0.164 | | |
| 3 | BR | 0.469 | 0.00 | 0.310 | | |
| 4 | LC | 0.104 | 0.90 | 0.010 | 0.864 | 0.012 |
| | TOTAL OF PARTIAL PROBABILITIES $P(k)_{j,r}$ | | | | | |

17. Clinical data pair table for clinical data pair (j, r): (Mycobacterium TB, mass)

| (k) | Abbr. name of diagnosis | $PP(k)_j$ | $S(k)_r$ | $PP(k)_j(1 - S(k)_r)$ | $\sum_{k=1}^{4} PP(k)_j(1 - S(k)_r)$ | partial $P(k)_{j,r}$ |
|---|---|---|---|---|---|---|
| 1 | TB | 1.000 | 0.10 | 0.900 | | |
| 2 | EB | 0.000 | 0.05 | 0.000 | | |
| 3 | BR | 0.000 | 0.00 | 0.000 | | |
| 4 | LC | 0.000 | 0.90 | 0.000 | 0.900 | 0.000 |
| | TOTAL OF PARTIAL PROBABILITIES $P(k)_{j,r}$ | | | | | |

The algorithm now completes new column 38E(k) ("mass absent") in mini-max table 38(LC) for lung cancer, as seen in FIG. 6C. Were a pulmonary mass found absent (r), the previous total TP(k) for diagnosis (k) being lung cancer indeed would be reduced from 0.402 to 0.078.

A clinical datum absent (r) with a lesser S occasionally is able to reduce TP(k) more than another with a greater S. This mandates processing clinical datum (y) in S list 52 immediately below that with greatest S, because this clinical datum (y), if absent (r), might further reduce TP(k). Accordingly, the 3-step method is iterated with clinical data (y) with progressively smaller S in S loop 56 until first step (4.1) no longer reduces TP(k). Such reduction of TP(k) will occur only occasionally and ceases after one or a few clinical data (y) with smaller S are processed. This does not significantly prolong selection of the best cost-benefit clinical datum (y), since only clinical data (y) with slightly smaller S can additionally reduce the TP(k).

Computer 12 preferably displays best cost-benefit clinical datum absent (r) to physician 24 on display 32 so that it can be investigated for actual presence (j) or absence (r) in patient 26.

When it is present (j), it is disregarded, because it neither can decrease TP(k) of diagnosis (k) (general rule) nor increase TP(k) (were it able to do so, it would have been detected by PP loop 54 in FIG. 5). When this clinical datum (y) is found absent (r), it possibly could be masked by a drug interaction or concurrent disease. Therefore, if this clinical datum absent (r) is flagged with an interaction identifier (Int) (see knowledge base 16 of FIG. 2), the algorithm checks for a drug or disease able to mask it. If confirmed, clinical datum absent (r) is disregarded and physician 24 is notified by displaying a corresponding message on display 32. If clinical datum absent (r) is not masked, the largest partial P in new column 38E(k) in mini-max table 38(k) becomes the new determining partial P, and TP(k) decreases to this value.

All diagnoses (k) in each cost category (none, small, intermediate, great) as shown in the diagram of FIG. 5 are similarly processed, as generally indicated by loop 58. Preferably, physician 24 is prompted each time the overall loop indicated by reference 60 goes to a greater cost category. The remaining differential diagnoses with their P are displayed and physician 24 is asked by the algorithm via display 32 whether to proceed in the greater cost category or defer diagnosis, diagnose by exclusion, or by empirical treatment.

The entire looping process (loops 54, 56, 58, 60) terminates when all final diagnoses are obtained, the cost exceeds the benefit, or all clinical data (y) able to change TP(k) are processed. Clinical data (y) that have the greatest PP value or the greatest S typically involve costly pathological investigations, such as biopsy or even autopsy. However, in an emergency or when condition of patient 26 is deteriorating, investigation of confirmatory clinical data (y) of great PP value takes priority over cost C(y).

In summary, to select the best cost-benefit clinical datum (y) to investigate next, the algorithm loops at three nested levels shown in FIG. 5: outer 60, intermediate 58, and inner 54, 56. Outer cost loop 60 processes clinical data (y) not yet investigated in order of increasing cost category: none, small, intermediate, and great. Within each cost category, intermediate diagnosis loop 58 processes the diagnoses (k) on differential diagnosis list 34 in order of decreasing P because those with greatest P values, are the best candidates for a final diagnosis, and can sooner conclude the diagnostic quest. Inner clinical data loop comprises two sub-loops 54, 56. First sub-loop 54 begins at the top of the PP value list and terminates when no clinical datum (y) exists with a PP value greater than the PP value of the determining clinical data pair. Second sub-loop 56 processes, within the same level, clinical data (y) sorted by decreasing S, terminating when no clinical datum (y) exists, able to change the P of the corresponding diagnosis (k).

Each new best cost-benefit clinical datum (y) when present (j) creates a new clinical datum list that includes diagnosis (k) of disease (i) based on disease (i) model in knowledge base 16 from which it was selected. This diagnosis (k) appears in some or all previous clinical datum lists because it originated the search for the new clinical datum (y). The latter merely increases the number of clinical data (y) that support this diagnosis. Some of the new clinical datum lists may include previously unlisted diagnoses (k) that also may manifest this clinical datum (y). When this occurs, such new diagnoses (k) will not have clinical data (y) in common with any previous diagnosis (k) because they were not included in previous clinical datum lists. Accordingly, previous and new diagnoses (k) must be concurrent. New clinical datum lists bring up new diagnoses (k); these, in turn, bring up new clinical data (y).

At first thought, this cycle may seem to iterate indefinitely until the universe of all clinical data (m) in knowledge base 16 is exhausted. In reality, this does not occur, because one single patient 26 cannot manifest all clinical data (m). At some point, the newly recommended best cost-benefit clinical datum (y) will simply be absent (r) and will not create a new clinical datum list, thus aborting the cycle. Still, it must be investigated so as to confirm its absence (r). Neither can patient 26 be afflicted by a multitude of concurrent diseases (i). Another factor limiting the number of diagnoses (k) is that a best cost-benefit clinical datum (y) is selected for its great PP value and accordingly is either pathognomonic for a single diagnosis (k) or supportive of only a few diagnoses (k).

To summarize, the determination of which are the best cost-benefit clinical data (y) to recommend for being investigated next in patient 26, the algorithm lists all not yet investigated clinical data (y) corresponding to all diagnoses (k) in differential diagnosis list 34. These clinical data (y) are classified hierarchically by cost, probability P(k) of corresponding diagnoses (k), and in two lists, one sorted by decreasing PP values (PP list 50) and the other comprising the same clinical data (y) but sorted by decreasing sensitivities S (S list 52), as displayed in FIG. 5.

Then, the mini-max procedure processes each of such clinical data (y) as if it were present (j) in patient 26 and then as if were absent (r), registering in both circumstances the impact on total probabilities TP(k) of each diagnosis (k) in differential diagnosis list 34. For this task computer 12 selects from the top of PP list 50 clinical data (y) for virtual processing as if present (j), until no further clinical datum (y) is capable of increasing current TP(k) of respective diagnoses (k). Similarly, computer 12 selects from the top of S list 52 clinical data (y) for virtual processing as if there absent (r), until no further clinical datum (y) is capable of decreasing current TP(k) of respective diagnoses (k).

Once all mentioned results are available, benefit (as defined earlier) of each clinical datum (y) for each diagnosis (k) becomes evident and provides the base for selecting and recommending best cost-benefit clinical data (y), minimizing cost C(y) and maximizing benefit.

Once recommended best cost-benefit clinical data (y) have been investigated in patient 26, the resulting presence (j) or absence (r) of such clinical data (y) is entered by corresponding input devise 30 of computer 12. The method is iterated and mini-max procedure computes new total probabilities TP(k) of diagnoses (k) in the differential diagnosis list 34 sorted by decreasing probabilities. The described steps are iterated sequentially with nested loops 54, 56, 58, 60 as displayed in FIG. 5, by increasing cost categories until the diagnostic quest is completed.

Best Cost-Benefit Clinical Data to Investigate Simultaneously

Few prior art diagnostic computer programs recommend a single best cost-benefit clinical datum (y) next to investigate. The inventors are not aware of any that simultaneously recommend a set of such data. The present method as taught in the preceding section recommends testing for an appropriate clinical datum (y) to see if it is present (j) or absent (r) in patient 26.

In daily clinical practice, physician 24 often needs to simultaneously order a set of several analyses, tests or procedures. This is critical for emergency cases. The medical analytics method of the invention can emulate such human behavior by iterating the best cost-benefit clinical data function described in the previous section. It can first treat each newly recommended best cost-benefit clinical datum (m) as virtually present (j) and then virtually absent (r), while observing the effect that each iteration has on the probability of each diagnosis (k). After several iterations, a set of several best cost-benefit clinical data to be investigated in patient 26 can be recommended by computer 12 to physician 24.

In this manner, extension of the mini-max procedure enables the simultaneous mathematical processing of clinical data present (j) in patient 26, that favor a diagnosis (k) and clinical data absent (r) that disfavor diagnosis (k) in same patient 26. The resulting probability of diagnosis (k), based on clinical data present (j) and clinical data absent (r) is more accurate than other methods because it circumvents the improper application of the Bayes formula with its inherent restrictive conditions (i.e., independent, exhaustive and incompatible). This is because the mini-max procedure is a better model or paradigm for capturing the kind of human reasoning that physician 24 employs to narrow down possible diagnoses (k) to just a few or one final diagnosis. Indeed, the mini-max procedure is well-suited to model human reasoning in various other applications where obtaining data comes at a cost and the nature of the medical conditions being studied does not link simply to the data. In other words, the data may be interdependent and compatible with several medical conditions at the same time.

In one embodiment, the medical analytics method executes the iterations required to propose a set of clinical data (m) to investigate simultaneously in the manner depicted by a trichotomy tree 70 illustrated in the diagram of FIG. 7. Each tree represents a single diagnosis on differential diagnosis list 34. Virtual branches, e.g., 72, 74, represent best cost-benefit clinical data present (j) or absent (r). The nodes, e.g., node 76, represent the P and their gray level encodes cost C(m) of clinical data (m) for diagnosis (k). Each node originates three new branches. As in the hierarchical arrangement of data in the diagram of FIG. 5, four cost level iterations are involved: none, small, intermediate and large. Accordingly, the total number of branches is $3^1+3^2+3^3+3^4=120$.

Each top branch, e.g., 72, originating at a node, such as node 76, considers the case where best cost-benefit clinical datum (y) selected from PP list 50 is present (j). Accordingly, it increases P of diagnosis (k) and is depicted by an ascending arrow. Each middle branch, e.g., branch 78, considers the case where this best cost-benefit clinical datum (y) is absent (r). Accordingly, it is disregarded, since it does not change P, and is depicted by a horizontal arrow. Each bottom branch, e.g., branch 74, considers the case where best cost-benefit clinical datum (y) selected from S list 52 is absent (r). Therefore, it decreases P and is represented by a descending arrow. The same middle branch, e.g., 78, also represents the situation when best cost-benefit clinical datum (y) selected from the S list 52 is present (j). Once again, in this case it can be disregarded, and does not change P.

Furthermore, middle branches, e.g., branch 78, also represent situations in which no best cost-benefit clinical datum (y) was found in either PP list 50 or S list 52. Accordingly, it offers no best cost-benefit clinical data (y) to investigate. This reduces best cost-benefit clinical data (y) to investigate to only two branches per node, the top (present) and the bottom (absent) branches. The middle branch is preserved however, because it leads to a next node. In entire tree 70, the total number of best cost-benefit clinical data (y) to investigate now is reduced to 80. This result, multiplied by the number of diagnoses (k) in differential diagnosis list 34 yields the number of best cost-benefit clinical data (m) to investigate, provided no best cost-benefit clinical data (m) are shared with other trees (diagnoses (k)).

Any one clinical datum (m) is frequently shared by diverse diseases (i), or diagnoses (k). However, a best cost-benefit clinical datum (y) selected from PP list 50 has a great PP value. Thus, when present (j), it is either very specific or pathognomonic for diagnosis (k). Such clinical datum (y) is typically not shared with any other tree. When a best cost-benefit clinical datum (y) is selected from S list 52 and found absent (r), it might be shared by diverse diagnoses (k), for which this clinical datum (m) occurs frequently (as supported by files 22 of disease (i) models in knowledge base 16).

In any single tree 70, the best cost-benefit clinical datum (y) considered present (j) is represented by the top branch. It typically has a great PP value and strongly supports diagnosis (k). The best cost-benefit clinical datum (y) considered absent (r), represented by the bottom branch, typically has a great S and strongly opposes diagnosis (k). Occasionally, an identical best cost-benefit clinical datum (y), with great $PP(k)_j$ when present (j) and great $S(k)_r$ when absent (r), may be recommended simultaneously in the top and bottom branch. This is not a conflict, because it refers to virtually present and absent alternatives that do not coexist in real patient 26.

Processing the entire set of best cost-benefit clinical data (y) perhaps could at once confirm as final those diagnoses (k) with a P close to 1 (confirmation threshold CT≈1) and rule out those with a P close to 0 (deletion threshold DT≈0). Unfortunately, the ability to exhaustively traverse all branches of exponentially growing trees is limited by the increasing number of clinical data (y) and cost C(y). At best, such an approach will enable us to move only a few steps forward.

Fortunately, heuristic shortcuts dispel this concern. As noted before, clinical data present (j) of great $PP(k)_j$ that strongly favor diagnosis (k) are unlikely to be opposed by clinical data absent (r) of great $S(k)_r$ that strongly disfavor the same diagnosis (k). Accordingly, when a diagnosis (k) with an initial great P is processed, we would expect the algorithm to recommend a best cost-benefit clinical datum (y) of greater PP value that would further enhance that P, rather than recommend a best cost-benefit clinical datum (y) of great S. Conversely, when a diagnosis (k) with an initial small P is processed, we would expect the algorithm to recommend a best cost-benefit clinical datum (y) of greater S that would further reduce that P, rather than recommend a best cost-benefit clinical datum (y) of great PP value. This expectation would favor virtual traversing from present to present branches toward greater P values of diagnosis (k) or from absent to absent branches toward smaller P values of diagnosis (k). Thus in tree 70, the process would tend to traverse solid exterior branches only, while avoiding zigzag traversal along dashed alternating present and absent interior branches.

If we elect not to exclusively traverse extreme exterior branches, a few virtual best cost-benefit clinical data (y) alternatively absent (r) and present (j) can be accepted. This maintains traversal near the exterior branches, leading to nodes with P near diagnosis (k) confirmation or elimination thresholds CT, DT.

In the preferred embodiment, the algorithm explores for each diagnosis (k) in differential diagnosis list 34 all possible virtual traversals until maximal or minimal P are attained, or until all available clinical data (m) are exhausted. To accomplish this goal, prompts and authorization requests to continue in the next greater cost category must be bypassed. Cost C(y) momentarily is disregarded so as to obtain an ample overview of all best cost-benefit clinical data (y) available. A decision regarding which best cost-benefit clinical data (y) to select and up to what cost C(y) can be made afterwards according to severity of disease (i). Clinical data (m) whose cost C(m)=NONE are obtained as part of the initial consultation, from the history and physical examination. After evaluation of these NO COST clinical data (m), physician 24 follows one or more of diverse strategies to select the most appropriate set of best cost-benefit clinical data (y) next to investigate.

- Select all clinical data (y) shown in tree 70; this is possible only if cost C(y) of acquiring them does not surpass an acceptable limit.
- Select only those clinical data (y) of lesser cost. If, as a consequence, the diagnostic quest is not concluded, investigation of costlier clinical data (y) can be pursued at a subsequent consultation. This strategy is consistent with standard medical practice.
- Select only best cost-benefic clinical data (y) corresponding to exterior branches (represented by the solid arrows in tree 70) that traverse to a P that equals or approximates 1 or 0 (confirmation or deletion thresholds CT, DT).
- Select preferably best cost-benefic clinical data (y) shared by more than one tree, if available; such data (y) can be used for calculating P of more than one diagnosis (k).

These choices can be made by the algorithm running on computer 12, if parameters of cost, number of tests, and computational time limits are provided.

Competing and Concurrent Diagnoses

The previous sections provide a skilled artisan with the fundamental teachings required to practice the core aspects of medical analytics method of invention. These include the manner of treating clinical data (m), the process of ruling in and ruling out of diagnoses (k) in differential diagnoses lists 34 and the operation of the mini-max procedure. The latter includes the creation and implementation of mini-max tables and recommendation of best cost-benefit clinical data (y) as well as sets of data (y) to simultaneously investigate in patient 26. The present section builds upon the previous teachings to further equip a skilled practitioner with tools and methods that take advantage of those teachings and build on the mini-max procedure to enhance diagnostic quests and address issues arising in conjunction with competing and concurrent diagnoses (k).

Specifically, thus far we have concentrated on competing diagnoses (k) in differential diagnosis list 34, and the several probabilistic and heuristic methods for selecting the final diagnosis (k) that corresponds to disease (i) actually afflicting patient 26. However, patient 26 may be afflicted by two or more concurrent diseases (i). Thus, the issues of competing diagnoses (k) and concurrent diagnoses (k) have to be taken into account by the medical analytics method. To accomplish that, the algorithm needs to distinguish competitive diagnoses (k) from concurrent diagnoses (k) and apply this distinction to differential diagnosis list 34; and specifically to diagnoses (k) ruled in into differential diagnosis list 34.

Of course, each diagnosis (k) is represented by a single mini-max table 38($k$) that computes the total probability TP(k) of that diagnosis (k), which is subsequently confirmed as final if it reaches confirmation threshold CT. The diverse mini-max tables 38($k$) compute TP(k) of corresponding diagnoses (k) independently from each other. Therefore, more than one table 38(k) can reach confirmation threshold CT and confirm the respective diagnosis (k). Nonetheless, in order to be of additional value and support to physician 24, it is useful during the diagnostic quest to display the underlying concurrent and/or competing nature of diagnoses (k) on display 32.

The situations in which issues of competition and concurrence of diagnoses (k) arise will be illustrated with clinical datum lists and Venn diagrams. A first situation in which two diagnoses (k), k=(A), (B), are non-overlapping is shown in the Venn diagram of FIG. 8A. Neither diagnosis (A) nor diagnosis (B) accounts for all manifested clinical data (m), m=(1), . . . , (5). Moreover, clinical data (m) are not shared by different diagnoses (k).

Because all manifested clinical data (m) must be rationalized diagnosis (A) accounts for clinical data (1), (2), and (3), while diagnosis (B) accounts for clinical data (4) and (5). Diagnoses (A) and (B) are clearly concurrent and correspond to concurrent diseases (i). Concurrent diagnoses (A), (B) can be independently processed in separate differential diagnosis lists. With the same algorithm used for a single disease (i) more than one final diagnosis (k) will result. However, property (7) (8) of the mini-max procedure (see above) enables identification and separation of concurrent diagnoses (A), (B) in a single differential diagnosis list 34, superseding other more complicated methods.

Figure 8A:
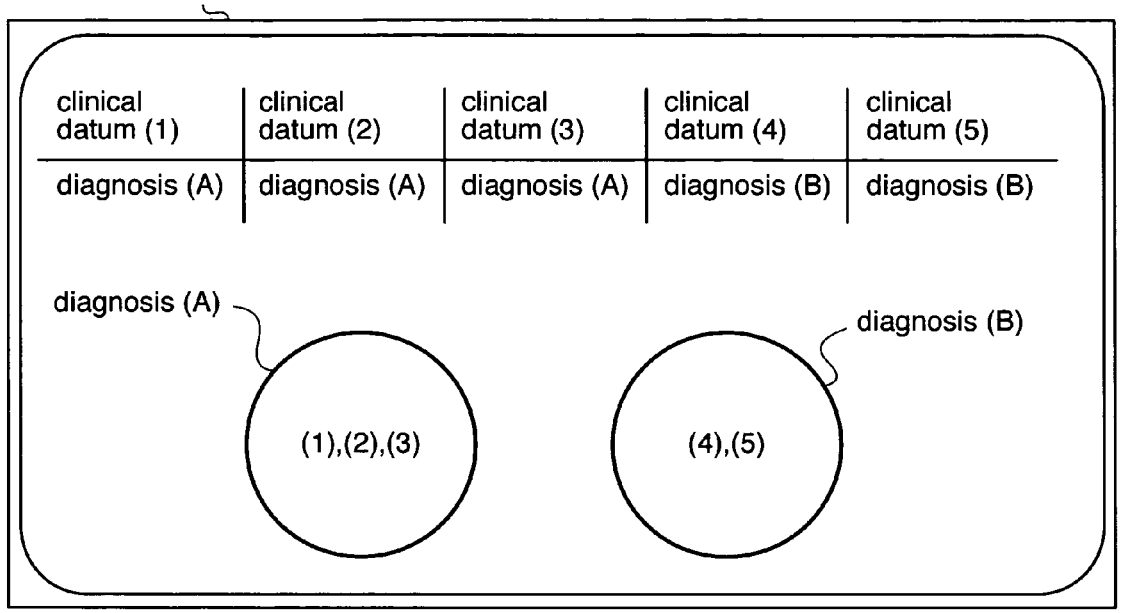
Figure 8B:
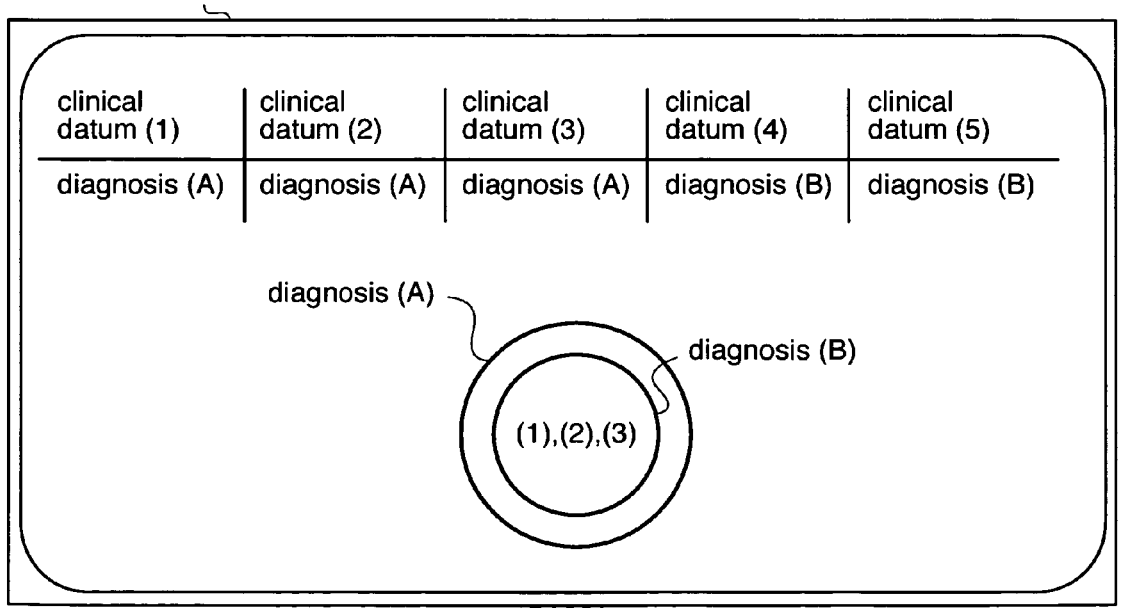
Figure 8C:
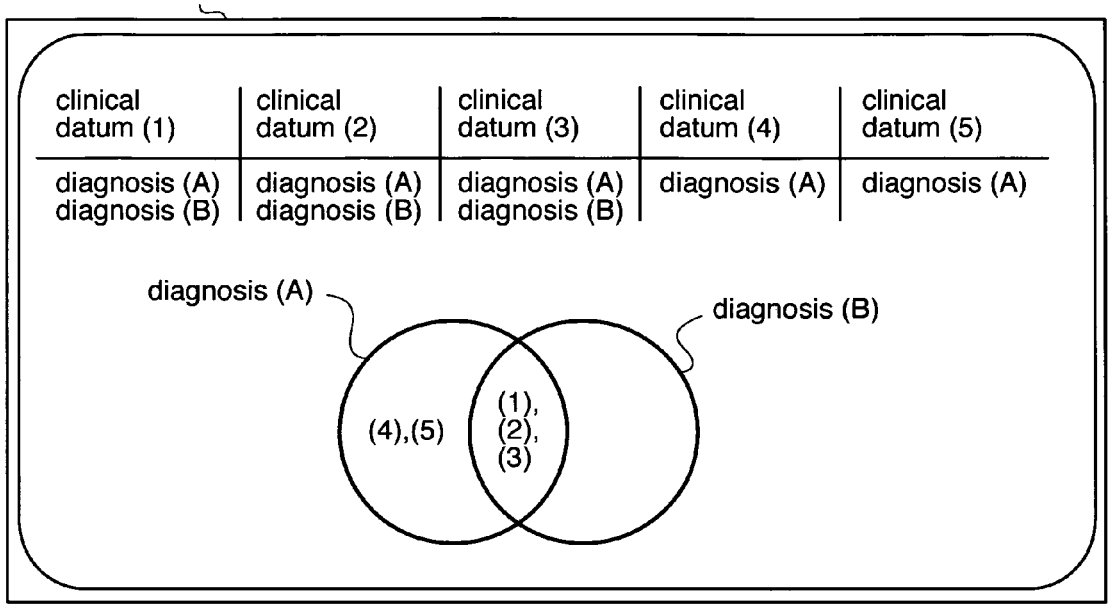

A second situation in which two diagnoses (A), (B) are totally overlapping is shown in the Venn diagram of FIG. 8B. These diagnoses (two or more in some cases) overlap completely. In other words, more than one diagnosis (i) accounts for all manifested clinical data (m) and all clinical data (m) are shared by these diagnoses (A), (B). In this situation, diagnoses (A) and (B) are likely to be competing diagnoses (k), because concurrent diseases (i) rarely manifest identical symptoms. When the difference among the greatest P value (leading diagnosis (k)) and the P values of the remaining diagnoses (k) is small, additional clinical data (m), as recommended by the best cost-benefit clinical datum (y) function, must be investigated for presence (j) or absence (r), so as to increase the difference to a significant level. This may be at increased cost C(y) to patient 26, if justifiable by the expected benefit.

Completely overlapping diagnoses (k) can represent either concurrent diseases (i) (unlikely) or competing diagnoses (i) (likely). This likelihood typically resolves as new clinical data (y) are obtained, resulting in the third situation (III) discussed below. Should close P values of two or more diagnoses (k) in differential diagnosis list 34 resist separation despite additional clinical data (y), concurrent diseases (i) must be suspected. When clinical datum (m) with PP value for a diagnosis (k) coexists with another clinical datum (m) with great PP value for another diagnosis (k), then this state of affairs reinforces the suspicion of concurrent diseases (i). When this occurs, the sum of the probabilities in differential diagnosis list 34 will be considerably greater than 1 (see property 7 of the mini-max procedure).

The third situation emerges when diagnoses (k) partially overlap. Certain clinical data (m) (here m=(1),(2),(3) in overlapping region) are shared by diagnoses (A), (B) while remaining clinical data (m) (specifically m=(4),(5)) are unshared. This occurs in the second situation when additional clinical data (m) are manifested in non-overlapping regions.

1. When a clinical datum (m) in a non-overlapping region belongs to only one diagnosis (k), whether the overlapping diagnoses (k) compete or are concurrent remains unclear because diagnosis (A) alone can account for all manifested clinical data (m) (m=(1), . . . , (5)). A Venn diagram illustrating partially overlapping diagnoses (A) and (B), with unshared clinical data (4), (5) in a single non-overlapping region is found in FIG. 8C.

Additional clinical data (y) are required to clarify this situation. Diagnosis (B) will be considered competing and will be ignored if its P is small because it does not account for all clinical data (m), whereas diagnosis (A) does. However, the PP value of clinical data (1), (2), (3) in the overlapping region may tip the scale in one or the other direction. If the PP value of any of these overlapping clinical data (m) is greater (more exclusive) for diagnosis (A) than (B), then (B) is more likely to be a competing diagnosis (k). Conversely, if PP value is greater for diagnosis (B) than (A), then diagnosis (B) is more likely to represent a concurrent disease (i). In other words, when the P of diagnosis (A) is greater than the P of diagnosis (B), the latter is competing; when the P of diagnosis (B) is greater than (A), the diagnoses (k) may be concurrent. The summed P values of all diagnoses (k) in differential diagnosis list 34 will considerably exceed 1 (see property 7 of mini-max procedure).

Figure 8D:
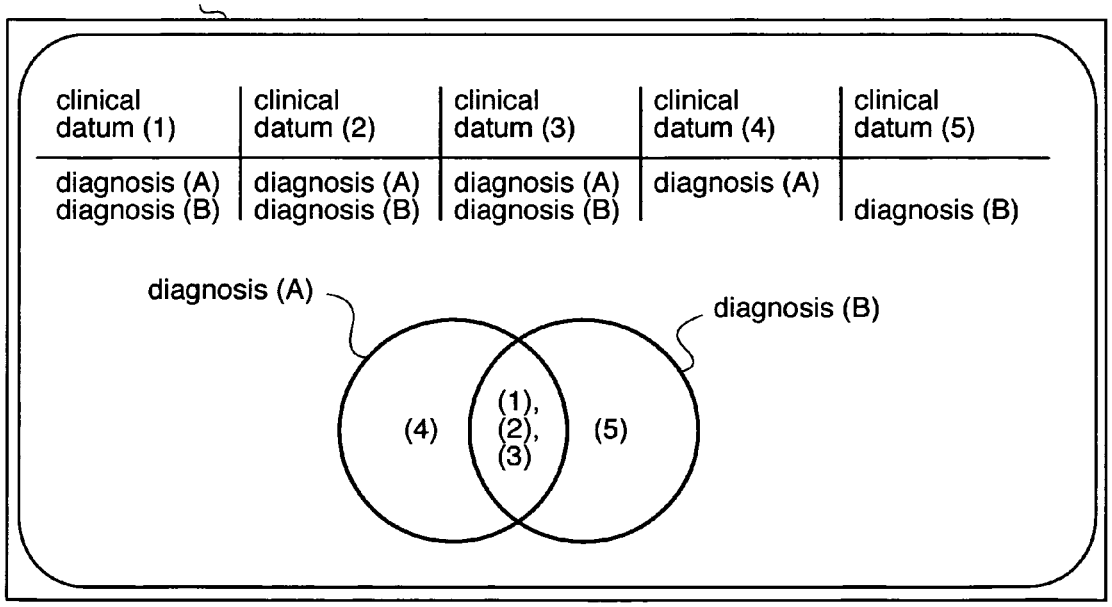

2. When partially overlapping diagnoses (k) include clinical data (m) in more than one non-overlapping region, those clinical data (m) belong to concurrent diagnoses (i). Diagnosis (A) accounts for clinical data (1), (2), (3) and (4) while diagnosis (B) accounts for clinical data (1), (2), (3) and (5). For example, Venn diagram in FIG. 8D shows partially overlapping diagnoses (A), (B) with unshared clinical data (4), (5) in more than one non-overlapping region.

Clinical data (m) (m=(1),(2),(3)) in the overlapping region could mean that diagnoses (A) and (B) only coincidentally share these data (m), but otherwise are unrelated (see unrelated concurrence, below). Alternatively, shared data (1),(2),(3) could mean a relationship between diagnoses (A) and (B) (see related concurrence, below) as in the example of metabolic syndrome, where insulin resistance is the shared clinical datum (m).

To confirm that diagnoses (A) and (B) are concurrent, the algorithm must search for unshared clinical data (4) and (5) each of which is exclusive to the respective disease (i) model.

When the PP value of a shared clinical datum (m) is greater for a specific diagnosis (k), that diagnosis (k) probably accounts for clinical datum (m). When the PP values of all shared clinical data (m) are greater for one diagnosis (k), the other diagnoses (k) compete. Conversely, when some PP values are greater for one diagnosis (k) and other PP values are greater for another diagnosis (k), those diagnoses (k) are concurrent.

Another reason to suspect concurrence of diseases (i) involves the mini-max procedure. Property 7 of the mini-max procedure states: when the summed P values of all diagnoses (k) in differential diagnosis list 34 substantially exceeds 1, some diagnoses (k) are likely to be concurrent. The greater the sum, the more concurrent diseases (i) exist.

Figure 8E:
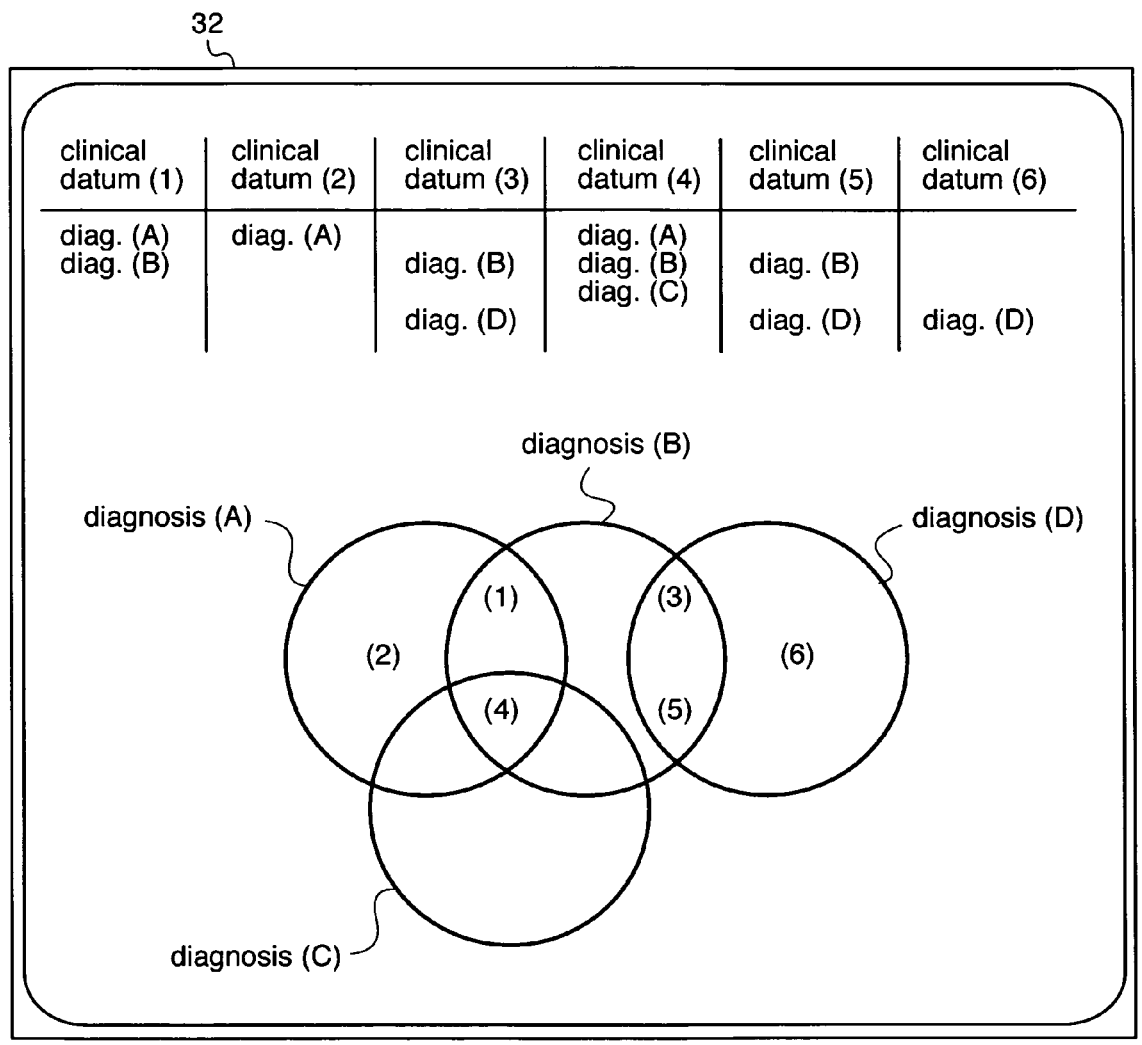

A fourth situation occurs when numerous overlapping diagnoses further complicate the diagnostic process, as depicted in FIG. 8E. Here the Venn diagram shows several partially overlapping diagnoses (A),(B),(C) and (D) with clinical data (m) in overlapping and non-overlapping regions. In this example, no single diagnosis (k) can account for all manifested clinical data (m). No diagnosis (k) is shared by all clinical datum lists; accordingly, some diagnoses (k) must be concurrent. One diagnosis (k) accounts for some clinical data (m); the remaining diagnoses (k) account for the remaining clinical data (m). In this example, four combinations of diagnoses (k) account for all clinical data (m), namely: (1) diagnoses (A), (B) and (D); (2) diagnoses (A) and (D); (3) diagnoses (A), (C) and (D); (4) diagnoses (A), (B), (C) and (D). Diagnoses (A) and (D) clearly concur because they do not overlap. Diagnosis (C) either competes or concurs with either diagnosis (A) or diagnosis (B) in a manner similar to situation three (III) point 1. Similarly, diagnosis (B) can either compete or concur with combined diagnoses (A) and (D). This latter combination alone also can account for all of the clinical data (m). Each concurrent disease (i) might have its own competing diagnoses (k). Concurrent diagnoses raise several questions. How does the algorithm identify concurrent diagnoses (k)? Summarizing what was discussed earlier, some facts signal concurrence: (a) No overlapping of diagnoses (no sharing of clinical data) categorically confirms concurrence. (b) No single diagnosis (k) will account for all manifested clinical data (m). (c) When concurrent diseases (i) exist, more than one diagnosis (k) with great P will remain atop differential diagnosis list 34. Processing additional clinical data (y) will not separate—and may even make closer—differences among these probabilities. (d) The sum of probabilities of diagnoses (k) in differential diagnosis list 34 will be greater than 1—typically closer to 2 or more—depending on the number of concurrent diseases (i). (e) In case of overlapping diagnoses (k), some of the shared clinical data (m) will stronger support one of the diagnoses (k) (greater PP values for this diagnosis (k)), while other clinical data (m) will stronger support the other diagnosis (k) (greater PP values for the other diagnosis (k)).

Conclusion of Diagnostic Quest

How does the mind of physician 24 or computer 12 detect that the diagnostic process is completed and that a final diagnosis best represents the disease (i) that afflicts patient 26? Several methods can determine when the conclusion of the diagnostic quest is achieved. The preferred method is the double threshold method.

Double Threshold Method

This method uses two empiric thresholds: a confirmation threshold CT and a deletion threshold DT. When the P of a diagnosis (k) in differential diagnosis list 34 is greater than confirmation threshold CT, such diagnosis (k) is transferred to a final diagnosis list (not shown). When the P of a diagnosis (k) in differential diagnosis list 34 is smaller than deletion threshold DT, such diagnosis (k) is ruled out and is deleted. The diagnostic quest concludes when differential diagnosis list 34 becomes empty.

Each concurrent final diagnosis requires a "clinching" clinical datum present (j) (with PP value close to 1). Competing diagnoses will need ruling-out clinical data absent (r). Very sensitive (S close to 1) clinical data absent (r) rule out diagnoses (k). For final diagnoses, P=1; for deleted diagnoses, P=0. In actual practice, such extreme values are not required; the confirmation and deletion threshold CT, DT values must be empirically determined.

These threshold values should be adjustable according to the severity of the condition of patient 26, favorable or unfavorable evolution, prognosis, and availability of efficient treatments. This problem may be related to a type of Receiver Operating Characteristic (ROC) curve that can be used to tune the diagnostic process. Decreasing confirmation threshold CT may erroneously confirm a diagnosis (k) of a disease (i) that does not afflict patient 26. Increasing it precludes this error, but may require costlier clinical data (m) to increase the P of diagnosis (k) to the level of this threshold CT. Increasing deletion threshold DT may erroneously rule out a diagnosis (k) of a disease (i) that afflicts patient 26. Decreasing it precludes this error, but may require costlier clinical data (m) to decrease the P of diagnosis (k), to the level of threshold DT.

Diseases and Drugs Interactions

Drugs often interact, one enhancing or reducing the effects of another. Drugs also may adversely alter clinical data (m) of a disease (i). In a somewhat similar manner, concurrent diseases (k) may interact, one enhancing or reducing (masking) a clinical datum (m) of another. Components (clinical entities) of a clinical presentation also can interact. Let's consider some examples:

Diabetes or advanced age may mask the chest pain of concurrent acute myocardial infarction.

An immunosuppressive drug (e.g., a corticosteroid) or disease (AIDS) may render negative an otherwise positive tuberculin reaction of concurrent tuberculosis.

The systolic hypertension may be reduced by concurrent acute myocardial infarction or shock.

Corticosteroids or antibiotics may suppress inflammatory symptoms of rheumatic diseases or appendicitis.

Disease and drug interactions are dangerous, because they can mask clinical data and result in misdiagnosis. This is especially important in the diagnosis of life threatening diseases (i).

When the affected clinical datum (m) in general is diminished in intensity or completely masked, as in the above examples; we are dealing with a clinical datum absent (r) that would otherwise be present (j) in disease (i). In the present diagnostic algorithm, the absence (r) of an expected clinical datum (m) tends to rule out disease (i) in direct proportion to the S of the datum (m). In the first example, chest pain in acute myocardial infarction has a great S (occurs very frequently.) With the Mini-Max Procedure, absence of chest pain (r), a consequence of concurrent diabetic neuropathy, would greatly reduce the P of myocardial infarction and could have dismal consequences. Accordingly, if a concurrent disease cancels clinical datum (m) of primary disease (i), the S of this clinical datum (m) must be proportionally reduced, to reduce its rule-out power.

A practical solution is to consider chest pain S=0 whenever myocardial infarction is suspected in a diabetic patient; this is equivalent to elimination of chest pain from diagnostic consideration. In this case the diagnosis of myocardial infarction must be achieved with other clinical data present (j) such as an ECG and cardiac enzymes.

Concurrent diseases or drugs typically interact with certain clinical data (m) only, which are flagged with interaction identifiers (Int) and pertain to specific diseases (i) only. Accordingly, in knowledge base 16, such concurrent diseases (i) and drugs are associated with these specific clinical data (m) in the specific disease (i) models.

When a clinical datum absent (r) of great S is processed, the algorithm checks whether it is flagged with an interaction identifier (Int). Interacting diagnoses (k) are added to differential diagnosis list 34. Preferably, physician 24 is also asked by computer 12 whether patient 26 is receiving specific drugs capable of interaction. When such an interacting diagnosis (k) or drug is confirmed, the S of the masked clinical datum (m) is reduced to zero and physician 24 is alerted of this fact.

Safety Checks

The algorithm embodying the medical analytics method running on computer 12 preferably includes safeguard routines to minimize the possibility of missing a diagnosis (k) because of failure to collect adequate clinical data (m) or to include the correct diagnosis (k) in differential diagnosis list 34.

First, the algorithm checks for clinical data (m) flagged with interaction identifiers (Int). This is accomplished when any diagnosis (k) including a clinical datum (m) susceptible to be masked and diagnosis (k) capable to mask are included in the same complex clinical presentation model.

Second, the algorithm checks for clinical data (m) flagged with risk identifiers (Rsk). This is accomplished automatically as the algorithm processes all clinical data present (j), risky or not. When a clinical datum present (j) is risk (Rsk) flagged, all diagnoses (k) capable of manifesting it are included in differential diagnosis list 34. Such diagnoses (k) are listed in the generated clinical datum list. When a clinical datum absent (r) is risk (Rsk) flagged, it can be disregarded unless also interaction (Int) flagged, in which case it must be established whether indeed absent (r) or masked.

Third, the algorithm checks for risk (Rsk) identifier flagged diagnoses (k). If a diagnosis (k) is risk (Rsk) flagged in a non-flagged clinical datum list, the algorithm must ensure its inclusion in differential diagnosis list 34. The algorithm includes all evoked diagnoses (k) in differential diagnosis list 34 and additionally it also includes all related diagnoses (k) listed in complex clinical presentation models. Once a final diagnosis is achieved, the algorithm searches the complex clinical presentation models for links to possible causes, evolutionary stage, complications, etc.; if a match is established, the related clinical entities of the model are included in differential diagnosis list 34 to be processed for existence.

Diagnoses Related to Patient Sex and Other Attributes

A diagnostic problem that arises is how the algorithm precludes diagnoses (k) that exclusively afflict only one sex—such as prostate diseases in men and ovarian diseases in women—from appearing in differential diagnosis list 34 of the opposite sex. In one embodiment, a routine included in the algorithm blocks this occurrence. In a preferred version of the algorithm this is unnecessary as the blocking occurs automatically because sex is considered a clinical datum (m) and is included in each disease (i) model with the corresponding PP value and S. Each male-exclusive disease model includes a "male sex" clinical datum (m) that has S=1 because it is always present in males, whereas PP value is very small (it is poorly characteristic) because many diseases afflict men. Likewise, each female-exclusive disease (i) model includes a "female sex" clinical datum with S=1 and very small PP value.

When a male-exclusive disease (i) (e.g., prostate cancer) is included in differential diagnosis list 34 of a female patient 26 (e.g., because of blood in urine), the algorithm will recommend "male sex" clinical datum (m) as the best cost-benefit clinical datum (y) because it has the greatest S=1 in S list 52. When this clinical datum (m) is noted absent (r) in female patient 26, the mini-max procedure will reduce the P of diagnosis (k) to zero and disease (i) will be eliminated from differential diagnosis list 34. A similar process occurs when a female-exclusive disease (i) (e.g., ovarian cyst) is included in differential diagnosis list 34 of a male patient 26. This confirms that the mini-max procedure can appropriately process a clinical datum absent (r), based on its S.

Preferably, age, race, occupation, and other attributes that influence the P of a diagnosis (k) are also considered clinical data (m) and processed in the usual way with the mini-max procedure. Of course, the P of diagnosis (k) will not be exactly 0 or 1, as with sex.

Diagnosis of Somatization and Malingering

Somatization and malingering typically generate many inconsistent clinical data (m) and clinical datum lists, but no diagnosis (k) is repeated in a majority of such lists. Convergence to a specific disease (i), syndrome, or clinical entity does not occur. The separation of differential diagnosis list P values typically experienced with physical diseases does not occur. Objective clinical data investigated by physical examination are absent; tests and procedures yield normal results.

Empiric Treatment

If two or more diagnoses (k) remain in differential diagnosis list 34, all of which are likely to respond to a single treatment, an empiric treatment may be warranted. If such treatment is successful, a more accurate but costlier final diagnosis (k) will be unnecessary. For example, when only a few rheumatic diagnoses (k) remain in differential diagnosis list 34, empiric treatment with corticosteroids may be justifiable.

Deferred Diagnosis

Therapeutic decisions often can be briefly deferred (Szolovitz and Pauker) when achieving a final diagnosis would be costly and competing diagnoses (k) are not immediately serious.

Meanwhile, patient 26 may manifest clarifying clinical data (m) or his disease (i) may spontaneously resolve. The best cost-benefit clinical data (y) function facilitates the decision to defer diagnosis (k) by alerting physician 24 when the cost category increments.

Example 1

Patient 26 presents with recent-onset fever. History 28 (see FIG. 1) and physical examination are otherwise normal. Symptomatic treatment for a few days is deemed adequate, while observing evolution of disease (i) that may be only a mild viral infection that may spontaneously resolve. Should patient 26 not improve, but his general condition remain stable, general blood and urine tests, a blood culture, and a chest X-ray are indicated. Should these moderate cost studies all be negative, empiric treatment with a broad-spectrum antibiotic can be started. Should the patient not respond, an intensive work-up to achieve an accurate final diagnosis would be indicated.

Example 2

Patient 26 complains only of recent-onset cough. This could be a mild bronchitis treatable with a cough suppressant and expectorant. However, should patient 26 not recover soon, other diagnoses (k) such as lung cancer must be considered.

Such cost-saving deferral of diagnosis (k) risks missing the opportunity to cure a serious disease (i). For this reason, observation should be brief, carefully monitored, and the cost-benefit issue clearly understood by patient 26.

Deferred diagnosis, empirical treatment, and other decisions required of physician 24 confronting disease (i) are not readily translated into the algorithm running on computer 12.

Advantageously providing the algorithm the necessary parameters—for example, patient age, general condition, potential seriousness of certain clinical data (m) or diagnoses (k)—Can enable computer assistance with such decisions. Physician 24 is alerted to risk-flagged (Rsk) clinical data (m) and diseases (k) and dangerous (or "panic") laboratory values, which could lead to a poor prognosis if not immediately addressed. Still, it is important to recognize that the present medical analytics method is only a helpful tool and needs to be used judiciously by physician 24.

Diagnosis by Exclusion

When clinical data (m) of great PP value that strongly support a diagnosis (k) are unavailable or too costly, the diagnostic process comes to a standstill. Physician 24 then can resort to diagnosis by exclusion where, from a group of competing diagnoses (k), all but one are excluded. The single remaining diagnosis (k) is accepted as a final diagnosis, even though its P is relatively small. Were we to apply our preferred double threshold method for concluding the diagnostic quest, the P of such a diagnosis (k) would not surpass confirmation threshold CT and accordingly would not be transferred to the final diagnosis list. Instead, it would remain alone in differential diagnosis list 34. All other diagnoses (k) would have been eliminated because the great S of corresponding clinical data absent (r) would have reduced their P below deletion threshold DT. For example the diagnosis of acute appendicitis is acceptable when all other causes of acute right lower quadrant abdominal pain and tenderness have been excluded. The opposite of a diagnosis by exclusion would be a diagnosis supported by a pathognomonic or "clinching" clinical datum (m) of great PP value that confers a high P to such an "assertive" diagnosis. An example is the diagnosis of tuberculosis when acid-fast bacilli are found in the sputum. The present algorithm automatically processes assertive and by exclusion diagnoses, once again illustrating the manner in which it emulates diagnosis by physician 24.

Complex Clinical Presentations and their Models

Throughout the interaction between physician 24 and patient 26, medical examination, tests, and procedures produces a jumble of clinical data (m), which must be coalesced and organized into final diagnoses.

The diagnostic process comprises several levels of complexity. Related clinical data (m) cluster to a syndrome, simple syndromes comprising only a few clinical data (m) coalesce to a complex syndrome or disease (i), and sometimes to a yet more complex clinical presentation, where the relation among clinical data (m) and diagnoses (k) becomes less obvious.

The embodiment of the algorithm thus far presented uses probabilistic calculations, with mini-max procedure, best cost-benefit clinical datum (y), and discrimination between competing diagnoses (k) and concurrent diagnoses (k), to determine the P of a final diagnosis.

It will work well with simple clinical entities, such as uncomplicated diseases (i) or syndromes where clinical data (m) typically are interrelated and linked to a single cause or lesion. Examples of such simple diseases (i) or clinical entities include bronchitis, asthma, gastroenteritis, hyperthyroidism, obstructive jaundice, and renal failure. At this diagnostic stage, a single final diagnosis accounts for all manifested clinical data (m). The accuracy of P depends on the accuracy of the S of clinical data (m). The computational time of this stage is not to be excessive (non-exponential.)

In actual patient 26, the clinical picture might be more complicated. As a fact, severely ill intensive care unit patient 26 often has multi-organ involvement, presents multiple and proteiform clinical data (m), and may mandate consultation by several specialists 24. For example, coronary artery disease, acute myocardial infarction, congestive heart failure, shock, and thromboembolism in single patient 26. A specific disease (i) can manifest diverse clinical forms and clinical presentations, complicating the diagnostic process. This situation makes it impossible to determine the S of each clinical datum (m) for the entire complex clinical presentation because this would involve multiple clinical forms, concurrent diseases (k), and multiple pathogenic and pathophysiologic mechanisms. It would require analyzing a statistically significant number of cases with identical combinations of clinical entities; it also would take us into an exponential or NP-complete computational time and complexity. Accordingly, probabilistic methods are unsuitable for processing any complex clinical presentation; indeed, no commercial diagnosis programs that can accomplish this task. A categorical method for processing complex clinical presentations is feasible, however.

For this reason a preferred embodiment of the present algorithm, with its heuristic principles and moderate use of probability, diagnoses first only relatively simple syndromes, clinical entities, or diseases (i). The algorithm produces as many final diagnoses of simple concurrent diseases (i), syndromes, complications, etc. as clinical data (m) dictate. The algorithm diagnoses satisfactorily these simple clinical entities and also recognizes concurrent diseases (i) or clinical entities. Once these partial components (clinical entities) are known, knowledge base 16 is conveniently augmented by categorical models (complex clinical presentation models; see below), one for each possible clinical interrelation or association of these entities: causal relations, evolutive stages, complications, severity, type, localization, etc. Such clinical presentation models, although numerous, are not excessive, and are described in the prior art, e.g., in any authoritative medical textbook. The algorithm selects the clinical presentation model that accommodates best all these "set of related entities". This diagnostic stage does not require a probabilistic approach, but a pure categorical one.

Categorically relating clinical entities based on their associated pathophysiologic links or statistical correlations, into a complex clinical presentation mandates creating a specific model for each possible combination. In accordance with standard practice, we will call these models complex clinical presentation models.

A complex clinical presentation model is therefore an abstract compilation or inventory of all possible relationships among diseases (i) or clinical entities. FIG. 9 shows an exemplary complex clinical presentation model 80. In this example the abbreviations are used as follows: CAD=coronary artery disease; MI-myocardial infraction; AF=atrial fibrillation. The dotted lines represent forbidden cross-links between complex clinical presentation models 80A-E.

These examples are incomplete. Not all linked clinical entities are shown. The direction of a causal link, when known, is indicated by an arrow. Complex clinical presentation model 80 should comprise only clinical entities that present a close pathophysiologic relationship or clear statistical correlation. When a clinical entity (e.g., atrial fibrillation in Examples 1 and 2) appears in diverse complex clinical presentation models (e.g., atrial fibrillation linked to myocardial infarction in one presentation model and linked to hyperthyroidism in another), such clinical entities should not be cross-linked. Dissimilar pathophysiologic mechanisms for such clinical entities may be involved in diverse presentation models. Such "trans-model" links (dotted lines) would result in undesirable entangled networks, as encountered in some diagnostic programs, and which greatly complicate implementation, utilization, and updating. Of all clinical entities that appear in the presentation models, only final diagnoses (italicized in Example 1) are displayed at the conclusion of the diagnostic quest.

Complex clinical presentation model 80 comprises related clinical entities and diseases (i); clinical data (m) are excluded from this definition because they are elements of a disease (i) model. Integration of each complex clinical presentation model 80 requires searching of such relationships in medical literature.

Should two or more final diagnoses be obtained, the question arises as to whether the respective diseases (i) are related or unrelated. When a relationship cannot be established the diseases (i) are unrelated concurrent. Example: tonsillitis and a uterine fibroid are unrelated concurrent diseases (i), because no known pathogenesis or pathophysiology relates them. When either a statistical correlation (mechanism unknown) or pathophysiologic relationship can be established, we call these diseases (i) related concurrent because actually they represent a single complex disease (i). An example is the metabolic syndrome that associates diabetes, obesity, dyslipidemia, hypertension, and vascular lesions. A statistical correlation among these diseases (i) initially was observed. Subsequent discovery of an underlying pathophysiologic common denominator (insulin receptor resistance) unified the apparently unrelated diseases (i) to a complex clinical presentation. Knowledge base 16 must be provided with complex clinical presentation models ideally listing all published categorical (as opposed to probabilistic) relations among clinical entities. When the final diagnoses of clinical entities fit into some of such complex clinical presentation models, they represent related concurrence; otherwise, they represent unrelated concurrence.

Many prior art algorithms employ tree and network structures that extend from cause of disease (i) to clinical data (m) and vice versa, placing probabilities on nodes, branches, and leaves. Most such structures are complex and required years to assemble. Such structures are difficult to update and would need to be redesigned every few years. In contrast, the present algorithm can relatively easily be updated at any time, by simply updating in disease (i) models the S values of clinical data (m), adding or deleting clinical data (m) when necessary, or adding or deleting disease (i) models. Occasionally, the list of clinical entity combinations in the complex clinical presentation models must be modified when new associations are discovered.

In summary, the entire diagnostic process is achieved in 2 steps:

Step 1. Probabilistic processing of clinical data (m) matches patient 26 clinical data (j),(r) with clinical entity model clinical data (m), yielding differential diagnosis list 34. Mini-Max procedure, best cost-benefit clinical data (y) next to investigate, safety checks for interaction and risk identifiers, and discrimination between competing diagnoses (k) and concurrent diagnoses (k) achieves as many concurrent final diagnoses of clinical entities as are required to account for all manifested clinical data. Then, the algorithm proceeds to Step 2.

Step 2. Categorical processing of clinical entities
Step 2.1. Each time a diagnosis (k) is confirmed as final, it is compared to each diagnosis (k) in each of all complex clinical presentation models 80 and if a match is found, all the remaining diagnoses (k) in this complex clinical presentation model 80 are included in differential diagnosis list 34 to be processed for presence (j) or absence (r) in patient 26. This precludes overlooking diagnoses. Example: a final diagnosis (e.g., pneumothorax) is confronted with all complex clinical presentation models in knowledge base 16. Related clinical entities (e.g., tuberculosis, emphysema, or lung cancer) occurring in matching models are included in differential diagnosis list 34 to be processed for their presence G) or absence (r) in patient 26.

Figure 28:
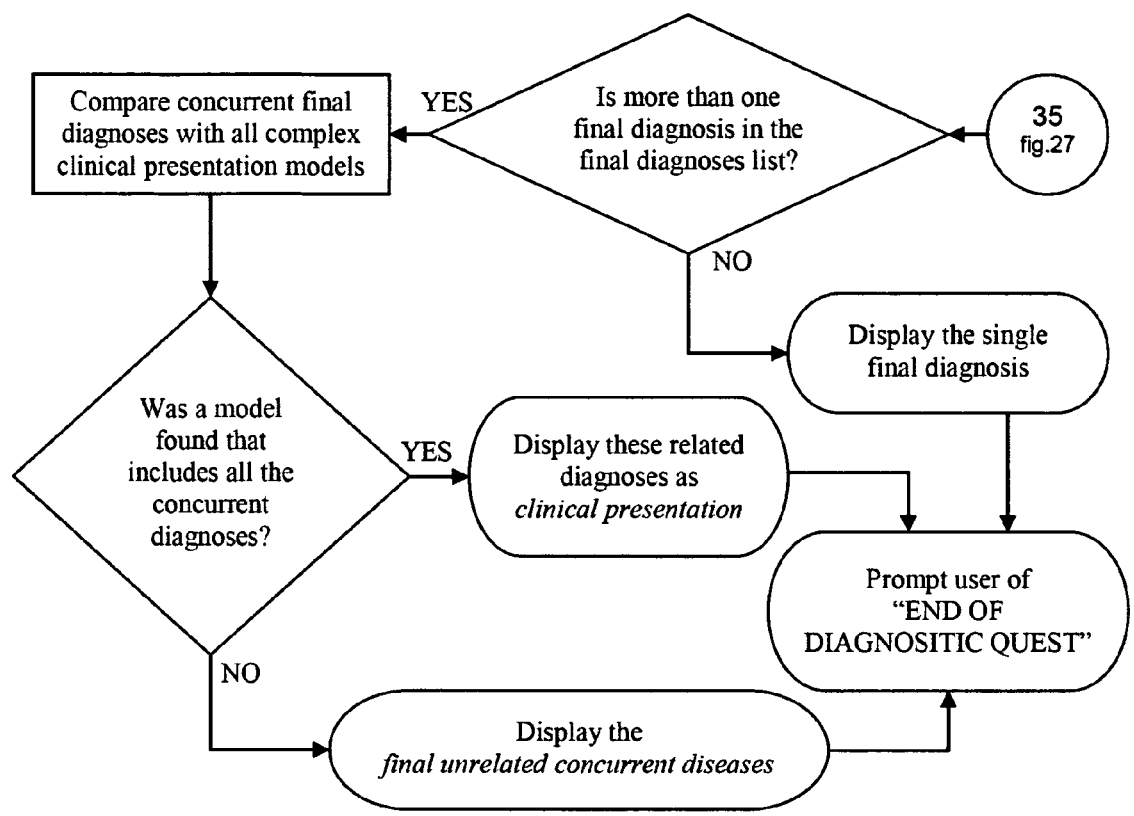

Step 2.2. Establishing related or unrelated concurrency of clinical entities: When two or more clinical entities are confirmed as final diagnoses, they are compared to all clinical presentation models in knowledge base 16. When no complex clinical presentation model linking two or more clinical entities exists, such clinical entities appear on display 32 as unrelated concurrent diagnoses (k), and the diagnostic quest concludes. When such a complex clinical presentation model exists the clinical entities are displayed as related concurrent (k), and the diagnostic quest concludes (FIG. 28).

Several situations may occur when matching and selecting clinical presentation models:

When more than one clinical presentation model is matched, that which links the greatest number of confirmed final diagnoses will be selected to account for the complex clinical presentation.

When two or more clinical presentation models link a like number of confirmed final diagnoses, all such models will be selected as alternative representations of the complex clinical presentation.

When diagnosed clinical entities match only some entities of the complex clinical presentation model, this nevertheless suffices to select the model and link the clinical entities. For example, not all complications listed in a single complex clinical presentation model need be matched; one complication (e.g., pneumothorax) and one cause (e.g., emphysema) suffice to link these two clinical entities.

When one set of diagnosed clinical entities matches one clinical presentation model, while another set matches another clinical presentation model, the sets do not share clinical entities and the two clinical presentations are concurrent.

When clinical presentation models involve clinical entities that are related in opposite directions (e.g., myocardial infarction→shock; or shock→myocardial infraction), such alternatives are displayed and the user selects the direction that is most consistent with the clinical picture.

Remarks about Particularly Advantageous Embodiments of the Knowledge Base

A preferred way of integrating knowledge base 16 with system 10 (see FIG. 1) involves providing the following elements:

Create a disease (i) model for each currently known clinical entity and disease (i), including all clinical data (m) that potentially can be manifested. Disease (i) models for diseases (i) influenced by, or related to age, gender, race, occupation, or any other demographic factor, should include such factors, considering them as clinical data (m) with their corresponding S, PP value, risk and interaction identifiers.

Disease (i) models and clinical datum lists are conveniently visualized by entering them in an huge virtual table where the several thousand known diseases (i) are listed in the heading row and the several thousand known clinical data (m) are listed in the first column (see an exemplary embodiment of an appropriate Virtual Table below).

| Cost ++++ | Tuberculosis* | Bronchitis |
|---|---|---|
| Cough + | S = 0.83 | S = 0.95 |
| | PP value = 0.7 | PP value = 0.8 |
| Hemoptisis +* | S = 0.7 | S = 0.05 |
| | PP value = 0.55 | PP value = 0.01 |
| Dyspnea +* | S = 0.5 | |
| | PP value = 0.4 | |
| Fever +& | | |

VIRTUAL TABLE legend:
+ - no cost;
++ - small cost;
+++ - intermediate cost;
++++ - great cost;
* - risk identifier;
& - interaction identifier.

The cell, in which each diagnosis (k) and its corresponding clinical datum (m) converge, shows S and PP value of clinical datum (m) for disease (i). Many cells will show S=0 and PP value=0, meaning that clinical datum (m) is never manifested by disease (i). These "empty" cells can be disregarded. After disregarding empty cells, each column represents a disease (i) model and each row represents a potential clinical datum (m) list. Each clinical datum (m) shows its cost category. Risk identifiers (Rsk) are flagged with an asterisk (*). Interaction identifiers (Int) are flagged with an ampersand (&) in the cells of clinical data (m) potentially modifiable by drugs or concurrent diseases (i).

Create complex clinical presentations models for all possible combinations of clinical entities and diseases (i).

Create a dictionary with common synonyms for clinical data (m).

Calculate the PP value of every clinical datum (m), based on the S value, according to Eq. 2.

Create four cost to obtain clinical data categories: none, small, intermediate, and great. Estimate cost C(m) of each clinical datum (m), assign it to the appropriate category, and include it in knowledge base 16.

Link each disease (i) model with the cause of disease (i), when known; pathogenesis; pathology; pathophysiology; syndromes; complications, including those that are iatrogenic; stages; interactions with other diseases (i) and drugs; prognosis and treatment. Link any other information related to disease (i). These links enable retrieving information that is related to other information in knowledge base 16.

Establish empiric values for confirmation and deletion thresholds CT, DT adjustable to the circumstances of the specific case: diagnostic uncertainty; disease severity, evolution, and prognosis; and efficacious treatment availability.

Create routines to update, edit, or delete information in knowledge base 16.

A Practical Embodiment of the Algorithm for Implementing the Medical Analytics Method on a Computer Implementation of medical analytics method in the form of an algorithm for execution on computer 12 can be performed in many ways. A person skilled in the art will recognize that many programming options exist and various data structures are amenable to the present algorithm. The below explanation in relation to FIGS. 10-28 shows one advantageous manner of implementing the medical analytics method of the invention in the form of a computer program to be run on computer 12 in connection with network 18 and knowledge base 16. The main flowchart of the diagnostic algorithm implementing the medical analytics method of the invention and the various routines and aspects of the method explained above will now be explained in strict reference to the corresponding drawing figures.

Figure 10:
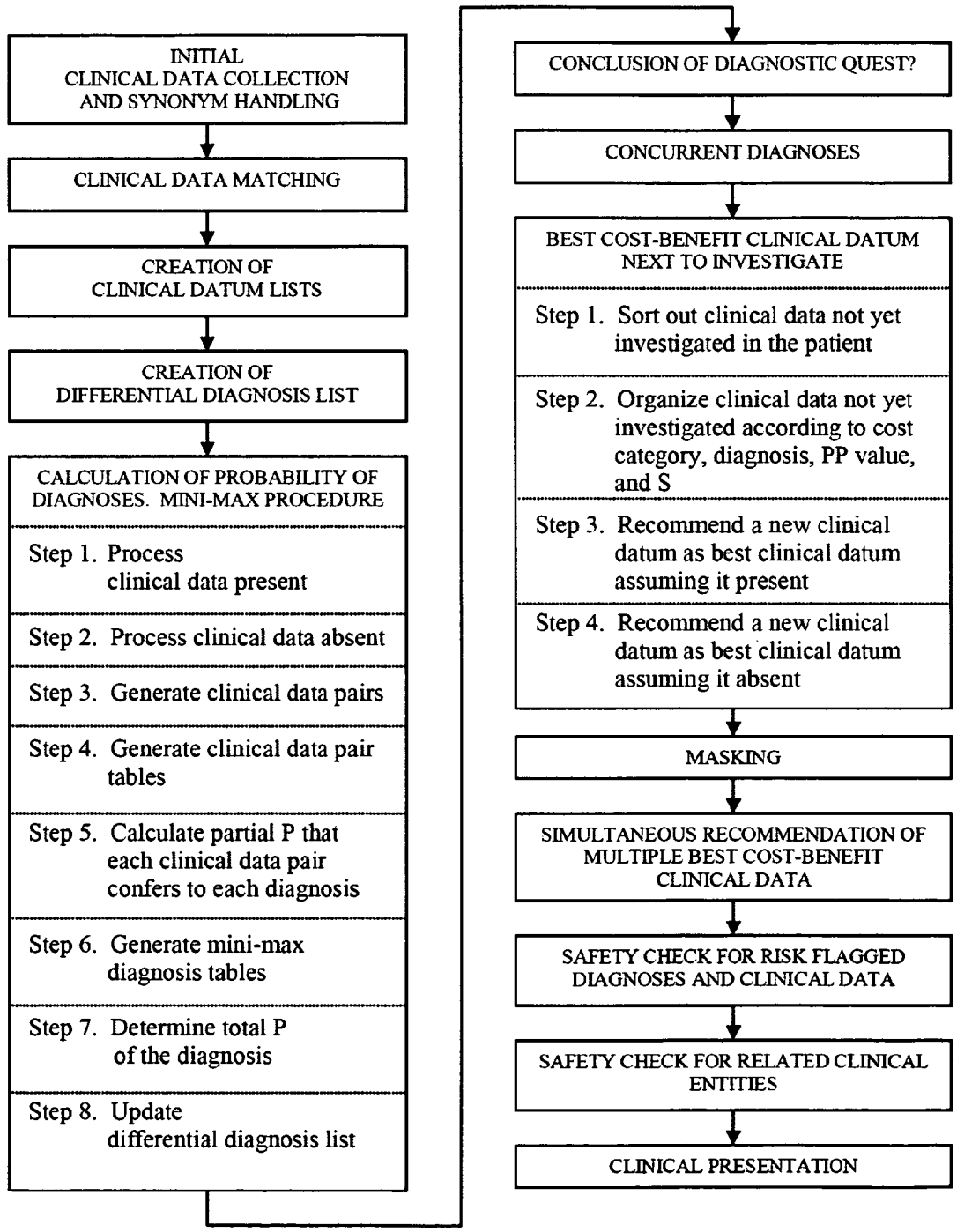

FIG. 10 presents a main flowchart of the diagnostic algorithm. The diagnostic algorithm executes successive steps via several routines shown in detail in subsequent drawing figures.

FIG. 11 explains the initial collection of clinical data (m) and synonym checking. In this routine computer 12 is provided with general information about patient 26, followed by initially collected clinical data (m). It prompts physician 24 to indicate whether each clinical datum is present (j) or absent (r). Clinical data present (j) will create clinical datum lists; clinical data absent (r) are stored for future use in ruling out diagnoses (k).

When a putative clinical datum is not matched with a clinical datum (m) in any disease (i) model, search in knowledge base 16 for a standard synonym. If a synonym is found, it is processed; if a synonym is not found, physician 24 is prompted to try another term for the unidentifiable clinical datum.

Figure 12:
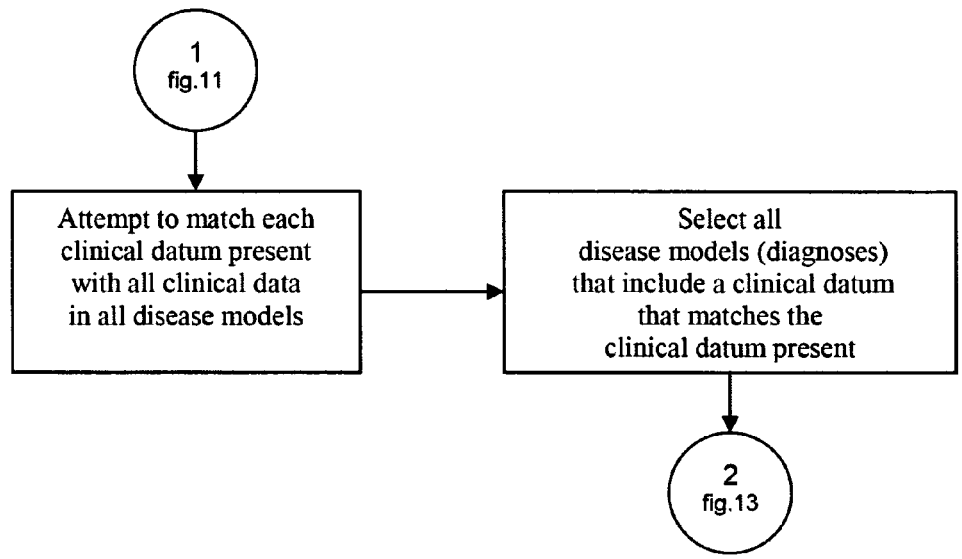

FIG. 12 illustrates the matching of collected clinical data present (j) with clinical data (m) in disease (i) models. Here, each clinical datum present (j) is compared with clinical data (m) listed in each disease (i) model. All disease (i) models (diagnoses (k)) that show a match are selected.

Figure 13:
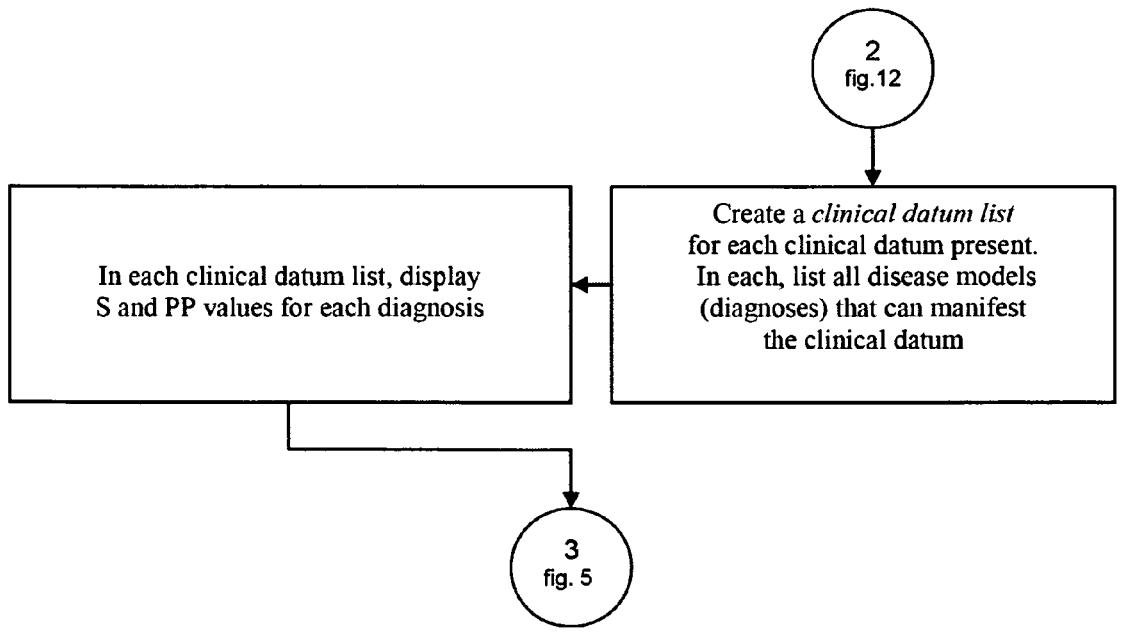

FIG. 13 details the creation of clinical datum lists. These steps involve creating a clinical datum list headed by the name of clinical datum (m), followed by all diagnoses (k) that could manifest it. Then, S and PP values of this clinical datum (m) for each diagnosis (k) are arranged by decreasing numerical value.

Figure 14:
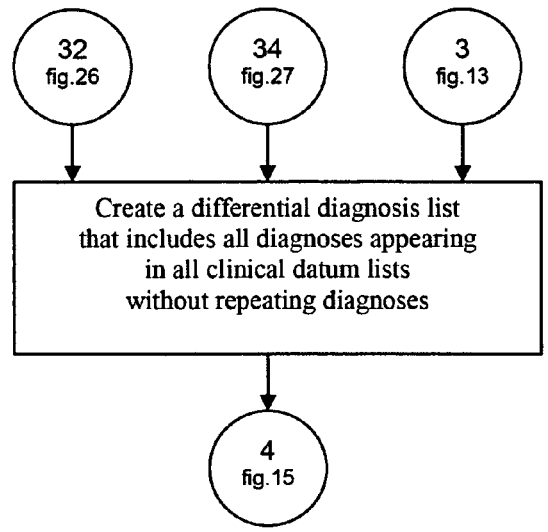

FIG. 14 shows the creation of differential diagnosis list 34. The differential diagnosis list is created such that it includes all diagnoses (k) appearing in all clinical datum lists without repeating diagnoses.

FIGS. 15-18 refer to probabilities of diagnoses and the Mini-Max Procedure.

Figure 15:
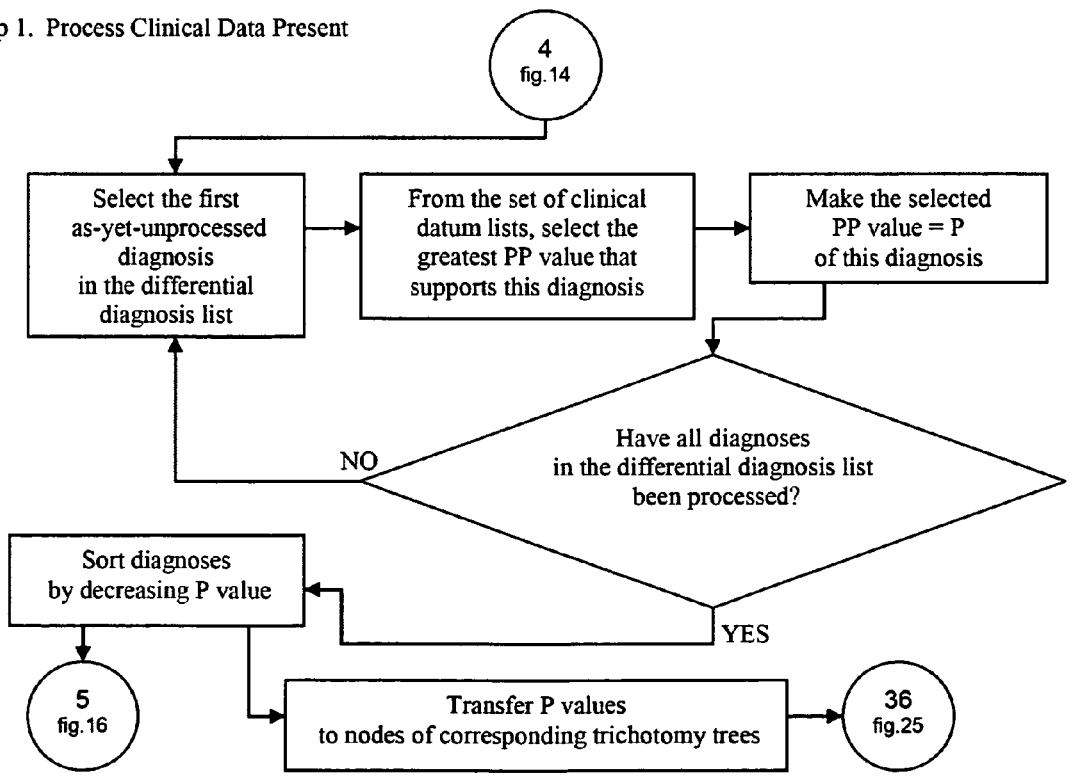

FIG. 15. Step 1. Processing of clinical data present (j). For each diagnosis in differential diagnosis list 34, select from the set of clinical datum lists the clinical datum with the greatest PP value that supports this diagnosis. The selected greatest PP value equals the P of this diagnosis. This value can be modified by clinical data absent (r) (next steps).

Figure 16:
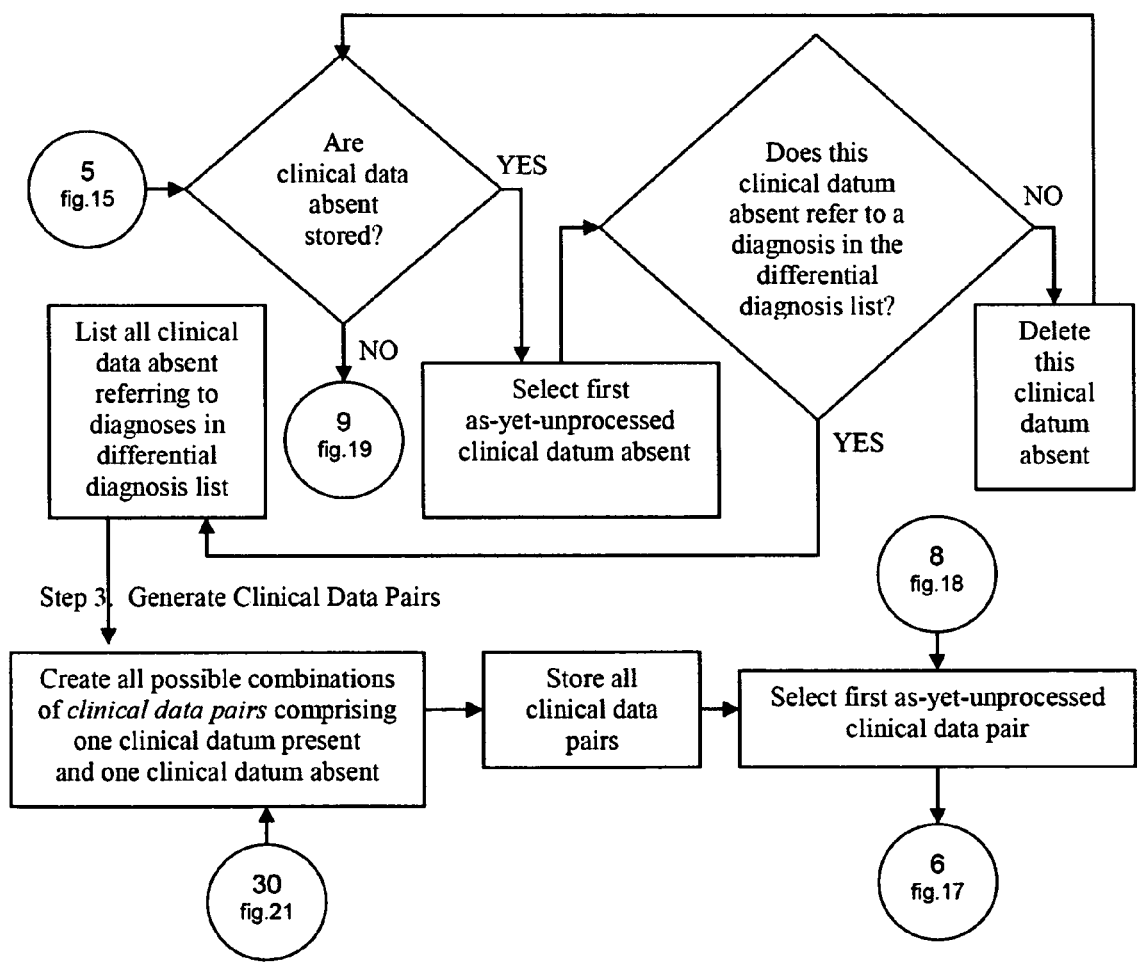

FIG. 16. Step 2. Processing of clinical data absent (r). Delete clinical data absent (r) (obtained from patient 26 history) that do not refer to diagnoses (k) in differential diagnosis list 34.

Step 3. Creation of clinical data pairs (j, r). Create clinical data pairs (j, r) comprising all possible combinations of one clinical datum present (j) and one clinical datum absent (r).

Figure 17:
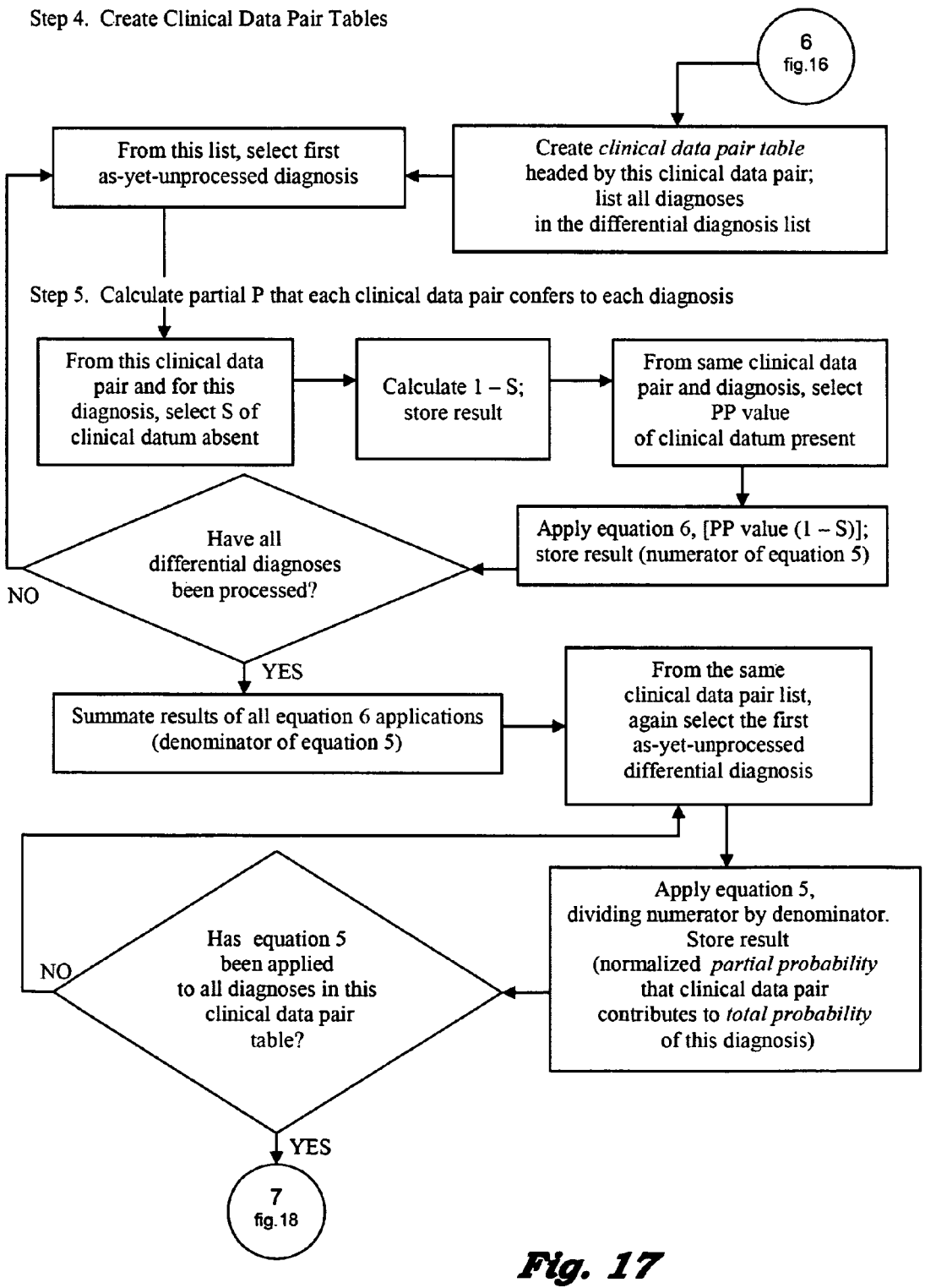

FIG. 17. Step 4. Creation of clinical data pair tables. Each table is headed by the respective clinical data pair (j, r), and lists all differential diagnoses (k).

Step 5. Calculation of partial P that each clinical data pair (j, r) confers to each differential diagnosis (k). First, for each diagnosis in each clinical data pair table, apply Eq. 6 to PP value of clinical datum present and S of clinical datum absent. This yields the numerator for Eq. 5, which is then applied to each diagnosis (k), yielding the partial P values that will contribute to the total P of the respective diagnosis. In each clinical data pair table the diagnoses are listed in the first column and the resultant partial P values are shown at the extreme right side of the second column.

Figure 18:
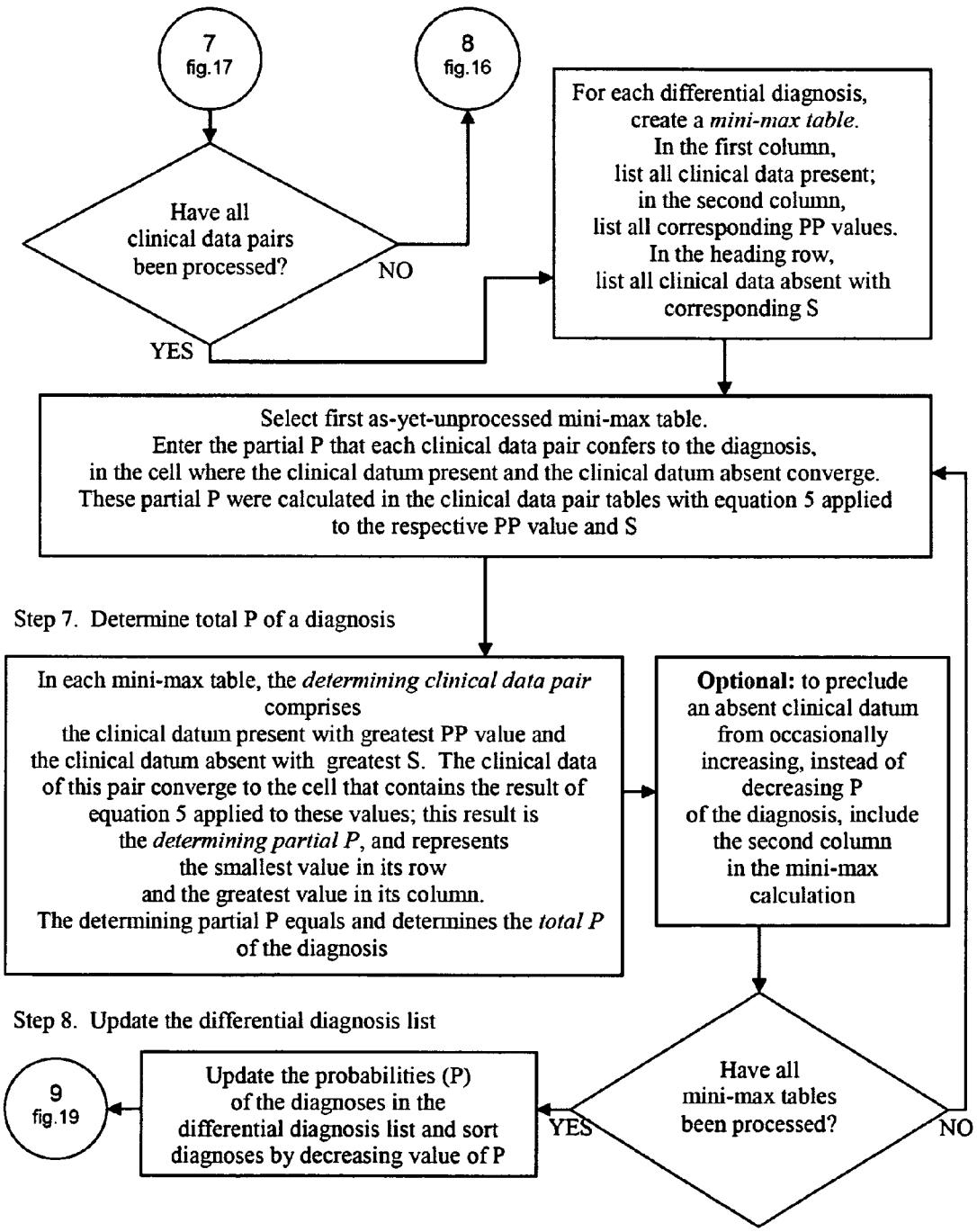

FIG. 18. Step 6. Creation of Mini-Max Tables 38(k) (see also FIG. 41). Create, for each diagnosis (k) in differential diagnosis list 34, a Mini-Max Table 38(k) that shows for title the name of the corresponding diagnosis (k). The first column 38B(k) lists all clinical data present G). The first data column 38A(k) lists the corresponding PP values of these clinical data present (j); its bottom cell repeats the greatest of these values, which is the P of the diagnosis (k) before clinical data absent (r) are considered. The heading row lists all clinical data absent (r). The next several columns show the partial P values that each clinical data pair (j, r) confers to diagnosis (k). The number of these columns equals the number of clinical data absent (r). The heading of each column shows the clinical datum absent (r) and its S for the diagnosis (k). Each partial P value is transferred from the clinical data pair tables to the Mini-Max Table cell where the clinical data present (j) and absent (r) converge. The bottom cell of each column repeats the greatest partial P value appearing in the column. The last column repeats the smallest value appearing in each row. The bottom cell of this column, which also is the last cell of the Mini-Max Table, repeats the greatest value of the column; it equals the total P of the diagnosis, after clinical data absent (r) have been considered.

Step 7. Determination of total probability TP(k) of diagnosis (k). In each Mini-Max Table 38(k), the clinical data pair (j, r) containing the clinical datum present (j) with the greatest PP value and the clinical datum absent (r) with greatest S is called determining clinical data pair. The clinical data of this pair converge to the cell that contains the result of Eq. 5 applied to these values. This result is called determining partial $DP(k)_{j,r}$, which is the smallest value in its row and the largest in its column. The value of the determining partial P equals and determines the total TP(k) of this diagnosis (k). Sometimes, TP(k) of a diagnosis (k), instead of being decreased by a clinical datum absent (r), as expected, is actually increased. One has the option to preclude this effect by including the first data column in the mini-max calculation.

Step 8. Updating differential diagnosis list 34. The P of the diagnoses (k) in differential diagnosis list 34 are updated and sorted by decreasing values of P.

Figure 19:
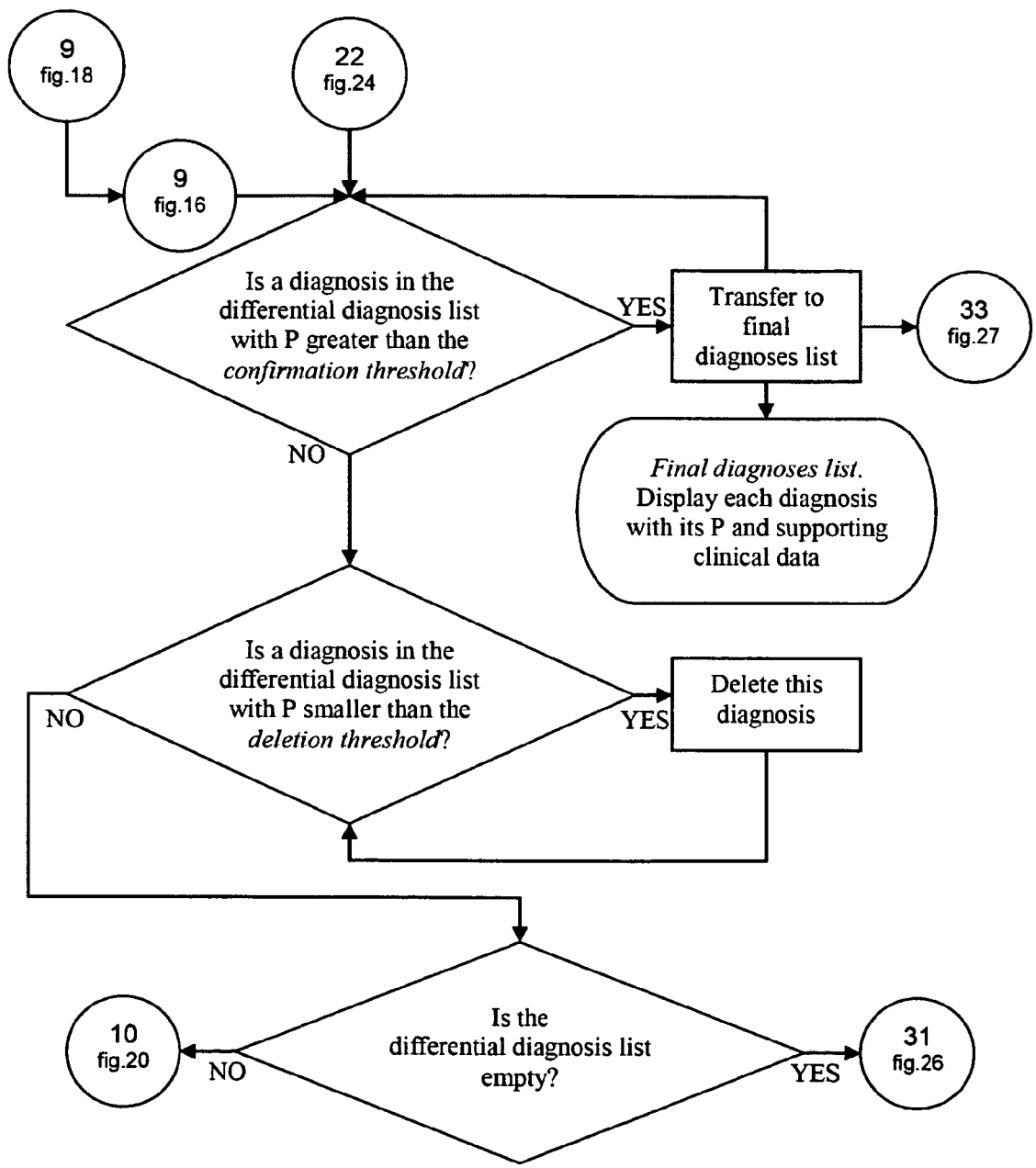

FIG. 19. Conclusion of diagnostic quest. Two empiric thresholds are included in the knowledge base: confirmation threshold CT and deletion threshold DT. Each diagnosis (k) is checked to ascertain whether its P has reached confirmation threshold CT (diagnosis is transferred to final diagnoses list) or has reached deletion threshold DT (diagnosis is deleted.) When no diagnoses (k) remain in differential diagnosis list 34, the algorithm goes to routines ensuring that no other diagnoses (k) were overlooked. These routines check for risk (Rsk) flagged diagnoses and clinical data (FIG. 26), and clinical entities related with the final diagnoses (FIG. 27). When one or more diagnoses (k) remain in differential diagnosis list 34, the algorithm goes to the next routine (FIGS. 20 through 23).

FIGS. 20 through 23. Best cost-benefit clinical datum (y) next to investigate.

Figure 20:
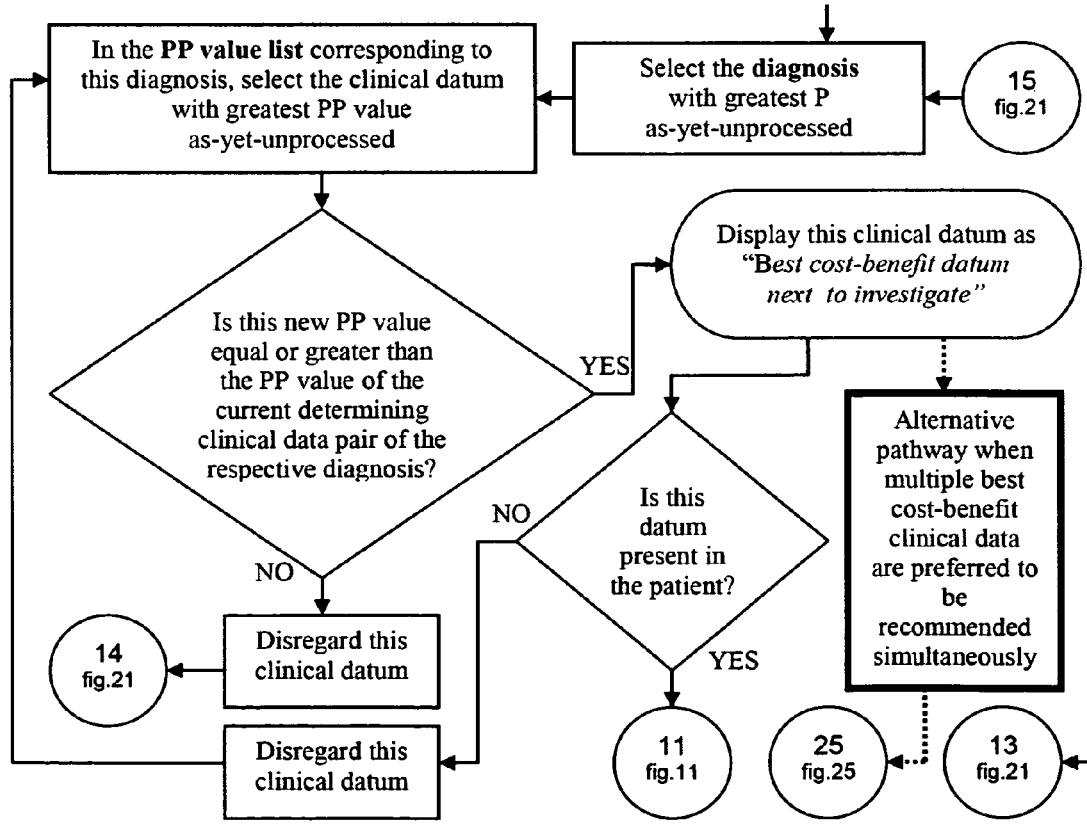

FIG. 20. Step 1. Select clinical data not yet investigated (y) in patient 26. From the disease (i) models of all diagnoses (k) in differential diagnosis list 34, select all remaining clinical data not yet investigated (y).

Step 2. Organize clinical data not yet investigated (y) according to cost category, diagnosis, PP value, and S. These clinical data (y) are distributed among four cost categories (none, small, intermediate, and great.) In each category, diagnoses (k) in differential diagnosis list 34 are sorted by decreasing P. For each diagnosis (k) and cost category, the corresponding clinical data (y) are sorted by decreasing PP value in one list (PP list 50; see FIG. 5), and the same data (y) by decreasing S in another list (S list 52; see FIG. 5)

Step 3. Recommend a best cost-benefit clinical datum (y) assuming it present (j), i.e., treating that clinical datum (y) as if it were present (j). The routine moves to the lowest as-yet-unprocessed COST category, selects the as-yet-unprocessed DIAGNOSIS with greatest P, and from the corresponding PP LIST 50, selects the as-yet-unprocessed clinical datum (y) with the greatest PP value. This PP value then is compared to the PP value of the clinical datum present (j) in the current determining clinical data pair. New clinical data with equal or smaller PP value are disregarded because—even if present (j)—they will not change the current P of this diagnosis (k). Accordingly, the routine moves to Step 4. When the PP value of a new clinical datum exceeds the current P of the diagnosis before considering clinical data absent (r) (bottom cell of second column of the mini-max table), the algorithm recommends this best cost-benefit clinical datum (y). If physician 24 verifies the recommended best cost-benefit clinical datum (y) as present (j), a new clinical datum list and several new clinical data pairs (j, r) are created, a new row is inserted in each pertinent mini-max table 38(k), and the partial P of the diagnosis (k) assumes the new PP value. The total P of the diagnosis (k) then is recalculated. If physician 24 verifies the recommended best cost-benefit clinical datum (y) as absent (r), it will be disregarded. Step 3 is iterated until the PP value of a clinical datum in the PP value list does not exceed the current P of the diagnosis (k).

FIG. 21. Step 4. Recommend a best cost-benefit clinical datum (y) assuming it absent (r). From S LIST 52 corresponding to the same COST category and DIAGNOSIS (k), the routine selects the as-yet-unprocessed clinical datum (y) with the greatest S; this clinical datum (y) then replaces the existing corresponding datum absent (r) in the determining clinical data pair, thereby creating a new clinical data pair.

Figure 22:
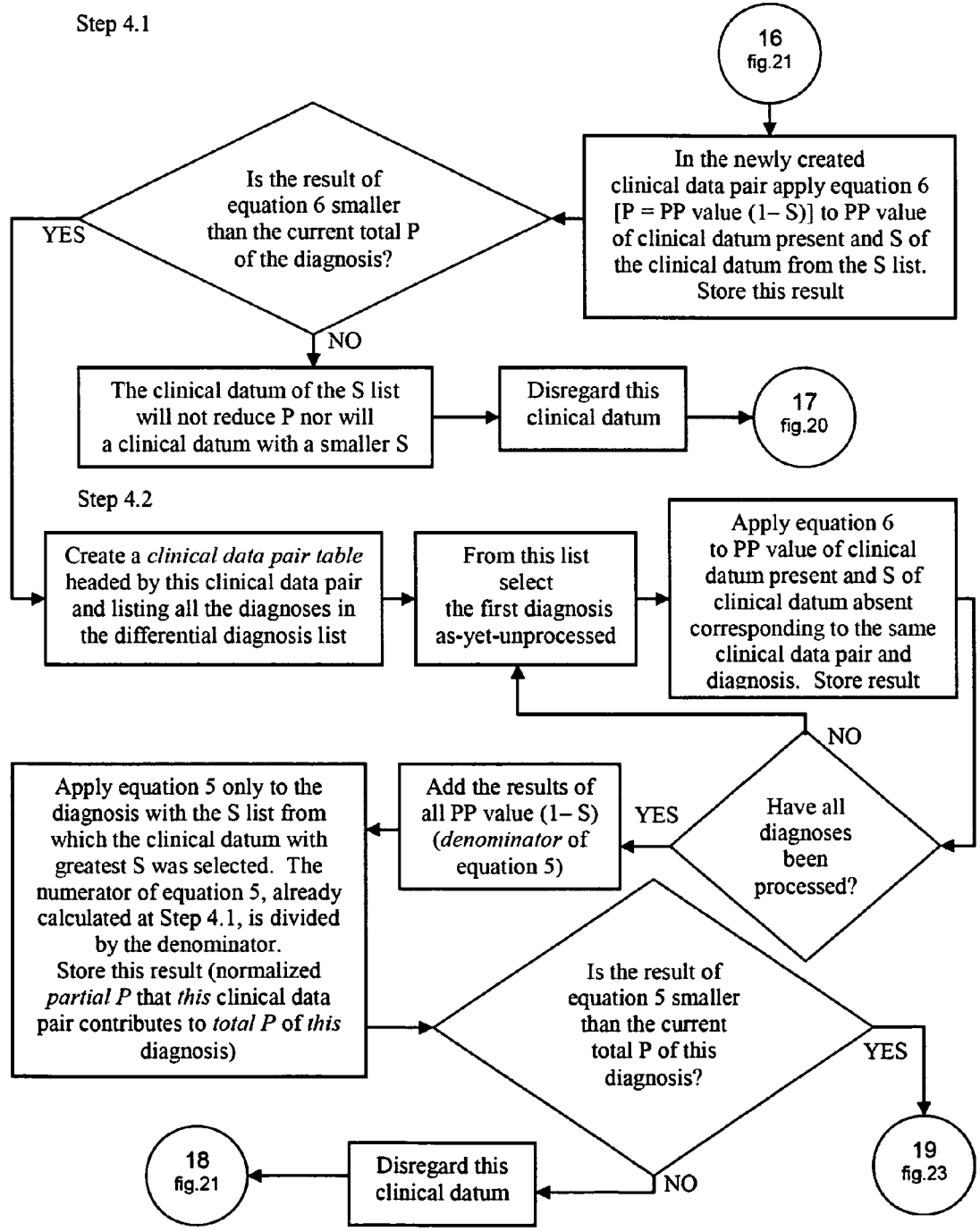
Figure 23:
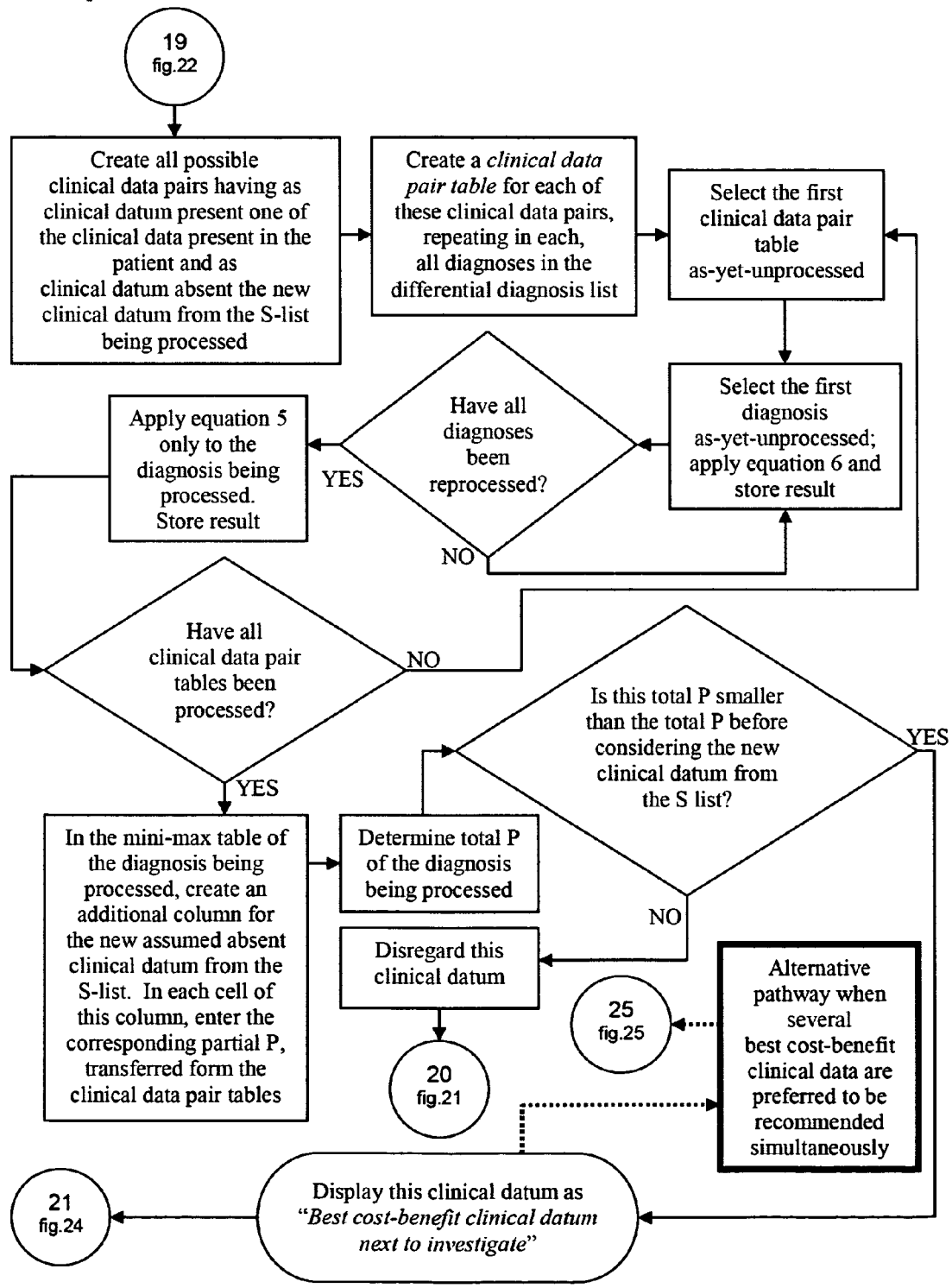

FIGS. 22 and 23. 3-Step method to predict whether a new clinical datum absent (r) will decrease total probability TP(k).

FIG. 22. Step 4.1 Eq. 6 is applied to the PP value and S of the newly created clinical data pair (j, r). If the resulting partial P equals or exceeds the current total probability TP(k) of diagnosis (k), neither this nor any other clinical datum (y) in the same S list 52 will decrease the TP(k). Accordingly, Steps 4.2 and 4.3 become unnecessary and the routine advances to the next diagnosis. If the resulting P is smaller, the TP(k) of diagnosis (k) under consideration may or may not decrease; proceed to Step 4.2.

Step 4.2 A clinical data pair table is generated for the newly created clinical data pair (j, r) of step 4.1. This table is headed by this clinical data pair (j, r) and lists all the diagnoses (k) in differential diagnosis list 34. Now Eq. 5 is applied only to the diagnosis (k) being processed; its numerator is as calculated by Eq. 6 applied in Step 4.1. The denominator is the sum of terms, each of which is the result of iterating Eq. 6 applied to the same clinical data pair (j, r) but with PP values and S corresponding to each diagnosis (k) in the clinical data pair table. The result of Eq. 5 is the normalized partial P of diagnosis (k)

being processed. A new column could be created in mini-max table 38(k) corresponding to the diagnosis (k), but only one of its cell can be filled with the calculated partial P. If the resulting partial P equals or exceeds the current TP(k) of diagnosis (k), the new clinical datum (y) will not decrease TP(k). Step 4.3 becomes unnecessary for this clinical datum (y). However, another new clinical datum (y) from S list 52, even with a smaller S, still might decrease TP(k). To verify the latter, the next new clinical datum (y) from S list 52 must be tested by stage 4.1 until it fails, at which time the routine moves to the next diagnosis (k). Conversely, if the resulting partial P is smaller than the current TP(k) of diagnosis (k) under consideration, the latter may or may not decrease. Proceed to step 4.3.

FIG. 23. Step 4.3 All possible new clinical data pairs (j, r) are created, each comprising an existing clinical datum present (j) and the new clinical datum absent (r). As in stage 4.2, Eq. 6 is applied to all diagnoses (k). Eq. 5 then is applied to the diagnosis (k) being processed, but in this step to all clinical data pair tables. The calculated partial P values that the new clinical data pairs (j, r) confer to the diagnosis (k) appear in all cells of a new column created for the clinical datum absent (r), in the mini-max table 38(k). TP(k) of diagnosis (k) is determined. If the new TP(k) is smaller than the existing TP(k), the new clinical datum (y) from S list 52 is recommended as the best cost-benefit clinical datum (y) next to investigate. Otherwise it is disregarded and the algorithm processes the next clinical datum (y) in S list 52. The 3-Step method processes each diagnosis (k) in differential diagnosis list 34 in a similar way.

Figure 24:
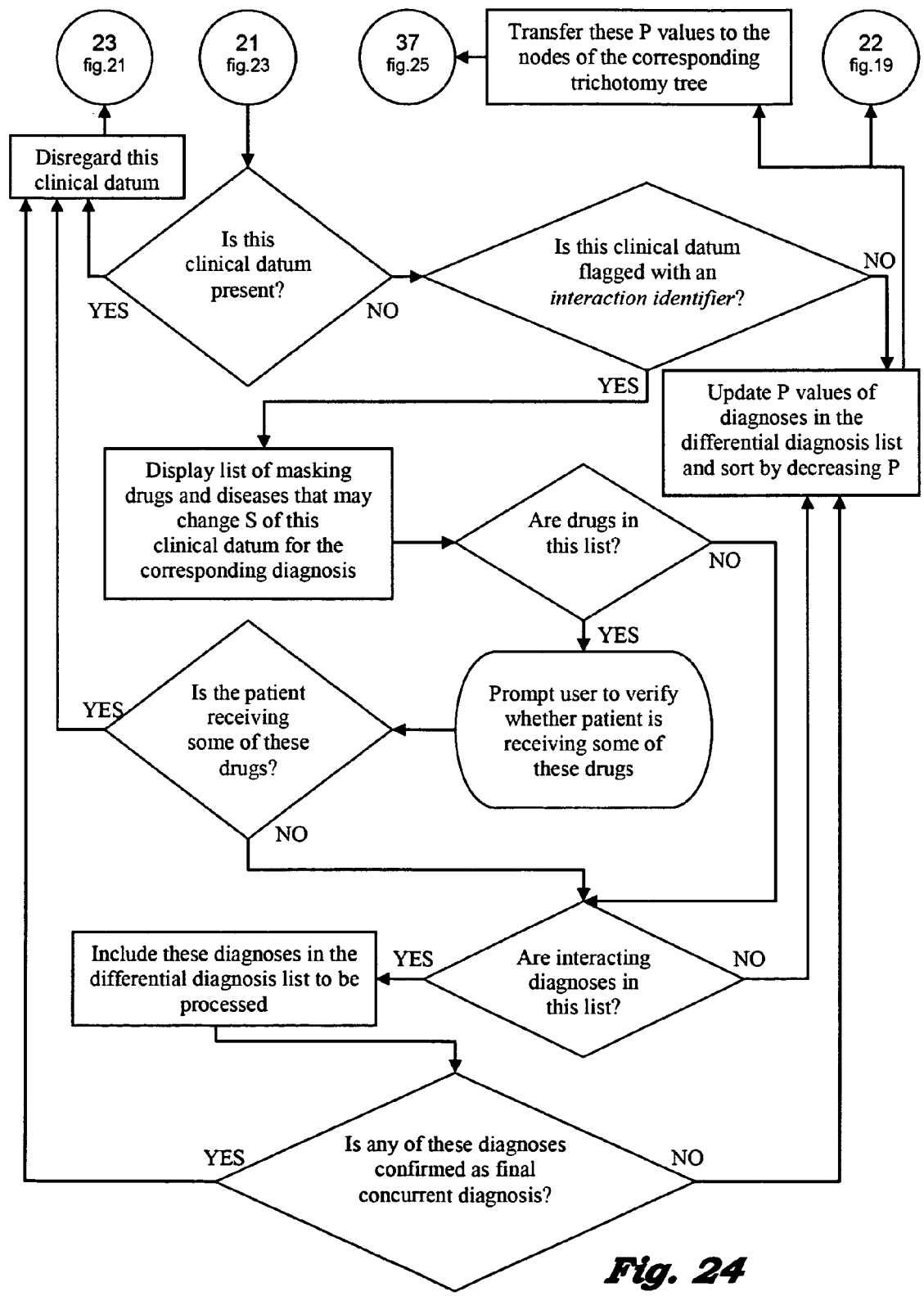

FIG. 24. Masking. When a best cost-effective clinical datum (y) is recommended, physician 24 is requested to verify whether it is absent (r) or present (j). If this clinical datum (y) is present (j), it is disregarded and the routine returns to S list 52 and similarly processes the next S clinical datum (y). If it is absent (r) and not flagged with an interaction identifier (Int), the P values in differential diagnosis list 34 will be updated and sorted by decreasing P. The algorithm goes to Conclusion of Diagnostic Quest (FIG. 19). If the recommended best cost-benefit clinical datum (y) is absent (r) and flagged with an interaction identifier (Int), it might be masked by a drug or concurrent disease (i). The algorithm checks the Masking Drugs and Diseases List that might change the S of this clinical datum (y) for the corresponding diagnosis (k). Physician 24 is asked to verify whether patient 26 is medicated with any listed drug, in which case clinical datum (y) is disregarded. If masking diseases (i) are listed, the algorithm verifies whether the corresponding diagnoses (k) have been included in differential diagnosis list 34, and if confirmed as final diagnoses, the clinical datum (y) is disregarded.

Figure 25:
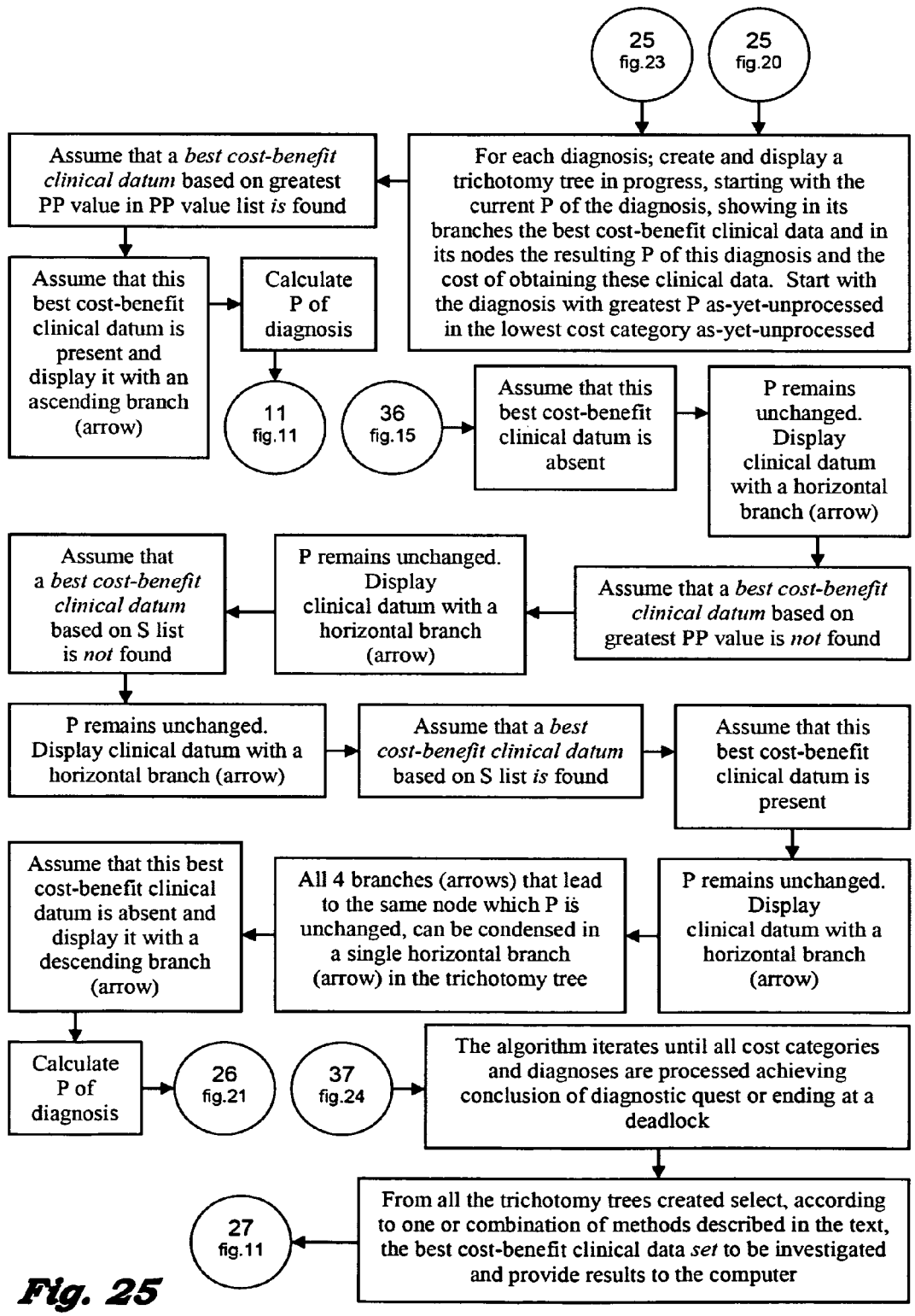

FIG. 25. Simultaneous recommendation of several best cost-benefit clinical data (y). A trichotomy tree 70 (see FIG. 7) in progress is created for each diagnosis (k). Beginning with the current P of diagnosis (k), its branches show the best cost-benefit clinical data (y) and its nodes show the resulting P of this diagnosis (k) and cost C(y) of obtaining these clinical data (y). Diagnoses (k) are processed in decreasing order of P. Best cost-benefit clinical data (y) recommended by the algorithm are successively assumed virtually present (j) and absent (r). The algorithm iterates until all cost categories and diagnoses (k) have been processed, marking either conclusion of the diagnostic quest or existence of a deadlock. From all existing trichotomy trees physician 24 must select—according to one or combination of strategies to be described— the best cost-benefit clinical data set to be investigated. When the resulting clinical data (y) become available, they must be provided to computer 12.

Figure 26:
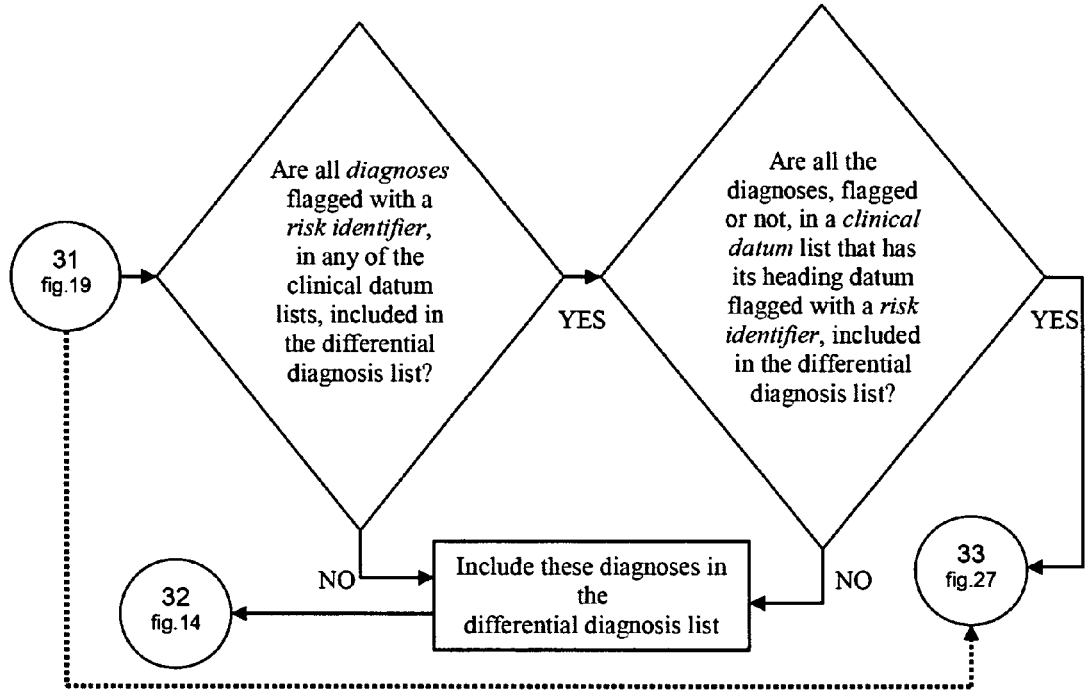
Figure 27:
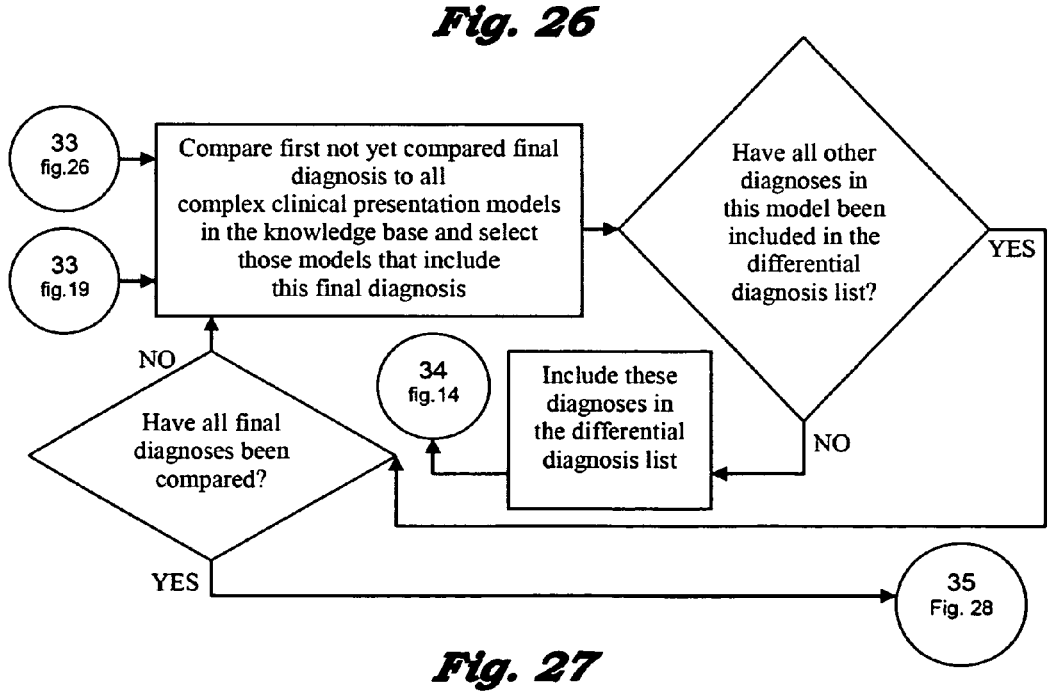

FIG. 26. Safety check for risk (Rsk) flagged diagnoses (k) and clinical data (m). This step is superfluous if the preferred all-inclusive method to integrate a differential diagnosis list 34 with all diagnoses (k) in all clinical datum lists is implemented. This routine ensures that all diagnoses (k) flagged with a risk (Rsk) identifier or included in a flagged clinical datum list were not omitted from differential diagnosis list 34.

FIG. 27. Safety check for related clinical entities. To preclude missing diagnoses (k), this routine checks for all clinical entities potentially associated with each final diagnosis. All complex clinical presentation models 80 (see FIG. 9) in which the final diagnosis is listed are checked, ensuring that all associated clinical entities are included in differential diagnosis list 34.

FIG. 28. Clinical presentation. When only one final diagnosis is obtained, it is displayed.

Concurrent final diagnoses, if included in a complex clinical presentation model, are displayed as a clinical presentation. Otherwise, they are displayed as unrelated final diagnoses. In either case, the message "End of diagnostic quest" is displayed on display 32.

Clearly, the apparatus and method of invention are highly scalable and other embodiments of the apparatus and method are possible. Therefore, the scope of the invention should be judged by the appended claims and their legal equivalents.

We claim:

1. A medical analytics method implemented on a computer for diagnosing at least one disease (i) afflicting a patient based on clinical data (m) that excludes subjective qualities of said clinical data (m) and excludes prevalence of said at least one disease (i), said method comprising:

1) compiling into the computer a knowledge base of disease (i) models exhibiting said clinical data (m), where there is more than 1 total number of disease (i) cases;

2) inputting into the computer clinical data present (j) in said patient;

3) matching by the computer said clinical data present (j) with said clinical data (m) in said knowledge base;

4) composing by the computer a differential diagnosis list of ruled in diagnoses (k) for each of said disease (i) models exhibiting at least one clinical datum (m) matching at least one clinical datum present (j);

5) calculating by the computer a probability P(k) for each of said ruled in diagnoses (k) by a mini-max procedure comprising the following sequential steps:

5a) obtaining sensitivities $S(i)_m$ of each of said clinical data (m) for diseases (i) based on disease (i) models that comprise a total number of disease (i) cases where the sensitivities $S(i)_m$ are obtained using:

$$S(i)_m = \frac{\text{number of disease}(i) \text{ cases manifesting clinical datum}(m)}{\text{total number of disease}(i) \text{ cases}};$$

5b) determining positive predictive values $PP(k)_j$ for clinical data present (j) supporting each of said ruled in diagnoses (k) where the positive predictive values $PP(k)_j$ are determined using:

$$PP(k)_j = \frac{S(k)_j}{S(1)_j + \ldots + S(k)_j + \ldots + S(n)_j},$$

where $S(k)_j$ are sensitivities of each clinical datum present (j) to said diagnoses (k), and n is the number of said ruled in diagnoses (k);

5c) assigning as probability P(k) of each ruled in diagnosis (k) the maximum value among said positive predictive values PP(k), through $PP(k)_z$ where the probabilities P(k) are assigned using:

$$P(k) = \max(PP(k)_1, PP(k)_2, \ldots, PP(k)_z),$$

where z is the number of said ruled in diagnoses (j); and 6) displaying on the computer said differential diagnosis list and said probability P(k) for each diagnosis (k) on a display for medical analytics; and where steps 1 through 6 are performed in the numerical order.

2. The method of claim 1, wherein said mini-max procedure further comprises:

7) selecting by the computer one of said clinical data present (j);
8) selecting by the computer a clinical datum absent (r) in said patient that corresponds to diagnosis (k);
9) creating by the computer a clinical data pair (j, r) consisting of said one of said clinical data present (j) and said one clinical datum absent (r); and
10) calculating by the computer a partial probability $P(k)_{j,r}$ of diagnosis (k) for said clinical data pair (j, r) where the partial probability $P(k)_{j,r}$ is calculated using:

$$\text{partial } P(k)_{j,r} = \frac{PP(k)_j(1 - S(k)_r)}{PP(1)_j(1 - S(1)_r) + \ldots PP(k)_j(1 - S(k)_r) + \ldots PP(n)_j(1 - S(n)_r)}.$$

where step 7 follows step 6 and steps 7 through 10 are performed in numerical order.

3. The method of claim 2, further comprising:

11) repeating the steps g) through j) to create additional clinical data pairs (j, r); and
12) calculating by the computer partial probabilities $P(k)_{j,r}$ for said additional clinical data pairs (j, r) such that said partial probabilities $P(1)_{j,r}, \ldots P(k)_{j,r}, \ldots, P(n)_{j,r}$ for corresponding ruled in diagnoses (k), where $k = 1 \ldots n$, satisfy a normalization condition:

$$\sum_{k=1}^{n} P(K)_{j,r} = 1$$

where step 11 follows step 10 and steps 11 and 12 are performed in numerical order.

4. The method of claim 3, wherein said mini-max procedure further comprises creating by the computer a mini-max table for each of said diagnoses (k) in said differential diagnosis list, whereby a first data column of each said mini-max table comprises said positive predictive values $PP(k)_j$ of said clinical data present (j) in said patient for said diagnosis (k) for which said mini-max table is created and a first row of each said mini-max table comprises said sensitivities $S(k)_r$ of said clinical data absent (r) for said diagnosis (k) for which said mini-max table is created.

5. The method of claim 4, further comprising the steps of:

13) transferring by the computer each said partial probability $P(k)_{j,r}$ into cells of said mini-max table where said $PP(k)_j$ for each said clinical datum present (j) and said sensitivity $S(k)_r$ for each said clinical datum absent (r) converge; and
14) selecting by the computer from among said partial probabilities $P(k)_{j,r}$ in said cells a determining partial probability $DP(k)_{j,r}$ having the smallest value in its row and the greatest value in its column where step 13 follows step 12 and steps 13 and 14 are performed in numerical order.

6. The method of claim 5, wherein from each said mini-max table, said determining by the computer partial probability $DP(k)_{j,r}$ is selected by the computer as a total probability TP(k) for said diagnosis (k) for which said mini-max table is created.

7. The method of claim 6, further comprising confirming by the computer as final diagnoses (k) those of said diagnoses (k) for which said total probability TP(k) is greater than a confirmation threshold value CT, and ruling out by the computer those of said diagnoses (k) for which said total probability TP(k) is smaller than a deletion threshold DT.

8. The method of claim 7, further comprising repeating by the computer the steps of claim 1 through claim 7 until said diagnoses (k) in said differential diagnosis list have satisfied said confirmation threshold CT and said deletion threshold DT.

9. The method of claim 1, further comprising recommending by the computer a best cost-benefit clinical datum (m) to investigate in said patient by:

15) selecting from said disease (i) models corresponding to said diagnoses (k) ruled in into said differential diagnosis list a clinical datum not yet investigated (y) in said patient; and
16) determining a cost C(y) of collecting said clinical datum not yet investigated (y) as follows:

$$C(y) = \max(\text{expense}(y), \text{risk}(y), \text{discomfort}(y)),$$

where said cost C(y) comprises the maximum of expense, risk and discomfort for said patient where step 15 follows step 6 and steps 15 and 16 are performed in numerical order.

10. The method of claim 9, further comprising calculating by the computer a total probability TP(k) for each of said diagnoses (k) ruled in into said differential diagnosis list by including in said mini-max procedure said clinical datum not yet investigated (y).

11. The method of claim 10, wherein said clinical datum not yet investigated (y) is treated by the computer as if present in said patient when computing said total probability TP(k) and wherein said clinical datum not yet investigated (y) is treated by the computer as if absent in said patient when computing said total probability TP(k).

12. The method of claim 11, further comprising selecting by the computer said clinical datum not yet investigated (y) such that said cost C(y) is minimized and a change to said total probability TP(k) is maximized.

13. The method of claim 10, further comprising simultaneously by the computer recommending collecting from said patient a plurality of clinical data not yet investigated (y) that minimize said cost C(y) and maximize a change to said total probability TP(k).

14. The method of claim 13, further comprising calculating by the computer a total probability TP(k) for each of said diagnoses (k) in said differential diagnosis list with said plurality of clinical data not yet investigated (y) treated as if present in said patient, and then computing said total probability TP(k) with said plurality of clinical data not yet investigated (y) treated as if absent in said patient.

15. The method of claim 1, further comprising determining by the computer whether the absence of any clinical datum among said clinical data (m) will decrease a total probability TP(k) of said corresponding diagnosis (k), and aborting said mini-max procedure for said clinical datum (m) when its absence does not decrease said total probability TP(k).

16. The method of claim 1, further comprising the steps of:
   a) distinguishing competitive diagnoses (k) from concurrent diagnoses (k); and
   b) applying said distinction to diagnoses (k) ruled in on said differential diagnosis list.

17. The method of claim 1, further comprising diagnosing by the computer complex clinical presentations comprising the steps of:
   17) creating complex clinical presentation models listing all potentially related diagnoses (k); and
   18) transferring all said potentially related diagnoses (k) to said differential diagnosis list when one confirmed diagnosis matches any of said potentially related diagnoses
where step 17 follows step 6 and steps 17 and 18 are performed in numerical order.

18. The method of claim 1, further comprising checking by the computer for interactions between drugs having the potential of masking any of said clinical data (m) belonging to a primary disease (i), comprising the steps of:
   19) flagging all said disease (i) models in said knowledge base that include at least one clinical datum (m) susceptible to being masked by said drugs;
   20) listing for said disease (i) models all said drugs and concurrent diagnoses (k) having the potential of masking any of said clinical data (m) belonging to said primary disease (i);
   21) confirming presence of any of said drugs in said patient; and
   22) removing any clinical datum (m) masked by said drugs from consideration if at least one of said drugs is confirmed present
where step 19 follows step 6 and steps 19 through 22 are performed in numerical order.

19. The method of claim 1, further comprising checking by the computer for interactions between concurrent diseases (k) having the potential of masking any of said clinical data (m) belonging to a primary disease (i), comprising the steps of:
   23) flagging all said disease (i) models in said knowledge base that include at least one clinical datum (m) susceptible to being masked by said concurrent diseases (i);
   24) listing for said disease (i) models all said concurrent diseases (i) having the potential of masking any of said clinical data (m) belonging to said primary disease (i);
   25) confirming presence of any of said concurrent diseases (i) in said patient; and
   26) removing any clinical datum (m) masked from each corresponding disease (i) that contains said clinical datum (m) in its disease (i) model
where step 23 follows step 6 and steps 23 through 26 are performed in numerical order.

20. A medical analytics system comprising a computer for aiding a physician in diagnosing at least one disease (i) afflicting a patient based on clinical data (m) that excludes subjective qualities of said clinical data (m) and excludes prevalence of said at least one disease (i), said system comprising:
   1) a computer memory knowledge base of disease (i) models exhibiting said clinical data (m), where there is more than 1 total number of disease (i) cases;
   2) an input device for inputting clinical data present (i) in said patient into said computer for matching said clinical data present (i) with said clinical data (m) in said knowledge base;
   3) a display for displaying a differential diagnosis list of ruled in diagnoses (k) for each of said disease (i) models exhibiting at least one clinical datum (m) matching at least one clinical datum present (j);
   4) a processor for computing a probability P(k) for each of said ruled in diagnoses (k) by a mini-max procedure;
   5) a network connecting said processor with said knowledge base to enable said processor to obtain from said knowledge base sensitivities $S(i)_m$ of each of said clinical data (m) for diseases (i) based on disease (i) models that comprise a total number of disease (i) cases where the sensitivities $S(i)_m$ are obtained using:

$$S(i)_m = \frac{\text{number of disease}(i) \text{ cases manifesting clinical datum}(m)}{\text{total number of disease}(i) \text{ cases}};$$

and to further enable said processor to determine positive predictive values $PP(k)_j$ for clinical data present (j) supporting each of said ruled in diagnoses (k) where the positive predictive values PP(k)1 are determined using:

$$PP(k)_j = \frac{S(k)_j}{S(1)_j + \ldots + S(k)_j + \ldots + S(n)_j},$$

where S(k) are sensitivities of each clinical datum present (j) to said diagnoses (k), and n is the number of said ruled in diagnoses (k); and to still further enable said processor to assign as probability P(k) of each ruled in diagnosis (k) the maximum value among said positive predictive values $PP(k)_1$ through $PP(k)_z$ where the probabilities P(k) are assigned using:

$$P(k) = \max(PP(k)_1, PP(k)_2, \ldots, PP(k)_z),$$

where z is the number of said ruled in diagnoses (j);
   whereby said display displays said differential diagnosis list and said probability P(k) for each diagnosis (k) to aid said physician in a diagnostic quest; and
where steps 1 through 6 are performed in the numerical order.

* * * * *